(12) United States Patent
Kim et al.

(10) Patent No.: US 8,697,882 B2
(45) Date of Patent: Apr. 15, 2014

(54) COMPOUND, RESIN AND PHOTORESIST COMPOSITION

(75) Inventors: Hyungjoo Kim, Toyonaka (JP); Akira Kamabuchi, Kobe (JP); Yuichi Mukai, Kobe (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 103 days.

(21) Appl. No.: 13/175,072

(22) Filed: Jul. 1, 2011

(65) Prior Publication Data

US 2012/0009519 A1 Jan. 12, 2012

(30) Foreign Application Priority Data

Jul. 6, 2010 (JP) .................................. 2010-153726

(51) Int. Cl.
| | | |
|---|---|---|
| *C07D 291/00* | (2006.01) | |
| *C07D 275/02* | (2006.01) | |
| *C07D 275/04* | (2006.01) | |
| *C07D 275/06* | (2006.01) | |
| *C07C 317/30* | (2006.01) | |
| *C07D 291/02* | (2006.01) | |

(52) U.S. Cl.
CPC ............ *C07D 291/02* (2013.01); *C07D 275/02* (2013.01); *C07D 275/04* (2013.01); *C07D 275/06* (2013.01); *C07C 317/30* (2013.01)
USPC .............. 548/122; 548/206; 548/207; 568/30

(58) Field of Classification Search
CPC .. C07D 291/02; C07D 275/02; C07D 275/04; C07D 275/06; C07C 317/30
USPC ................ 562/37; 548/122, 206, 207; 568/30
See application file for complete search history.

(56) References Cited

U.S. PATENT DOCUMENTS

| | | | | |
|---|---|---|---|---|
| 6,353,112 | B1 * | 3/2002 | Baker et al. .................... | 548/207 |
| 7,462,721 | B2 * | 12/2008 | Jin et al. ......................... | 546/118 |
| 7,544,754 | B2 * | 6/2009 | Leir et al. ....................... | 526/257 |
| 2004/0186093 | A1 * | 9/2004 | Lee et al. .................. | 514/211.01 |
| 2005/0019638 | A1 * | 1/2005 | Ravikiran et al. ............... | 429/33 |
| 2006/0194982 | A1 | 8/2006 | Harada et al. | |
| 2006/0199100 | A1 | 9/2006 | Kanda | |
| 2007/0072115 | A1 | 3/2007 | Hatakeyama et al. | |

\* cited by examiner

*Primary Examiner* — John Chu
(74) *Attorney, Agent, or Firm* — Birch, Stewart, Kolasch & Birch, LLP

(57) ABSTRACT

The present invention provides a compound represented by the formula (I):

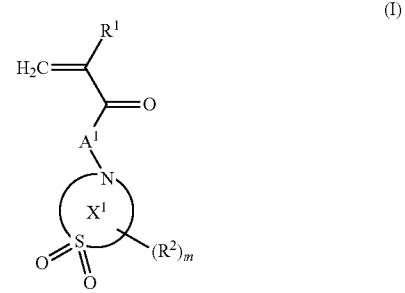

wherein $R^1$ represents a hydrogen atom, a halogen atom or a C1-C6 alkyl group which may have one or more halogen atoms, $A^1$ represents a divalent connecting group, $X^1$ represents a C2-C36 heterocyclic group and one or more —$CH_2$— in the C2-C36 heterocyclic group can be replaced by —CO— or —O—, $R^2$ is independently in each occurrence a halogen atom, a hydroxyl group, a C1-C24 hydrocarbon group, a C1-C12 alkoxy group, a C2-C4 acyl group or a C2-C4 acyloxy group, and m represents an integer of 0 to 10.

3 Claims, No Drawings

COMPOUND, RESIN AND PHOTORESIST COMPOSITION

This nonprovisional application claims priority under 35 U.S.C. §119(a) on Patent Application No. 2010-153726 filed in JAPAN on Jul. 6, 2010, the entire contents of which are hereby incorporated by reference.

FIELD OF THE INVENTION

The present invention relates to a novel compound, a resin comprising a structural unit derived from the compound and a photoresist composition comprising the resin.

BACKGROUND OF THE INVENTION

US 2006/0194982 A1 discloses a resin comprising the structural units derived from the compounds represented by the following formulae:

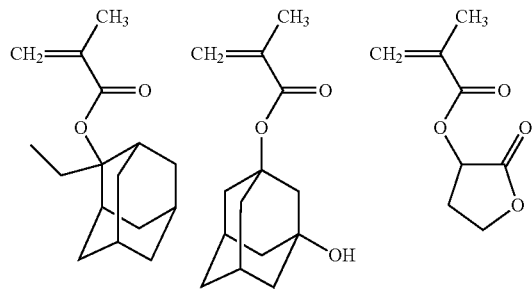

and a photoresist composition comprising the resin.

SUMMARY OF THE INVENTION

The present invention relates to the followings:
<1> A compound represented by the formula (I):

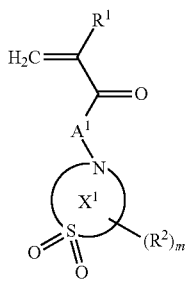

wherein $R^1$ represents a hydrogen atom, a halogen atom or a C1-C6 alkyl group which may have one or more halogen atoms, $A^1$ represents a divalent connecting group, $X^1$ represents a C2-C36 heterocyclic group and one or more —$CH_2$— in the C2-C36 heterocyclic group can be replaced by —CO— or —O—, $R^2$ is independently in each occurrence a halogen atom, a hydroxyl group, a C1-C24 hydrocarbon group, a C1-C12 alkoxy group, a C2-C4 acyl group or a C2-C4 acyloxy group, and m represents an integer of 0 to 10;

<2> The compound according to <1>, which is represented by the formula (II):

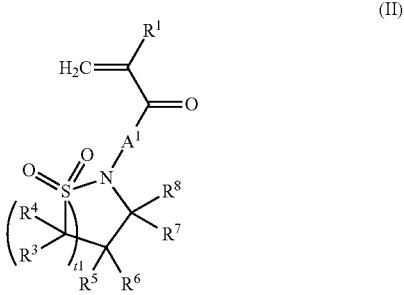

wherein $R^1$ represents a hydrogen atom, a halogen atom or a C1-C6 alkyl group which may have one or more halogen atoms, $A^1$ represents a divalent connecting group, $R^3$, $R^4$, $R^5$, $R^6$, $R^7$ and $R^8$ independently each represents a hydrogen atom or a C1-C24 hydrocarbon group, and at least two selected from $R^3$, $R^4$, $R^5$, $R^6$, $R^7$ and $R^8$ may be bonded each other to form a ring, and one or more hydrogen atoms in the C1-C24 hydrocarbon group and the ring can be replaced by a halogen atom, a hydroxyl group, a C1-C12 alkyl group, a C1-C12 alkoxy group, a C2-C4 acyl group or a C2-C4 acyloxy group, and one or more —$CH_2$— in the C1-C24 hydrocarbon group and the ring can be replaced by —CO— or —O—, and t1 represents an integer of 0 to 3;

<3> The compound according to <1> or <2>, which is represented by the formula (III):

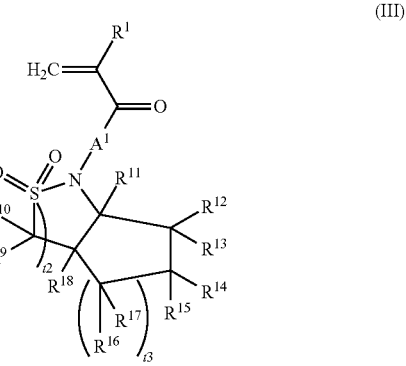

wherein $R^1$ represents a hydrogen atom, a halogen atom or a C1-C6 alkyl group which may have one or more halogen atoms, $A^1$ represents a divalent connecting group, $R^9$, $R^{10}$, $R^{11}$, $R^{12}$, $R^{13}$, $R^{14}$, $R^{15}$, $R^{16}$, $R^{17}$ and $R^{18}$ independently each represents a hydrogen atom or a C1-C12 hydrocarbon group, and at least two selected from $R^9$, $R^{10}$, $R^{11}$, $R^{12}$, $R^{13}$, $R^{14}$, $R^{15}$, $R^{16}$, $R^{17}$ and $R^{18}$ may be bonded each other to form a ring, and one or more hydrogen atoms in the C1-C12 hydrocarbon group and the ring can be replaced by a halogen atom, a hydroxyl group, a C1-C12 alkyl group, a C1-C12 alkoxy group, a C2-C4 acyl group or a C2-C4 acyloxy group, and one or more —$CH_2$— in the C1-C12 hydrocarbon group and the ring can be replaced by —CO— or —O—, and t2 and t3 independently each represents an integer of 0 to 3;

<4> The compound according to <1>, <2> or <3>, which is represented by the formula (IV):

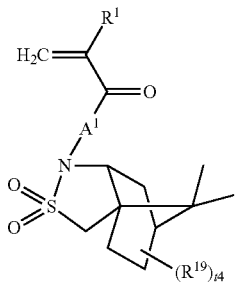

wherein $R^1$ represents a hydrogen atom, a halogen atom or a C1-C6 alkyl group which may have one or more halogen atoms, $A^1$ represents a divalent connecting group, $R^{19}$ represents a halogen atom, a hydroxyl group, a C1-C12 alkyl group, a C1-C12 alkoxy group, a C2-C4 acyl group or a C2-C4 acyloxy group, and t4 represents an integer of 0 to 8;
<5> A resin comprising a structural unit derived from the compound according to any one of <1> to <4>;
<6> The resin according to <5>, wherein the resin has an acid-labile group and is itself insoluble or poorly soluble in an alkali aqueous solution but becomes soluble in an alkali aqueous solution by the action of an acid;
<7> A photoresist composition comprising an acid generator and the resin according to <5> or <6>;
<8> The photoresist composition according to <7>, wherein the photoresist composition further contains a basic compound;
<9> A process for producing a photoresist pattern comprising the following steps (1) to (5):

(1) a step of applying the photoresist composition according to <7> or <8> on a substrate,
(2) a step of forming a photoresist film by conducting drying,
(3) a step of exposing the photoresist film to radiation,
(4) a step of baking the exposed photoresist film, and
(5) a step of developing the baked photoresist film with an alkaline developer, thereby forming a photoresist pattern.

DESCRIPTION OF PREFERRED EMBODIMENTS

The compound of the present invention is a compound represented by the formula (I):

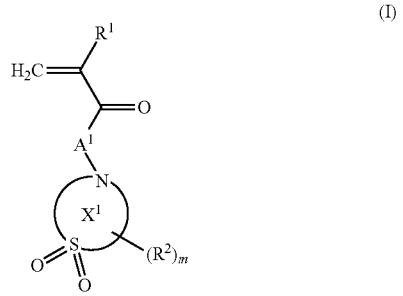

wherein $R^1$ represents a hydrogen atom, a halogen atom or a C1-C6 alkyl group which may have one or more halogen atoms, $A^1$ represents a divalent connecting group, $X^1$ represents a C2-C36 heterocyclic group and one or more —$CH_2$— in the C2-C36 heterocyclic group can be replaced by —CO— or —O—, $R^2$ is independently in each occurrence a halogen atom, a hydroxyl group, a C1-C24 hydrocarbon group, a C1-C12 alkoxy group, a C2-C4 acyl group or a C2-C4 acyloxy group, and m represents an integer of 0 to 10 (hereinafter, simply referred to as the compound (I)).

Examples of the halogen atom represented by $R^1$ include a fluorine atom, a chlorine atom, a bromine atom and an iodine atom.

Examples of the C1-C6 alkyl group represented by $R^1$ include a methyl group, an ethyl group, a propyl group, an isopropyl group, a butyl group, a sec-butyl group, a tert-butyl group, a pentyl group and a hexyl group, and a C1-C4 alkyl group is preferably, and C1-C2 alkyl group is more preferable and a methyl group is especially preferable. The C1-C6 alkyl group may have one or more halogen atoms, and examples of the C1-C6 alkyl group having one or more halogen atoms include a perfluoromethyl group, a perfluoroethyl group, a perfluoropropyl group, a perfluoroisopropyl group, a perfluorobutyl group, a perfluorosec-butyl group, a perfluorotert-butyl group, a perfluoropentyl group, a perfluorohexyl group, a perchloromethyl group, perbromomethyl group and a periodomethyl group.

$R^1$ is preferably a hydrogen atom or a C1-C6 alkyl group, more preferably a hydrogen atom or a C1-C4 alkyl group, and especially preferably a hydrogen atom or a methyl group.

Examples of the divalent connecting group represented by $A^1$ include *-$T^1$-$(CH_2)_n$—CO— in which $T^1$ represents —O— or —NH—, n represents an integer of 1 to 4, and * represents a binding position to $CH_2$=C($R^1$)—CO—, and $T^1$ is preferably —O— and n is preferably 1.

Examples of $A^1$ include a single bond, *—O—$CH_2$—CO—, *—O—$(CH_2)_2$—CO—, *—O—$(CH_2)_3$—CO—, *—O—$(CH_2)_4$—CO—, *—O—$(CH_2)_5$—CO—, *—O—$(CH_2)_6$—CO—, *—NH—$CH_2$—CO—, *—NH—$(CH_2)_2$—CO—, *—NH—$(CH_2)_3$—CO—, *—NH—$(CH_2)_4$—CO—, *—NH—$(CH_2)_5$—CO— and *—NH—$(CH_2)_6$—CO— in which * represents a binding position to $CH_2$=C($R^1$)—CO—.

Examples of the group represented by the formula (IA):

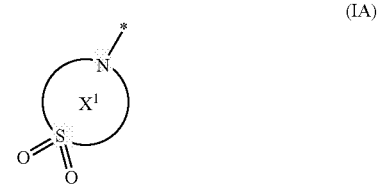

wherein $X^1$ is the same as defined above and * represents a binding position to $A^1$ include the following groups.

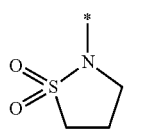 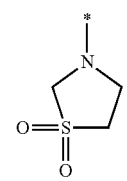 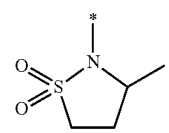

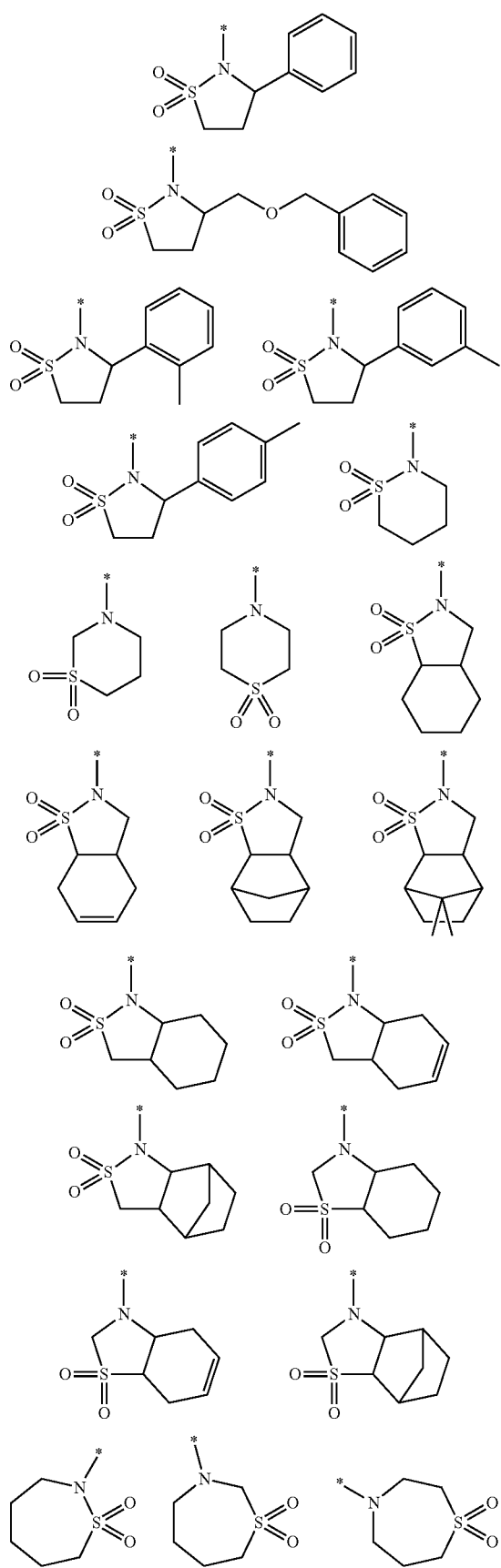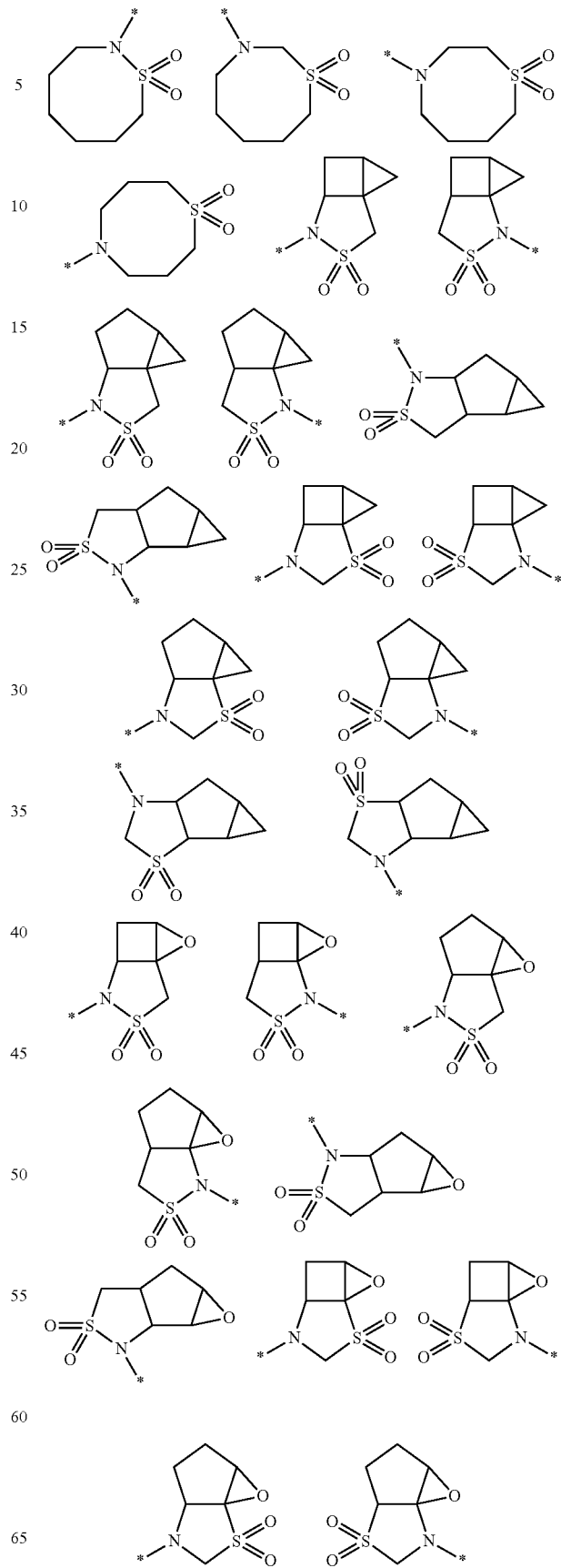

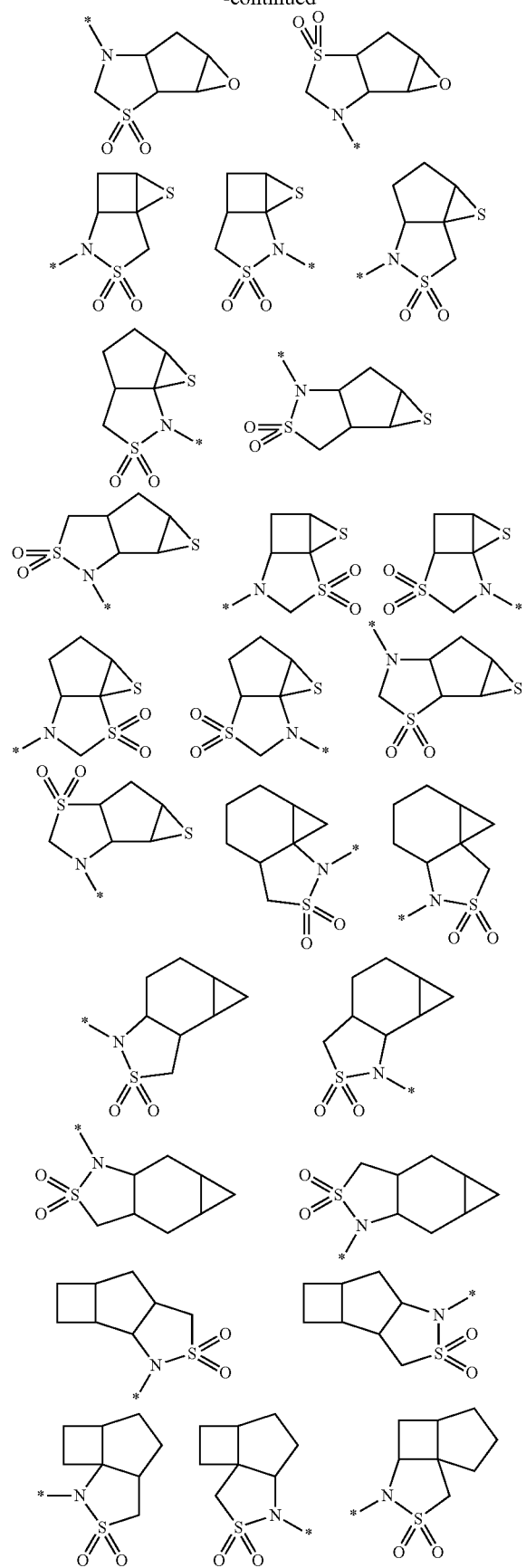
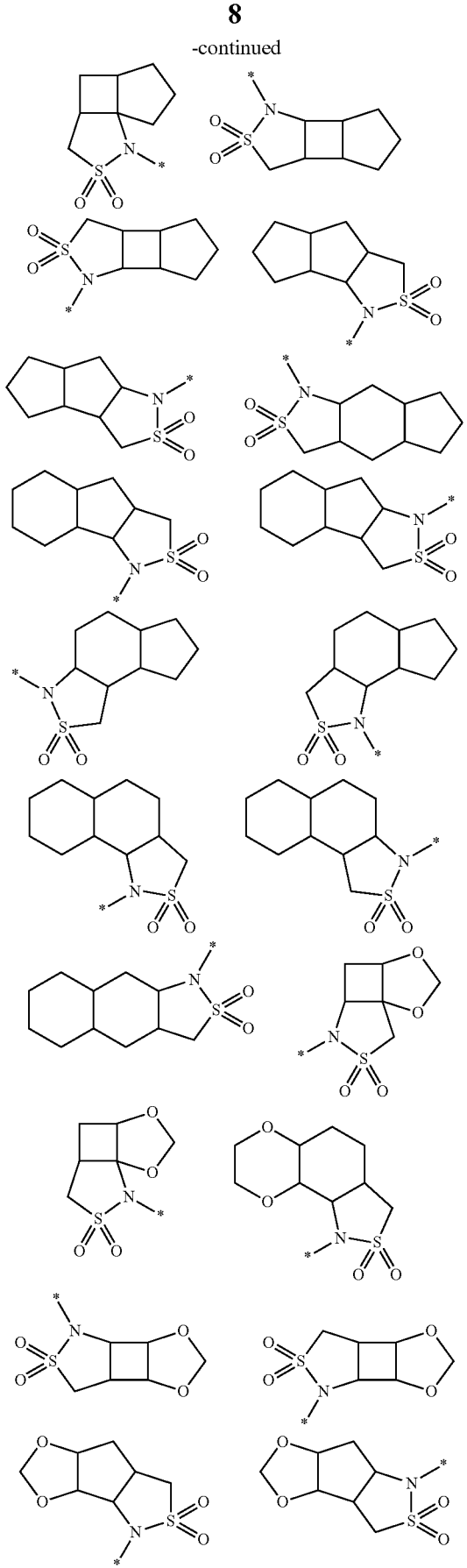

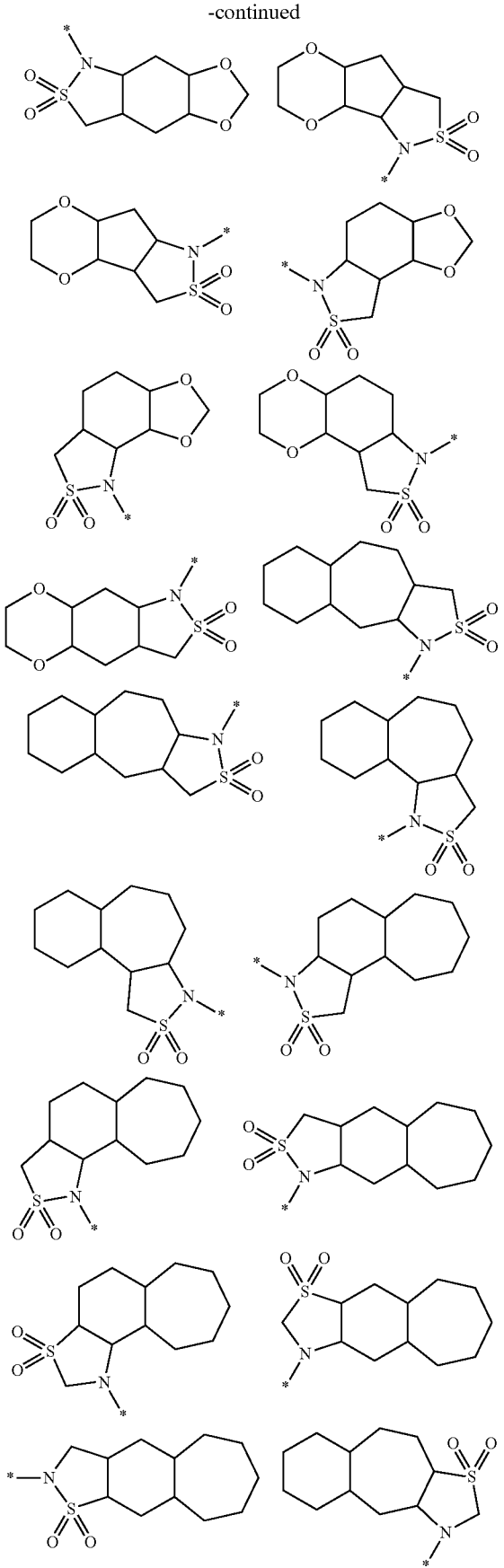
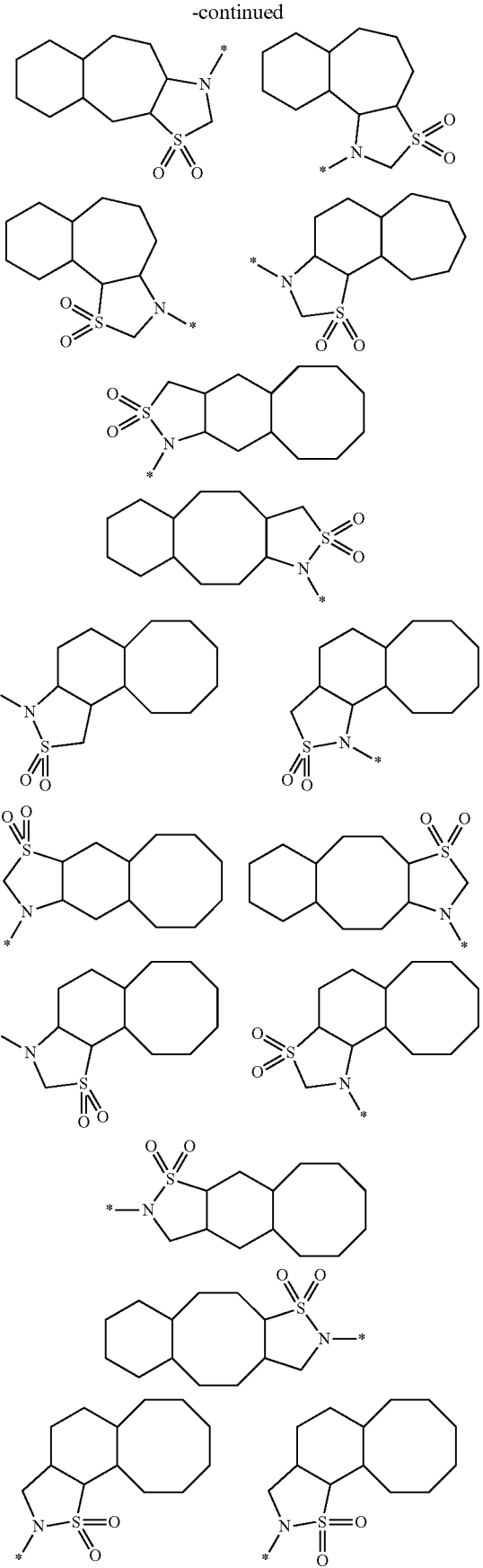

11
-continued
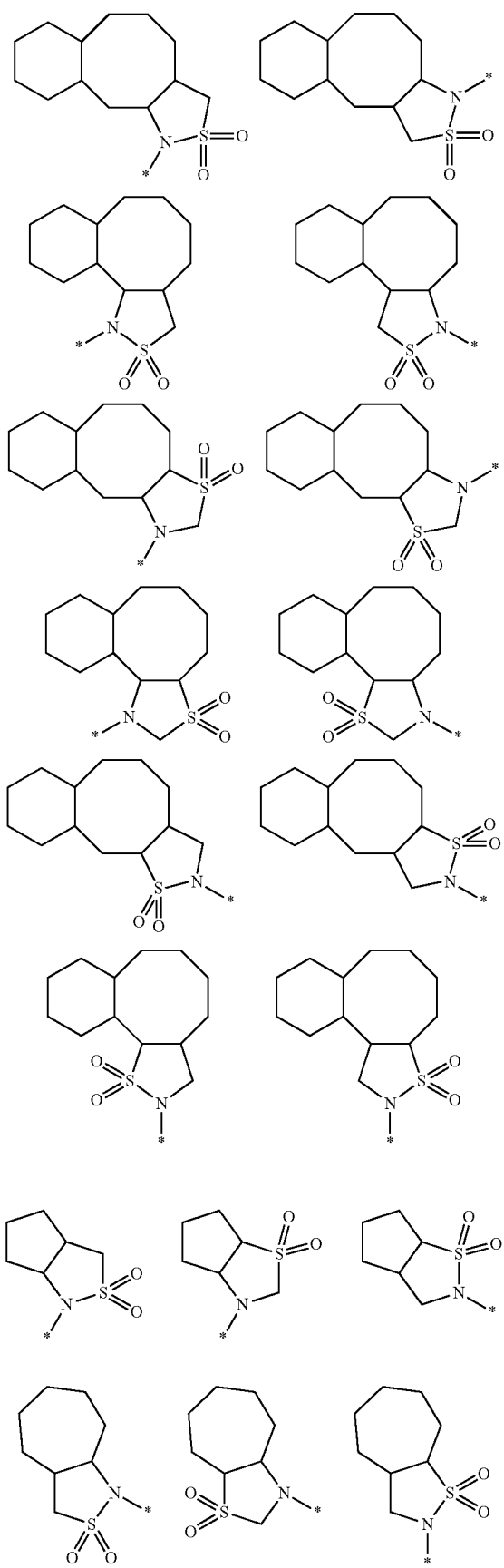
12
-continued
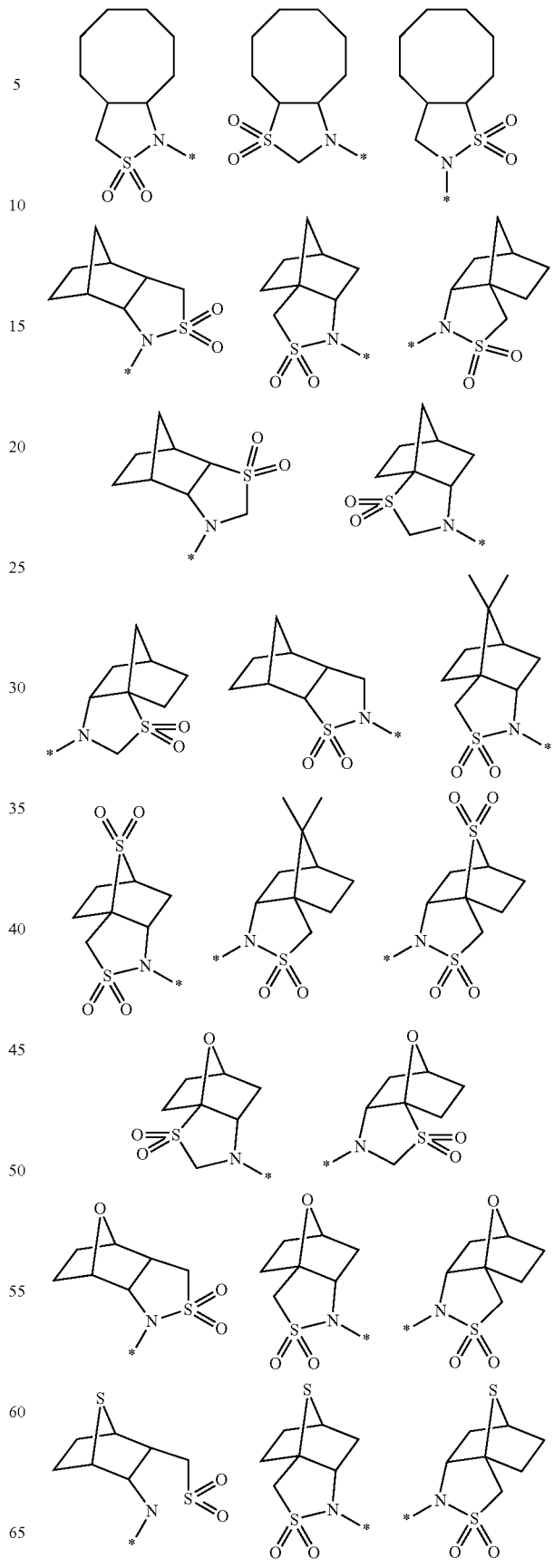

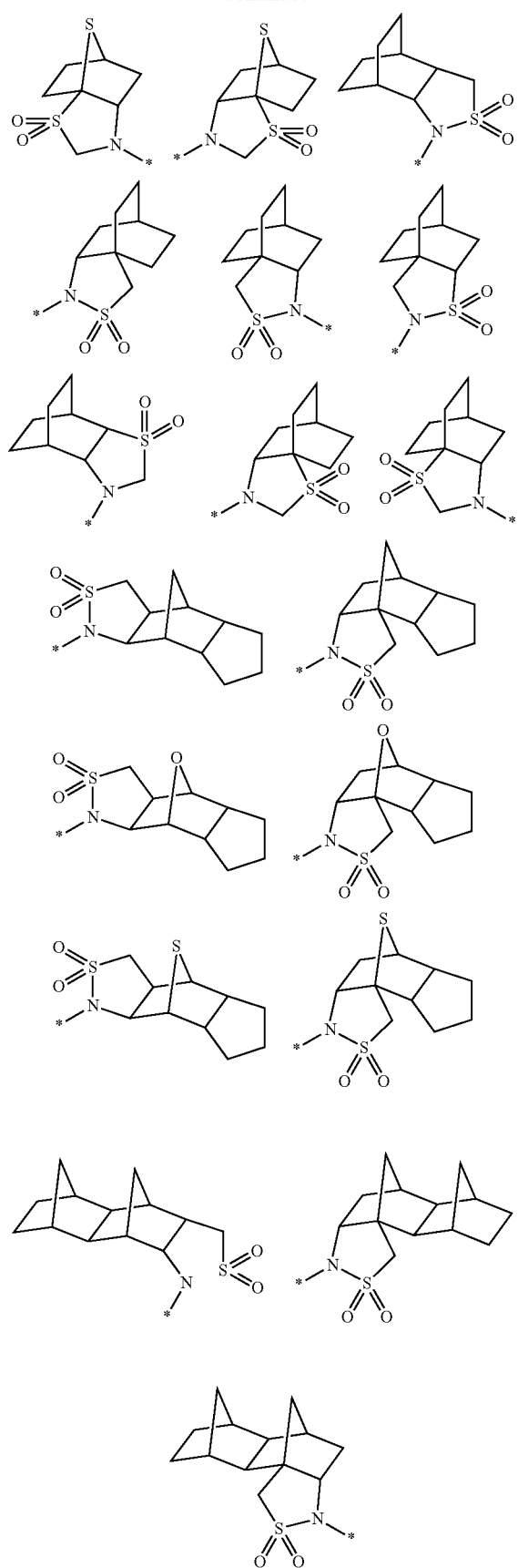
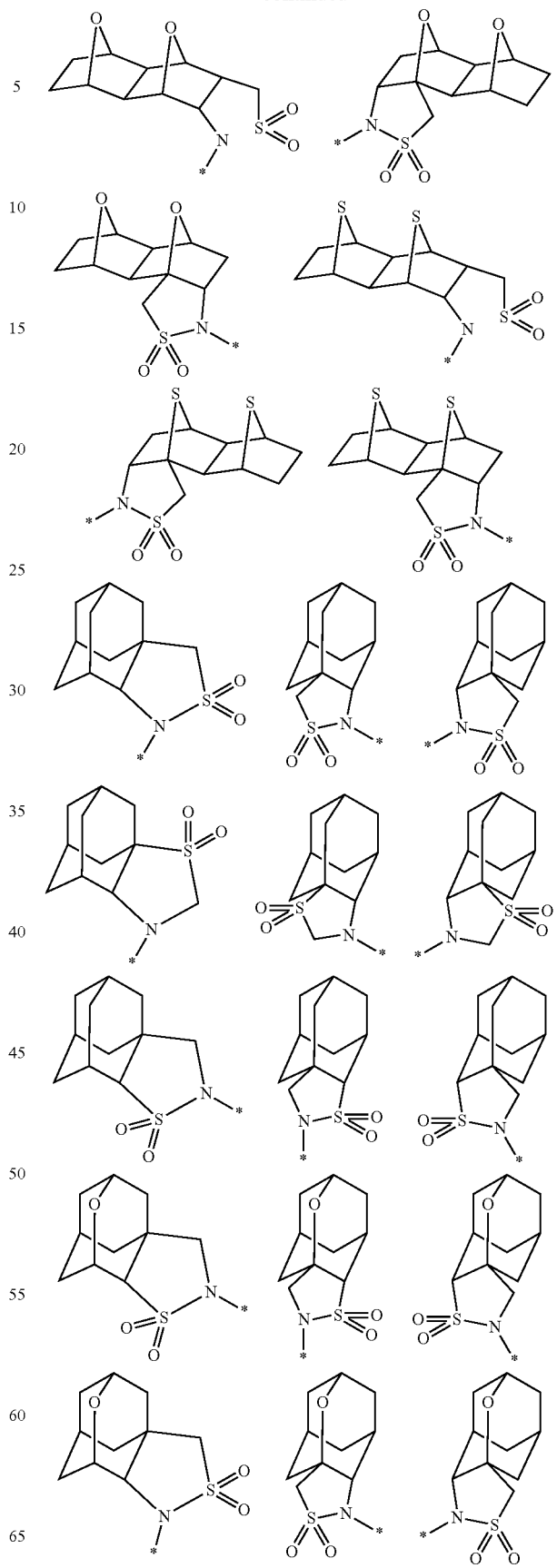

-continued

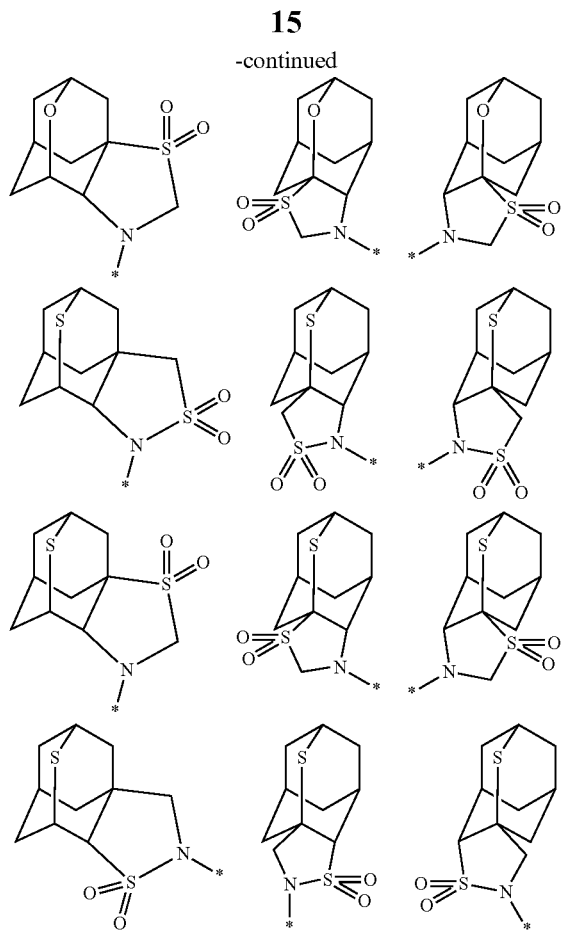

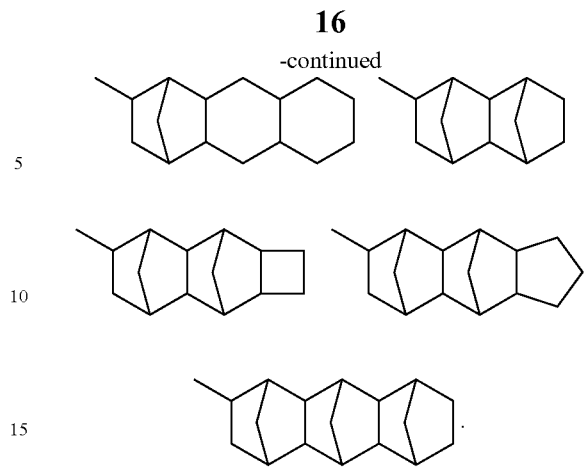

Examples of the aromatic hydrocarbon group include a C6-C24 aryl group such as a phenyl group, a naphthyl group, an anthryl group, a p-methylphenyl group, a p-tert-butyl group, a p-adamantylphenyl group, a tolyl group, a xylyl group, a cumyl group, a mesityl group, a biphenyl group, a phenanthryl group, a 2,6-diethylphenyl group and a 2-methyl-6-ethylphenyl group. Examples of the C1-C12 alkoxy group include a methoxy group, an ethoxy group, a propoxy group, an isopropoxy group, a butoxy group, a sec-butoxy group, a tert-butoxy group, a pentyloxy group and a hexyloxy group. Examples of the C2-C4 acyl group include an acetyl group, a propionyl group and a butyryl group, and examples of the C2-C4 acyloxy group include an acetyloxy group, a propionyloxy group and a butyryloxy group.

It is preferred that m is an integer of 0 to 6 and it is more preferred that m is an integer of 0 to 4.

The compound (I) is preferably a compound represented by the formula (II):

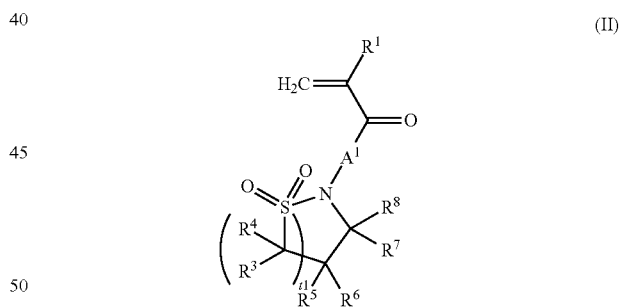

$R^2$ is independently in each occurrence a halogen atom, a hydroxyl group, a C1-C24 hydrocarbon group, a C1-C12 alkoxy group, a C2-C4 acyl group or a C2-C4 acyloxy group, and it is preferred that $R^2$ is independently in each occurrence an alkyl group, and it is more preferred that $R^2$ is independently in each occurrence C1-C12 alkyl group. Examples of the halogen atom include a fluorine atom, a chlorine atom, a bromine atom and an iodine atom, and a fluorine atom is preferable. Examples of the C1-C24 hydrocarbon group include an aliphatic hydrocarbon group, a saturated cyclic hydrocarbon group and an aromatic hydrocarbon group. Examples of the aliphatic hydrocarbon group include a C1-C12 alkyl group such as a methyl group, an ethyl group, a propyl group, an isopropyl group, a butyl group, a pentyl group, a hexyl group, a heptyl group and an octyl group. The saturated cyclic hydrocarbon group may bemonocyclicorpolycyclic, and examples thereof include amonocyclic alicyclic hydrocarbon group such as a C3-C12 cycloalkyl group (e.g. a cyclopentyl group, a cyclohexyl group, a methylcyclohexyl group, a dimethylcyclohexyl group, a cycloheptyl group and a cyclooctyl group) and a polycyclic alicyclic hydrocarbon group such as a decahydronaphthyl group, an adamantyl group, a norbornyl group, a methylnorbornyl group, and the following:

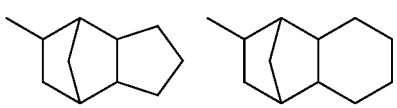

wherein $R^1$ represents a hydrogen atom, a halogen atom or a C1-C6 alkyl group which may have one or more halogen atoms, $A^1$ represents a divalent connecting group, $R^3$, $R^4$, $R^5$, $R^6$, $R^7$ and $R^8$ independently each represents a hydrogen atom or a C1-C24 hydrocarbon group, and at least two selected from $R^3$, $R^4$, $R^5$, $R^6$, $R^7$ and $R^8$ may be bonded each other to form a ring, and one or more hydrogen atoms in the C1-C24 hydrocarbon group and the ring can be replaced by a halogen atom, a hydroxyl group, a C1-C12 alkyl group, a C1-C12 alkoxy group, a C2-C4 acyl group or a C2-C4 acyloxy group, and one or more —CH$_2$— in the C1-C24 hydrocarbon group and the ring can be replaced by —CO— or —O—, and t1 represents an integer of 0 to 3, and is more preferably a compound represented by the formula (III):

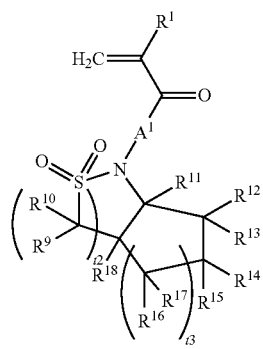

(III)

wherein $R^1$ represents a hydrogen atom, a halogen atom or a C1-C6 alkyl group which may have one or more halogen atoms, $A^1$ represents a divalent connecting group, $R^9$, $R^{10}$, $R^{11}$, $R^{12}$, $R^{13}$, $R^{14}$, $R^{15}$, $R^{16}$, $R^{17}$ and $R^{18}$ independently each represents a hydrogen atom or a C1-C12 hydrocarbon group, and at least two selected from $R^9$, $R^{10}$, $R^{11}$, $R^{12}$, $R^{13}$, $R^{14}$, $R^{15}$, $R^{16}$, $R^{17}$ and $R^{18}$ may be bonded each other to form a ring, and one or more hydrogen atoms in the C1-C12 hydrocarbon group and the ring can be replaced by a halogen atom, a hydroxyl group, a C1-C12 alkyl group, a C1-C12 alkoxy group, a C2-C4 acyl group or a C2-C4 acyloxy group, and one or more —CH$_2$— in the C1-C12 hydrocarbon group and the ring can be replaced by —CO— or —O—, and t2 and t3 independently each represents an integer of 0 to 3, and is especially preferably a compound represented by the formula (IV):

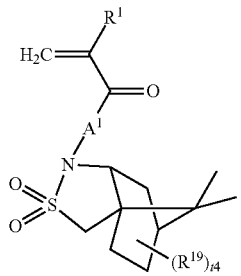

(IV)

wherein $R^1$ represents a hydrogen atom, a halogen atom or a C1-C6 alkyl group which may have one or more halogen atoms, $A^1$ represents a divalent connecting group, $R^{19}$ represents a halogen atom, a hydroxyl group, a C1-C12 alkyl group, a C1-C12 alkoxy group, a C2-C4 acyl group or a C2-C4 acyloxy group, and t4 represents an integer of 0 to 8.

Examples of the compound (I) include the following.

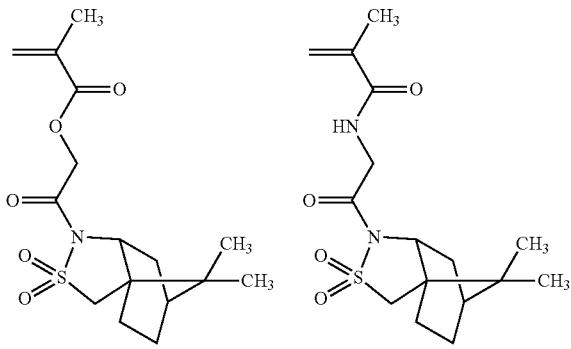 [SMILES: C=C(C)C(=O)OCC(=O)N1C2CC3CCC2(CS1(=O)=O)C3(C)C ; C=C(C)C(=O)NCC(=O)N1C2CC3CCC2(CS1(=O)=O)C3(C)C]

The compound (I) can be produced, for example, by reacting 2,10-camphorsultam with acrylic acid or methacrylic acid in the presence of a strong base such as sodium hydride. The reaction is preferably conducted at 10 to 30° C., and is preferably carried out in a solvent such as tetrahydrofuran and N,N-dimethylformamide.

The compound (I) can be isolated by extracting the reaction mixture with an organic solvent such as ethyl acetate followed by concentrating the organic layer obtained. The obtained compound (I) can be further purified with conventional purification means such as column chromatography.

The resin of the present invention comprises a structural unit derived from the compound (I). The resin of the present invention may contain one or more structural units derived from a monomer or monomers different from the compound (I) in addition to the structural unit derived from the compound (I).

In the resin having one or more structural units derived from a monomer or monomers different from the compound (I) in addition to the structural unit derived from the compound (I), the content of the structural unit derived from the compound (I) is usually 3 to 80% by mole, preferably 5 to 70% by mole and more preferably 10 to 50% by mole based on 100% by mole of all the structural units of the resin.

Examples of the monomers different from the compound (I) include a monomer having an acid-labile group and an acid-stable monomer having no acid-labile group.

The resin can be produced according to a known polymerization method.

The resin of the present invention is preferably itself insoluble or poorly soluble in an alkali aqueous solution but becomes soluble in an alkali aqueous solution by the action of an acid.

In this specification, "an acid-labile group" means a group capable of being eliminated by the action of an acid.

In the present specification, "ester group" means "a structure having ester of carboxylic acid". Specifically, "tert-butyl ester group" is "a structure having tert-butyl ester of carboxylic acid", and may be described as "—COOC(CH$_3$)$_3$".

Examples of the acid-labile group include a structure having ester of carboxylic acid such as an alkyl ester group in which a carbon atom adjacent to the oxygen atom is quaternary carbon atom, an alicyclic ester group in which a carbon atom adjacent to the oxygen atom is quaternary carbon atom, and a lactone ester group in which a carbon atom adjacent to the oxygen atom is quaternary carbon atom. The "quaternary carbon atom" means a "carbon atom joined to four substituents other than hydrogen atom".

Examples of the acid-labile group include a group represented by the formula (10):

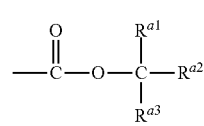

(10)

wherein $R^{a1}$, $R^{a2}$ and $R^{a3}$ independently represent a C1-C8 aliphatic hydrocarbon group or a C3-C20 saturated cyclic hydrocarbon group, and $R^{a1}$ and $R^{a2}$ can be bonded each other to form a C3-C20 ring together with the carbon atom to which they are bonded.

Examples of the C1-C8 aliphatic hydrocarbon group include a C1-C8 alkyl group. Specific examples of the C1-C8 alkyl group include a methyl group, an ethyl group, a propyl group, an isopropyl group, a butyl group, a pentyl group, a hexyl group, a heptyl group and an octyl group. The C3-C20 saturated cyclic hydrocarbon group may be monocyclic or polycyclic, and examples thereof include a monocyclic alicyclic hydrocarbon group such as a C3-C20 cycloalkyl group (e.g. a cyclopentyl group, a cyclohexyl group, a methylcyclohexyl group, a dimethylcyclohexyl group, a cycloheptyl group and a cyclooctyl group) and a polycyclic alicyclic hydrocarbon group such as a decahydronaphthyl group, an adamantyl group, a norbornyl group, a methylnorbornyl group, and the following:

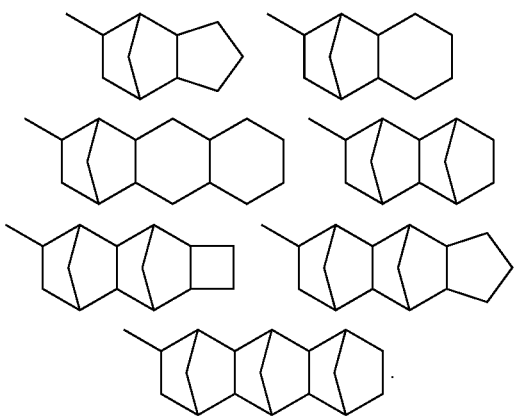

The saturated cyclic hydrocarbon group preferably has 5 to 16 carbon atoms.

Examples of the ring formed by bonding $R^{a1}$ and $R^{a2}$ each other together with the carbon atom to which they are bonded include the following groups and the ring preferably has 3 to 12 carbon atoms.

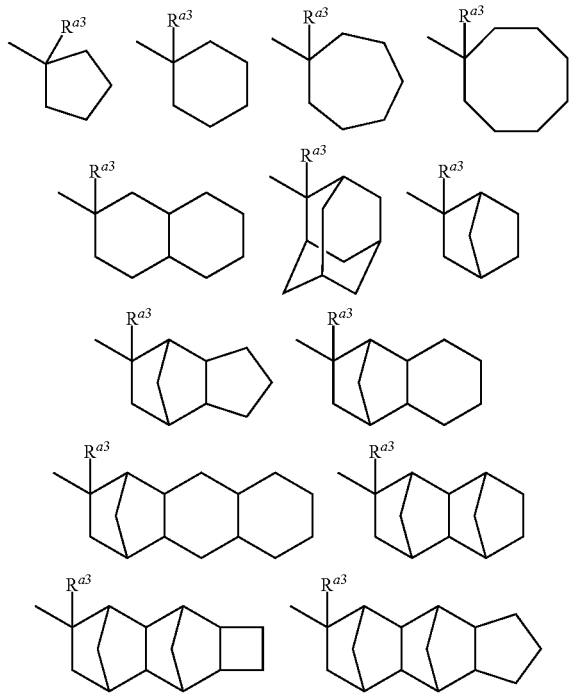

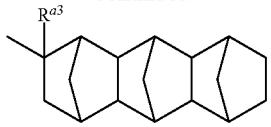

wherein $R^{a3}$ is the same as defined above.

The group represented by the formula (10) wherein $R^{a1}$, $R^{a2}$ and $R^{a3}$ independently each represent a C1-C8 alkyl group such as a tert-butyl group, the group represented by the formula (10) wherein $R^{a1}$ and $R^{a2}$ are bonded each other to form an adamantyl ring and $R^{a3}$ is a C1-C8 alkyl group such as a 2-alkyl-2-adamantyl group, and the group represented by the formula (10) wherein $R^{a1}$ and $R^{a2}$ are C1-C8 alkyl groups and $R^{a3}$ is an adamantyl group such as a 1-(1-adamantyl)-1-alkylalkoxycarbonyl group are preferable.

The monomer having an acid-labile group (hereinafter, simply referred to as the monomer (a1)) is preferably a monomer having the acid-labile group represented by the formula (10) and a carbon-carbon double bond, and more preferably an acrylate monomer having an acid-labile group represented by the formula (10) in its side chain or a methacrylate monomer having an acid-labile group represented by the formula (10) in its side chain.

Preferable examples of the monomer (a1) include a monomer having a C5-C20 saturated cyclic hydrocarbon group. When the photoresist composition contains a resin derived from a monomer having a bulky structure such as a saturated cyclic hydrocarbon group, the photoresist composition having excellent resolution tends to be obtained.

Preferable examples of the monomer (a1) include a monomer represented by the formula (a1-1) and a monomer represented by the formula (a1-2):

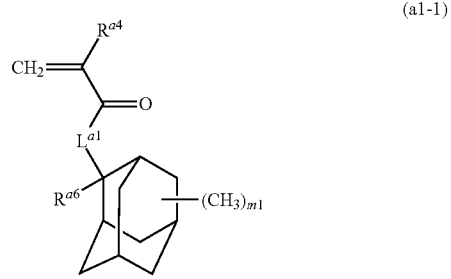

(a1-1)

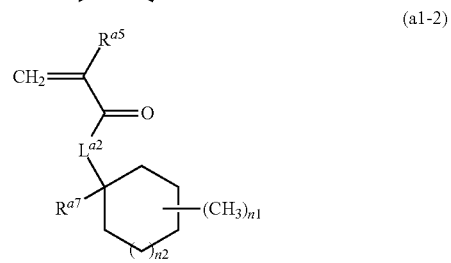

(a1-2)

wherein $R^{a4}$ and $R^{a5}$ independently represents a hydrogen atom or a methyl group, $R^{a6}$ and $R^{a7}$ independently represents a C1-C8 aliphatic hydrocarbon group or a C3-C10 saturated cyclic hydrocarbon group, $L^{a1}$ and $L^{a2}$ independently represents *—O— or *—O—$(CH_2)_{k1}$—CO—O— in which * represents a binding position to —CO—, and k1 represents an integer of 1 to 7, m1 represents an integer of 0 to 14, n1 represents an integer of 0 to 10 and n2 represents 0 or 1.

$R^{a4}$ and $R^{a5}$ are preferably methyl groups.

The aliphatic hydrocarbon group preferably has 1 to 6 carbon atoms, and the saturated cyclic hydrocarbon group preferably has 3 to 8 carbon atoms and more preferably 3 to 6 carbon atoms.

Examples of the aliphatic hydrocarbon group include a C1-C8 alkyl group such as a methyl group, an ethyl group, a propyl group, an isopropyl group, a butyl group, a tert-butyl group, a pentyl group, a hexyl group, a heptyl group and an octyl group. The saturated cyclic hydrocarbon group may be monocyclic or polycyclic. Examples of the saturated monocyclic hydrocarbon group include a cycloalkyl group such as a cyclohexyl group, a methylcyclohexyl group, a dimethylcyclohexyl group, a cycloheptyl group, a methylcycloheptyl group, and examples of the saturated polycyclic hydrocarbon group include a decahydronaphthyl group, an adamantyl group, a norbornyl group, a methylnorbornyl group and the following:

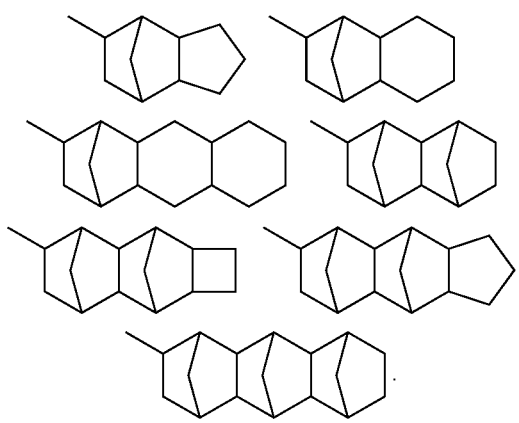

$L^{a1}$ is preferably *—O— or *—O—$(CH_2)_{f1}$—CO—O— in which * represents a binding position to —CO—, and f1 represents an integer of 1 to 4, and is more preferably *—O— or *—O—$CH_2$—CO—O—, and is especially preferably *—O—. $L^{a2}$ is preferably *—O— or *—O—$(CH_2)_{f1}$—CO—O— in which * represents a binding position to —CO—, and f1 is the same as defined above, and is more preferably *—O— or *—O—$CH_2$—CO—O—, and is especially preferably *—O—.

In the formula (a1-1), m1 is preferably an integer of 0 to 3, and is more preferably 0 or 1. In the formula (a1-2), n1 is preferably an integer of 0 to 3, and is more preferably 0 or 1.

Examples of the monomer represented by the formula (a1-1) include the following.

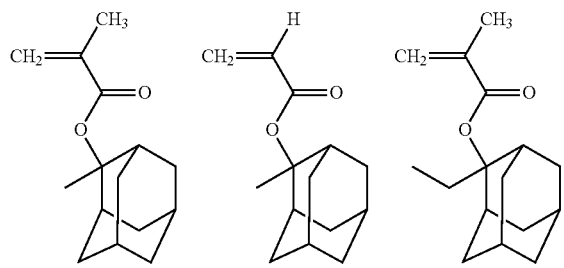

-continued

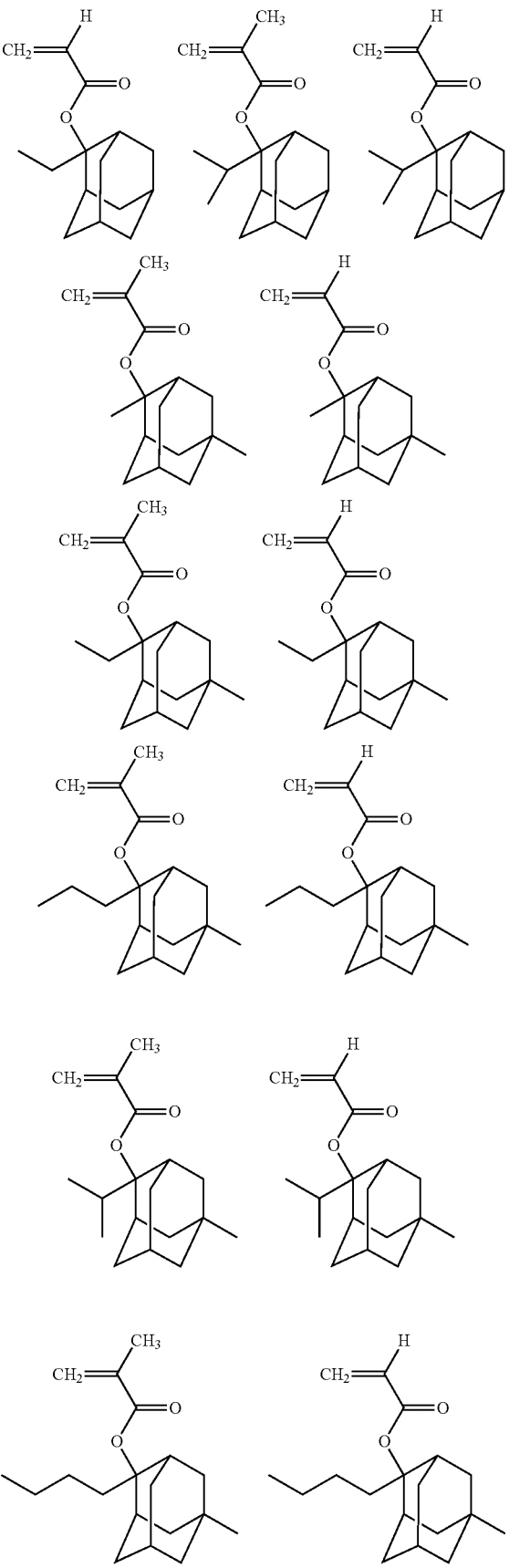

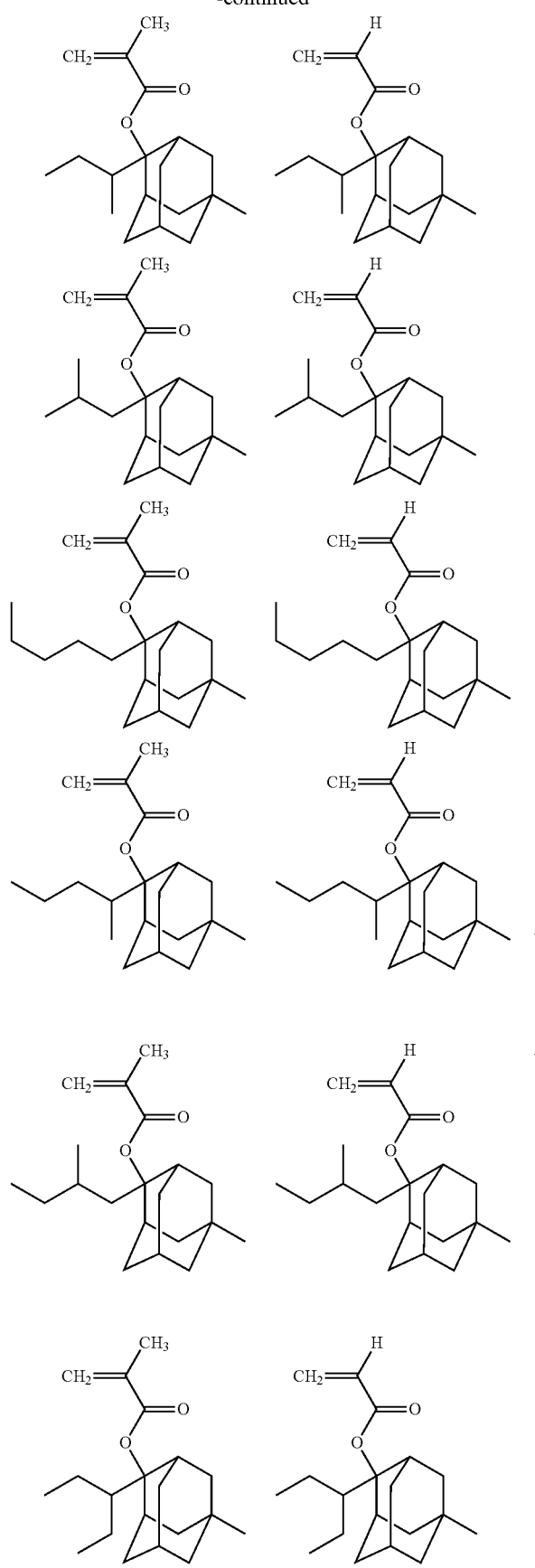
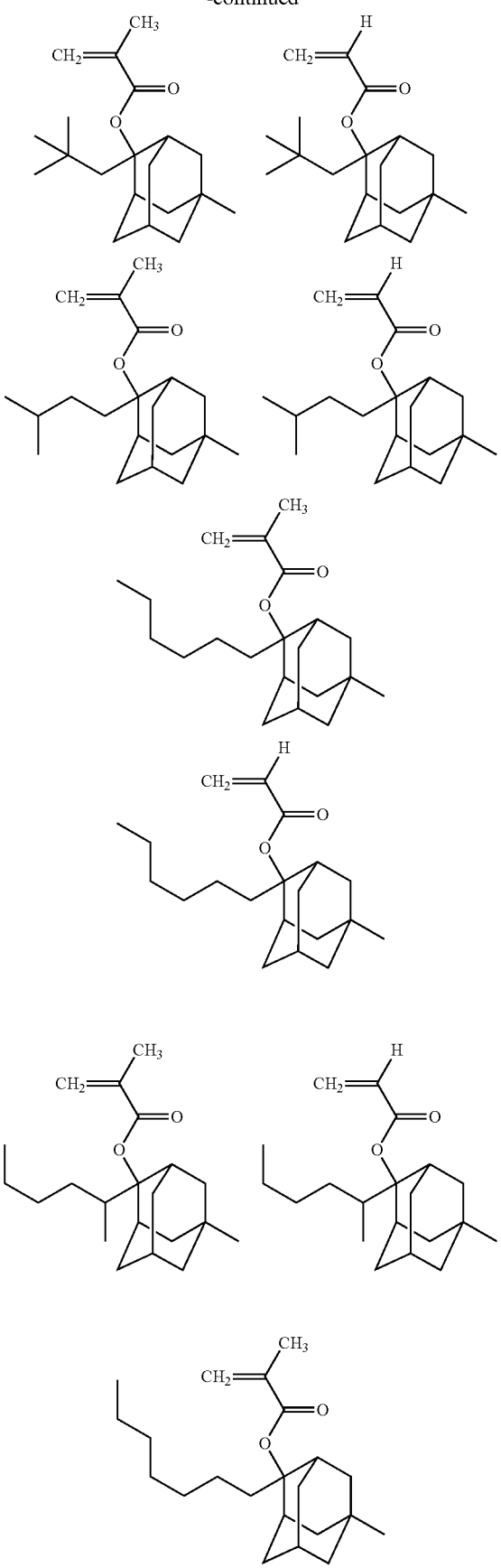

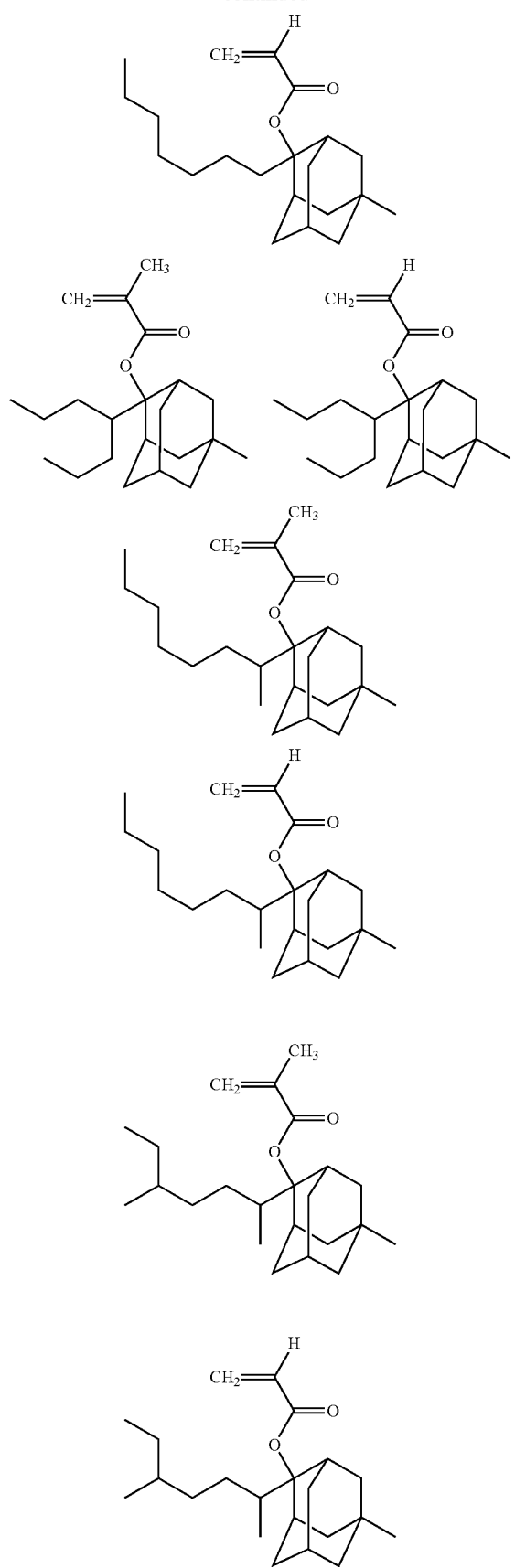
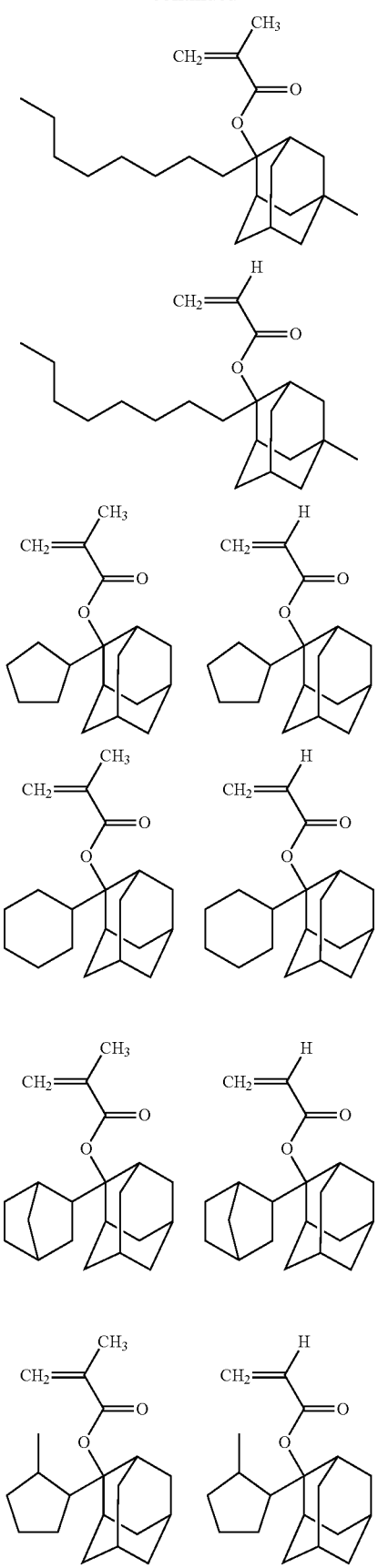

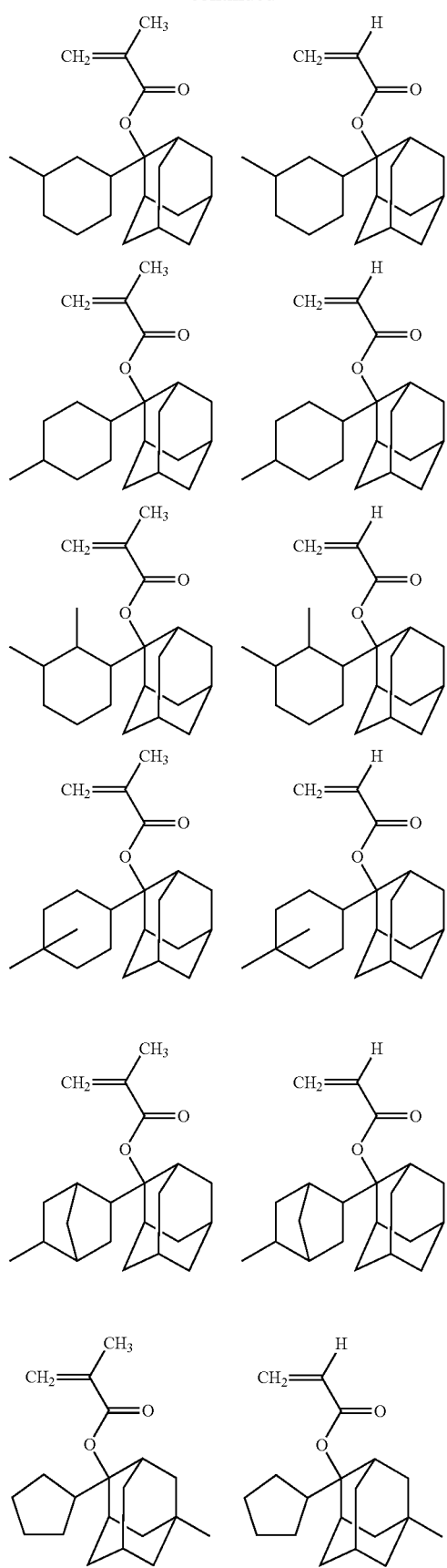
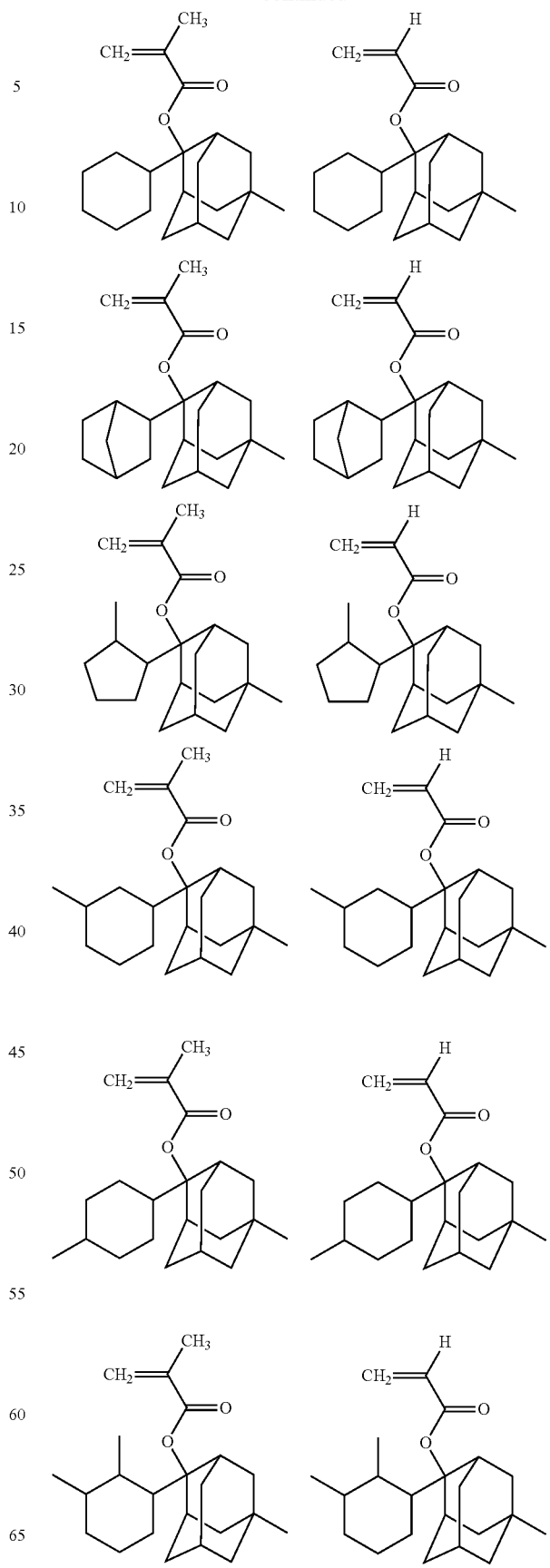

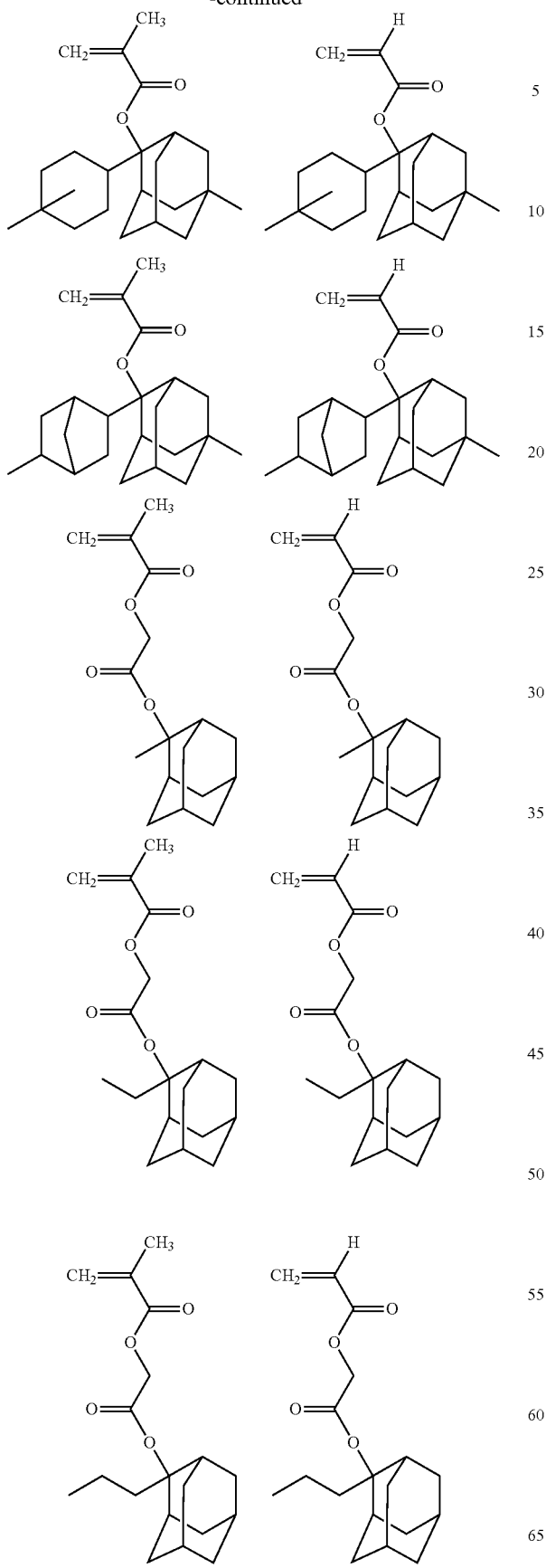

-continued
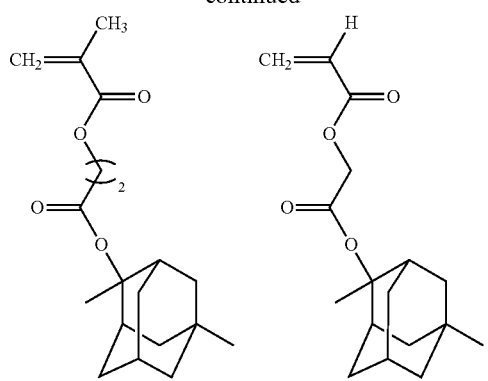
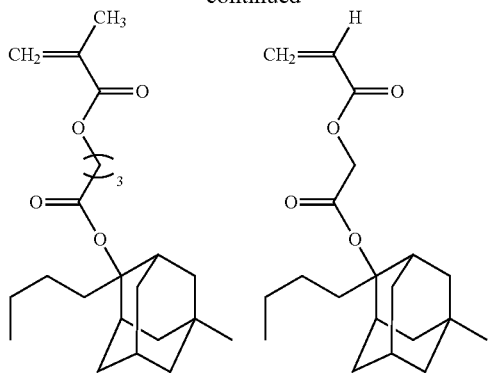
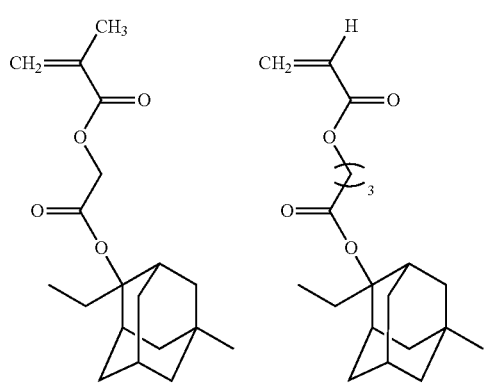
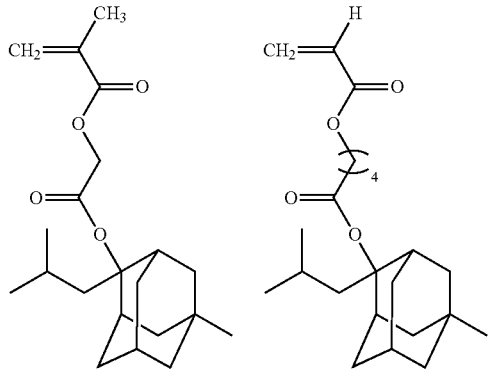
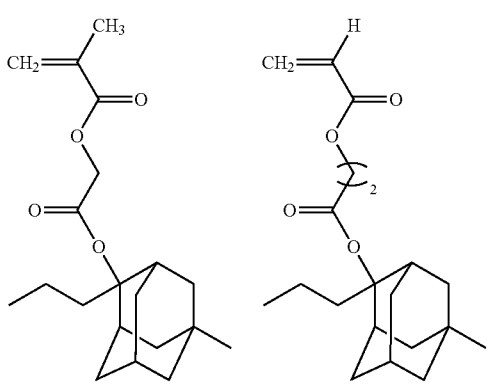
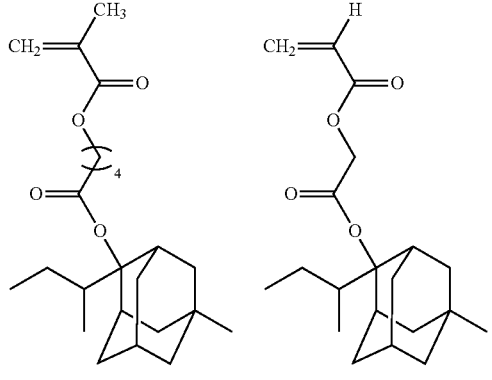
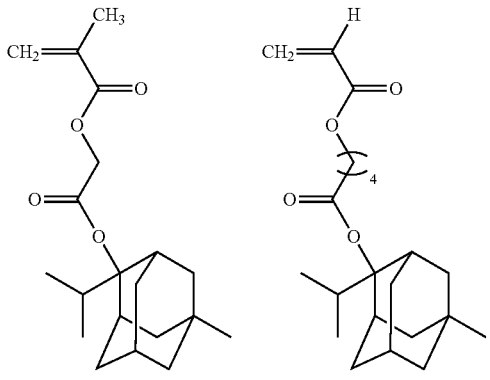
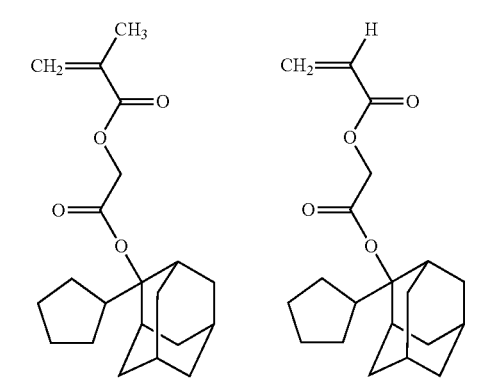

-continued
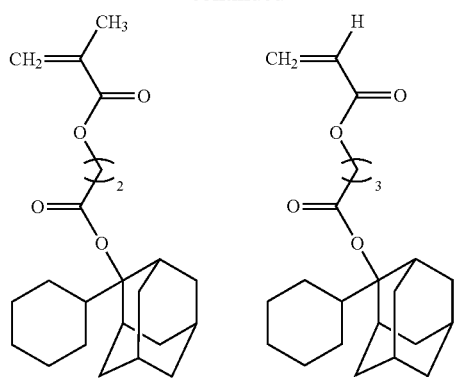
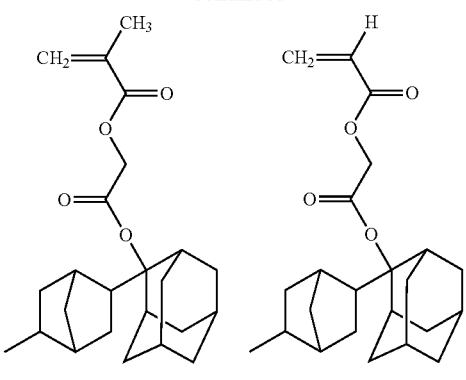
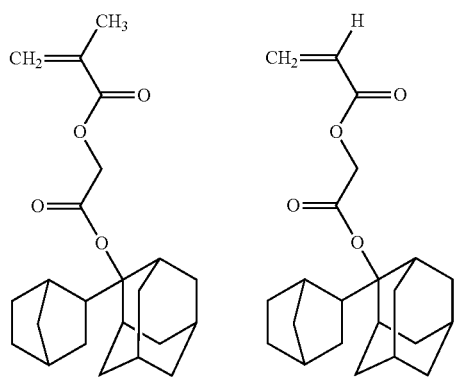
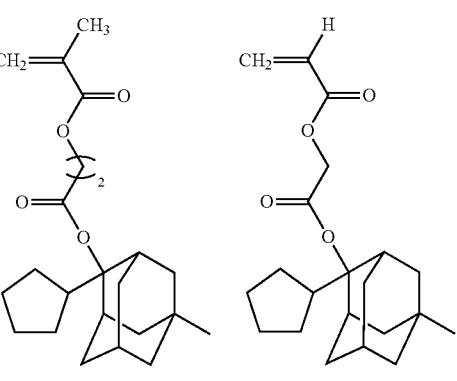
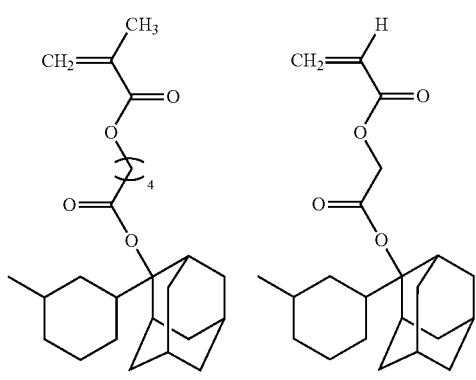
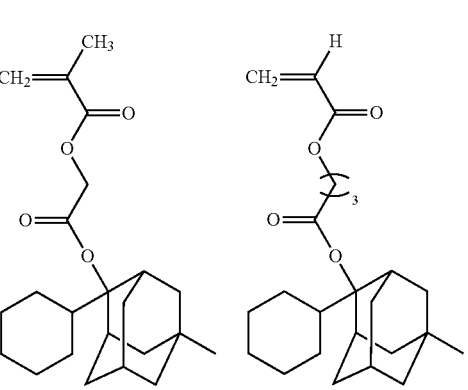
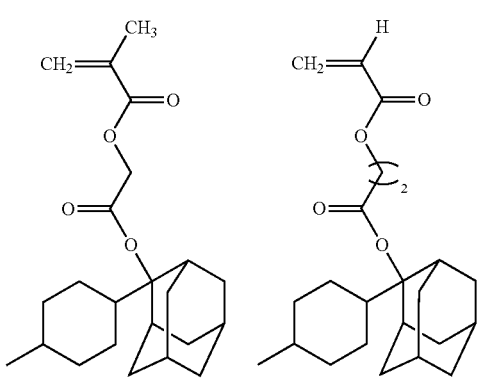
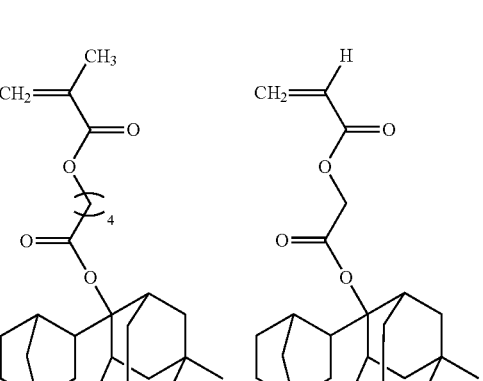

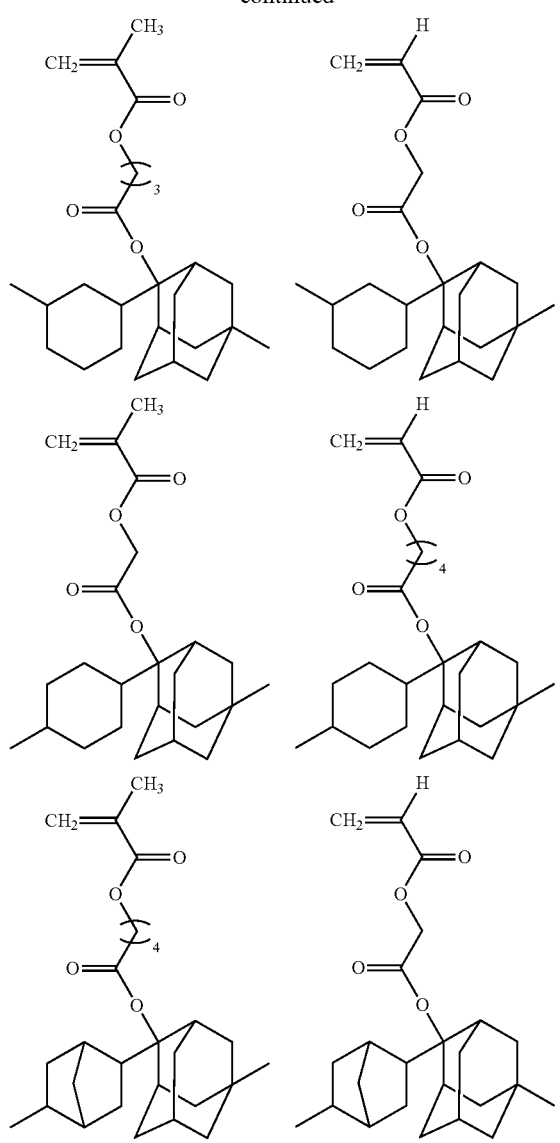
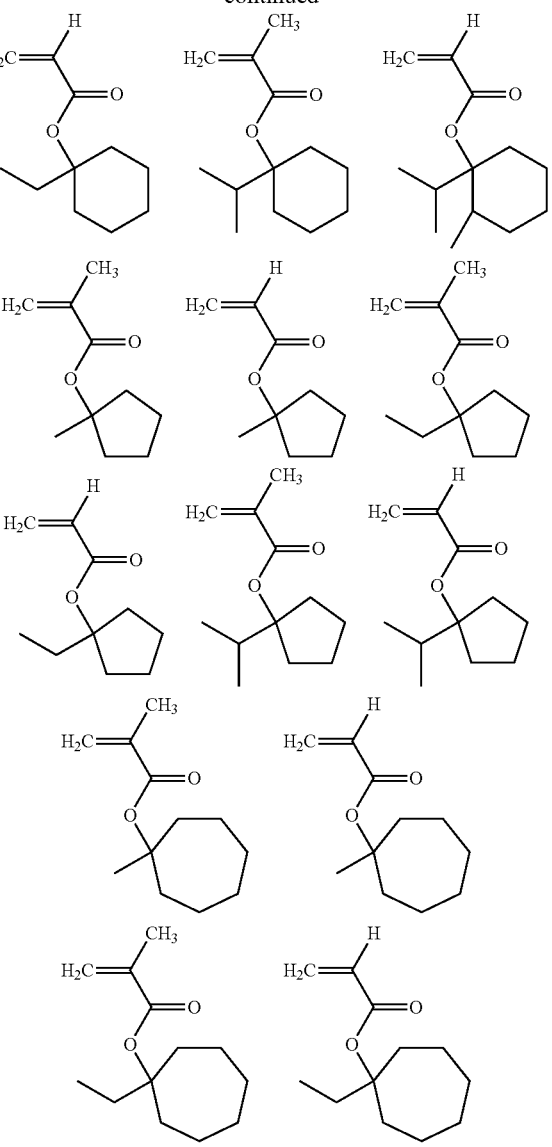

Among them, preferred are 2-methyl-2-adamantyl acrylate, 2-methyl-2-adamantyl methacrylate, 2-ethyl-2-adamantyl acrylate, 2-ethyl-2-adamantyl methacrylate, 2-isopropyl-2-adamantyl acrylate and 2-isopropyl-2-adamantyl methacrylate, and more preferred are 2-methyl-2-adamantyl methacrylate, 2-ethyl-2-adamantyl methacrylate, and 2-isopropyl-2-adamantyl methacrylate.

Examples of the monomer represented by the formula (a1-2) include the following.

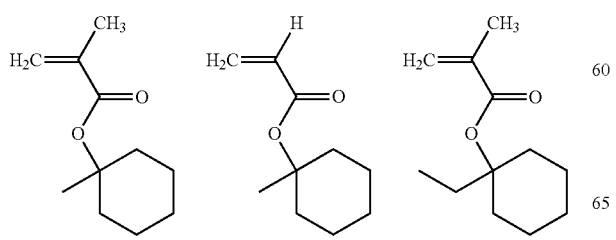
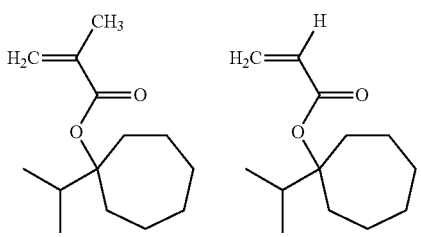
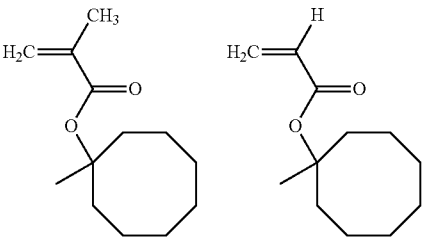

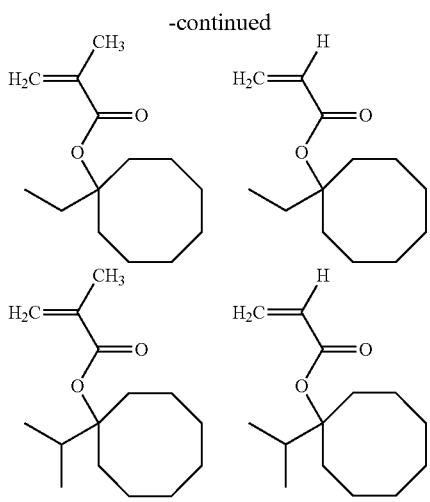

Among them, preferred are 1-ethyl-1-cyclohexyl acrylate, 1-ethyl-1-cyclohexyl methacrylate, 1-ethyl-1-cyclopentyl acrylate and 1-ethyl-1-cyclopentyl methacrylate, and more preferred are 1-ethyl-1-cyclohexyl methacrylate and 1-ethyl-1-cyclopentyl methacrylate.

The content of the structural unit derived from the monomer (a1) in the resin is usually 10 to 95% by mole, preferably 15 to 90% by mole and more preferably 20 to 85% by mole based on 100% by mole of all the structural units of the resin.

The resin can have two or more kinds of structural units derived from the monomer (a1).

Other examples of the monomer (a1) include a monomer represented by the formula (a1-3):

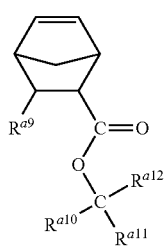

(a1-3)

wherein $R^{a9}$ represents a hydrogen atom, a C1-C3 aliphatic hydrocarbon group which can have one or more substituents, a carboxyl group, a cyano group or a —COOR$^{a13}$ group in which $R^{a13}$ represents a C1-C8 aliphatic hydrocarbon group or a C3-C8 saturated cyclic hydrocarbon group, and the C1-C8 aliphatic hydrocarbon group and the C3-C8 saturated cyclic hydrocarbon group can have one or more hydroxyl groups, and one or more —CH$_2$— in the C1-C8 aliphatic hydrocarbon group and the C3-C8 saturated cyclic hydrocarbon group can be replaced by —O— or —CO—, $R^{a10}$, $R^{a11}$ and $R^{a12}$ independently represent a C1-C12 aliphatic hydrocarbon group or a C3-C12 saturated cyclic hydrocarbon group, or $R^{a10}$ and $R^{a11}$ are bonded each other to form a ring together with the carbon atom to which $R^{a10}$ and $R^{a11}$ are bonded, and the C1-C12 aliphatic hydrocarbon group and the C3-C12 saturated cyclic hydrocarbon group can have one or more hydroxyl groups, and one or more —CH$_2$— in the C1-C12 aliphatic hydrocarbon group and the C3-C12 saturated cyclic hydrocarbon group can be replaced by —O— or —CO—.

Examples of the substituent include a hydroxyl group. Examples of the C1-C3 aliphatic hydrocarbon group which can have one or more substituents include a methyl group, an ethyl group, a propyl group, a hydroxymethyl group and a 2-hydroxyethyl group. Examples of $R^{a13}$ include a methyl group, an ethyl group, a propyl group, a 2-oxo-oxolan-3-yl group and a 2-oxo-oxolan-4-yl group. Examples of $R^{a10}$, $R^{a11}$ and $R^{a12}$ include a methyl group, an ethyl group, a cyclohexyl group, a methylcyclohexyl group, a hydroxycyclohexyl group, an oxocyclohexyl group and an adamantyl group, and examples of the ring formed by bonding $R^{a10}$ and $R^{a11}$ each other together with the carbon atom to which $R^{a10}$ and $R^{a11}$ are bonded include a cyclohexane ring and an adamantane ring.

Examples of the monomer represented by the formula (a1-3) include tert-butyl 5-norbornene-2-carboxylate, 1-cyclohexyl-1-methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 1-(4-methylcyclohexyl)-1-methylethyl 5-norbornene-2-carboxylate, 1-(4-hydroxylcyclohexyl)-1-methylethyl 5-norbornene-2-carboxylate, 1-methyl-1-(4-oxocyclohexyl) ethyl 5-norbornene-2-carboxylate and 1-(1-adamantyl)-1-methylethyl 5-norbornene-2-carboxylate.

When the resin contains the structural unit derived form the monomer represented by the formula (a1-3), the content of the structural unit derived from the monomer represented by the formula (a1-3) is usually 10 to 95% by mole and preferably 15 to 90% by mole and more preferably 20 to 85% by mole based on total molar of all the structural units of the resin.

Other examples of the monomer (a1) include a monomer represented by the formula (a1-4):

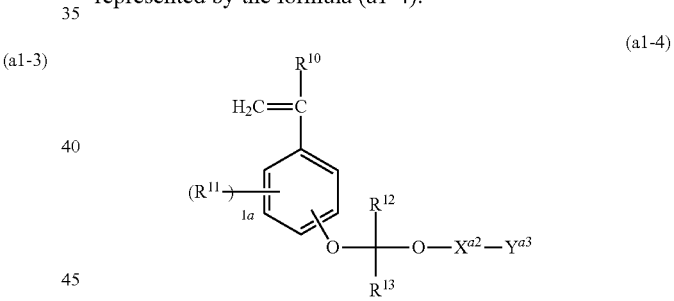

(a1-4)

wherein $R^{10}$ represents a hydrogen atom, a halogen atom, a C1-C6 alkyl group or a C1-C6 halogenated alkyl group, $R^{11}$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, 1a represents an integer of 0 to 4, $R^{12}$ and $R^{13}$ each independently represent a hydrogen atom or a C1-C12 hydrocarbon group, $X^{a2}$ represents a single bond or a C1-C17 divalent saturated hydrocarbon group in which one or more —CH$_2$— can be replaced by —O—, —CO—, —S—, —SO$_2$— or —N(R$^c$)— wherein $R^c$ represents a hydrogen atom or a C1-C6 alkyl group, and $Y^{a3}$ represents a C1-C12 aliphatic hydrocarbon group, a C3-C18 saturated cyclic hydrocarbon group or a C6-C18 aromatic hydrocarbon group, and the C1-C12 aliphatic hydrocarbon group, the C2-C18 saturated cyclic hydrocarbon group and the C6-C18 aromatic hydrocarbon group can have one or more substituents.

Examples of the halogen atom include a fluorine atom.
Examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferable and a C1-C2 alkyl group is more preferable and a methyl group is especially preferable.

Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group.

Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C1-C2 alkoxy group is more preferable and a methoxy group is especially preferable.

Examples of the C2-C4 acyl group include an acetyl group, a propionyl group and a butyryl group, and examples of the C2-C4 acyloxy group include an acetyloxy group, a propionyloxy group and a butyryloxy group.

Examples of the C1-C12 hydrocarbon group include a C1-C12 aliphatic hydrocarbon group such as a methyl group, an ethyl group, a propyl group, an isopropyl group, a butyl group, an isobutyl group, a sec-butyl group, a tert-butyl group, a pentyl group, a hexyl group, a heptyl group, an octyl group, a 2-ethylhexyl group, a nonyl group, a decyl group, an undecyl group and a dodecyl group, and a C3-C12 saturated cyclic hydrocarbon group such as a cyclohexyl group, an adamantyl group, a 2-alkyl-2-adamantyl group, a 1-(1-adamantyl)-1-alkyl group and an isobornyl group.

Examples of the C1-C17 divalent saturated hydrocarbon group include a C1-C17 alkanediyl group such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, a undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group.

Examples of the C1-C12 aliphatic hydrocarbon group include a methyl group, an ethyl group, a propyl group, an isopropyl group, a butyl group, an isobutyl group, a sec-butyl group, a tert-butyl group, a pentyl group, a hexyl group, a heptyl group, an octyl group, a 2-ethylhexyl group, a nonyl group, a decyl group, an undecyl group and a dodecyl group. Examples of the C3-C18 saturated cyclic hydrocarbon group include a cyclopropyl group, a cyclobutyl group, a cyclopentyl group, a cyclohexyl group, a cycloheptyl group, a cyclooctyl group, a cyclononyl group, a cyclodecyl group, a norbornyl group, a 1-adamantyl group, a 2-adamantyl group, an isobornyl group and the following groups:

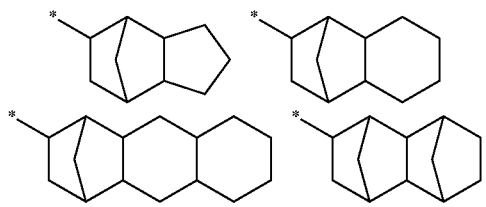

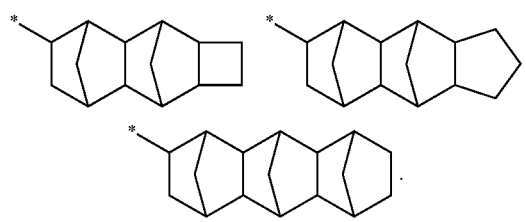

Examples of the C6-C18 aromatic hydrocarbon group include a phenyl group, a naphthyl group, an anthryl group, a p-methylphenyl group, a p-tert-butylphenyl group and a p-adamantylphenyl group.

Examples of the monomer represented by the formula (a1-4) include the followings.

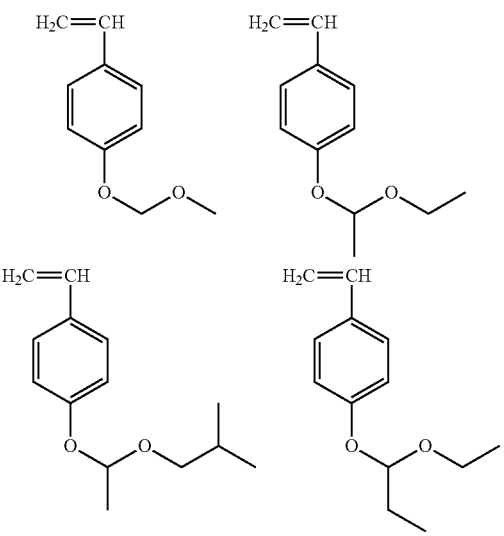

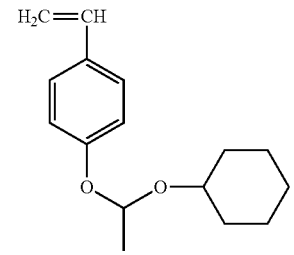

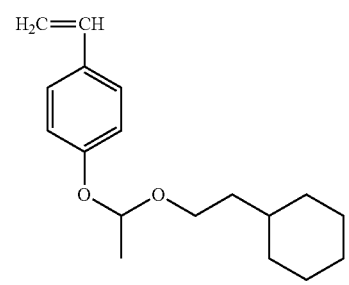

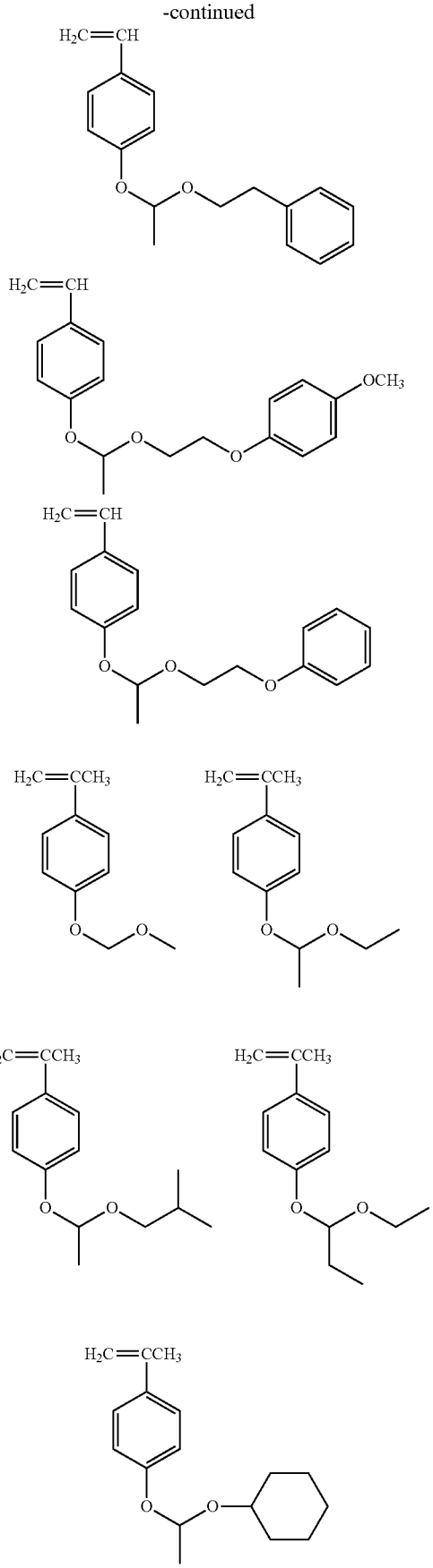

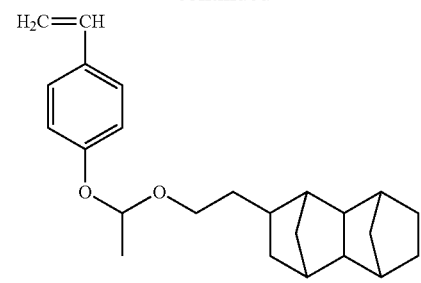
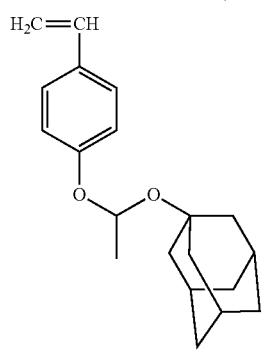
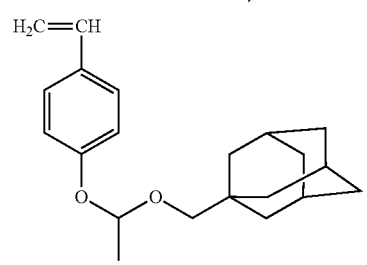
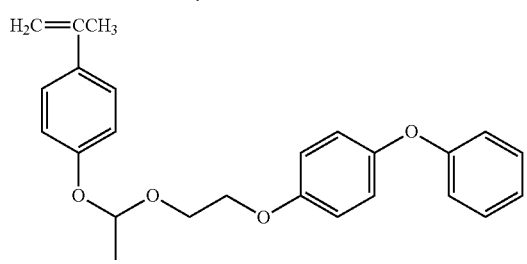
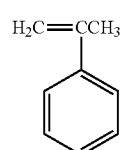
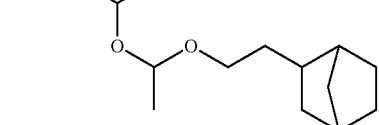
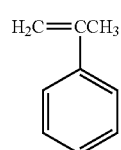
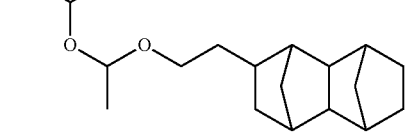
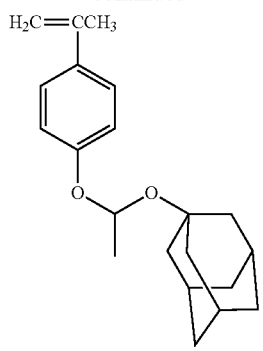
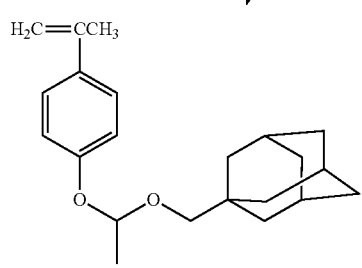
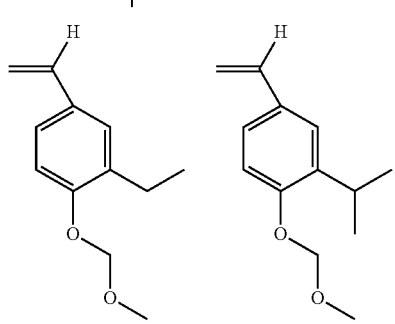
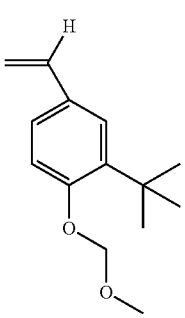
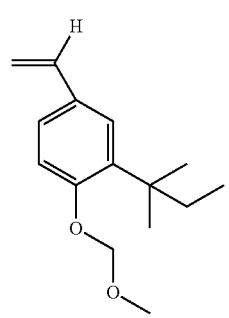
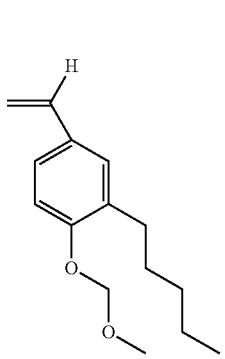
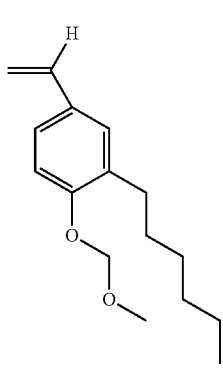

-continued
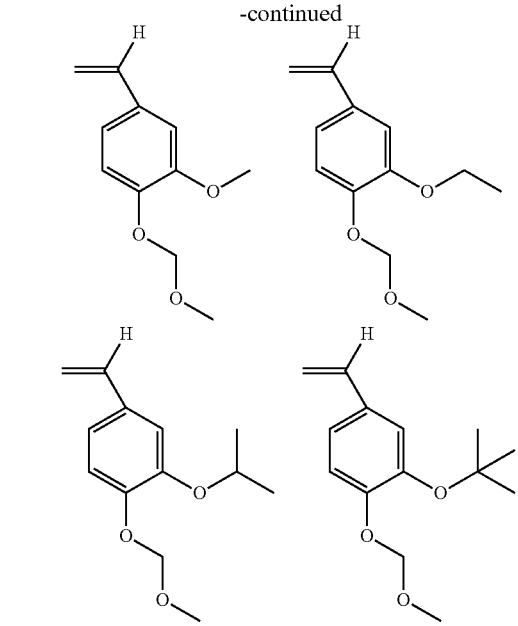
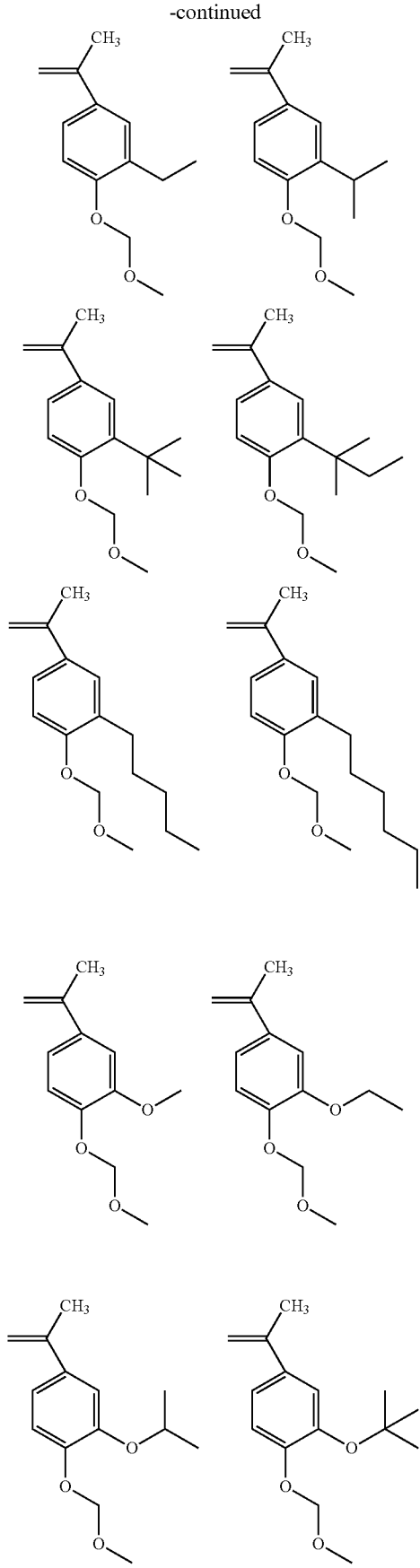

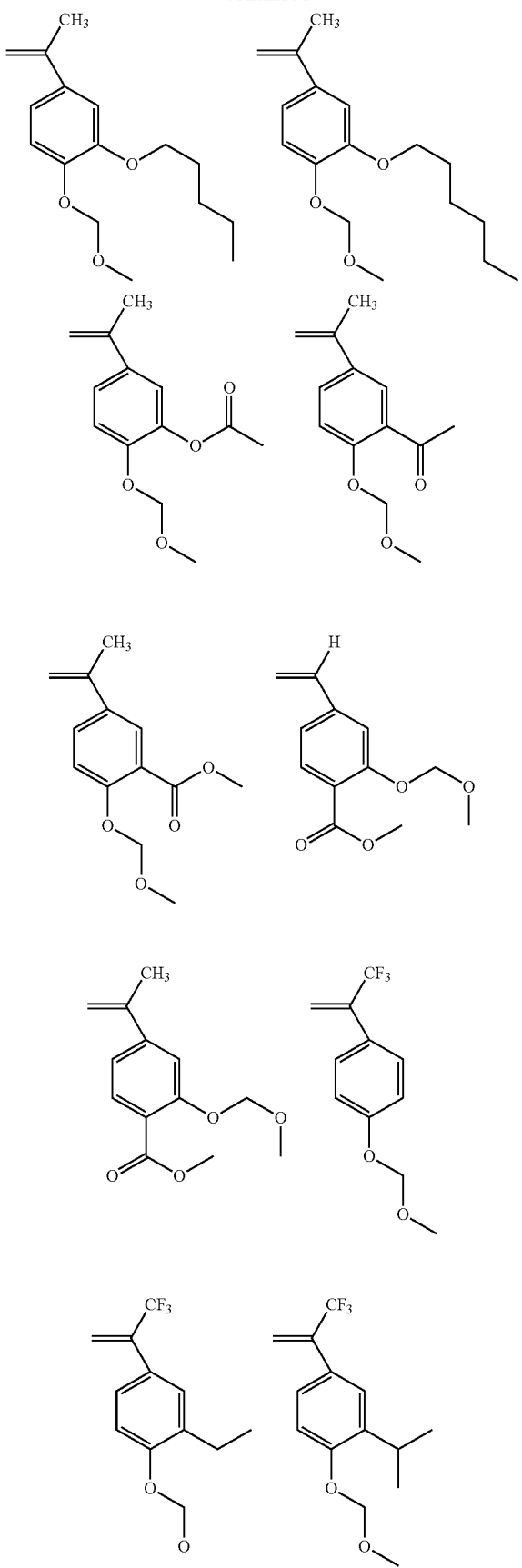
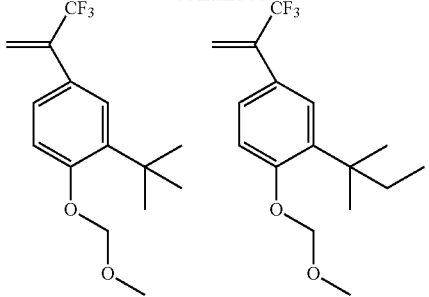

When the resin contains the structural unit derived form the monomer represented by the formula (a1-4), the content of the structural unit derived from the monomer represented by the formula (a1-4) is usually 10 to 95% by mole and preferably 15 to 90% by mole and more preferably 20 to 85% by mole based on total molar of all the structural units of the resin.

The resin of the present invention preferably contains one or more structural units derived from the compound (I), one or more structural units derived from the monomer (a1) and one or more structural units derived from a monomer having no acid-labile group. The resin can have two or more kinds of structural units derived from the monomers having no acid-labile group. When the resin contains one or more structural units derived from the monomer (a1) and one or more structural units derived from a monomer having no acid-labile group, the content of the structural unit derived from the monomer (a1) is usually 10 to 80% by mole and preferably 20 to 60% by mole based on 100% by mole of all the structural units of the resin. The content of the structural unit derived from the monomer (a1) having an adamantyl group, especially the monomer represented by the formula (a1-1) in the structural unit derived from the monomer (a1), is preferably 15% by mole or more from the viewpoint of dry-etching resistance of the photoresist composition.

The resin preferably contains the structural unit derived from the acid-stable monomer having no acid-labile group.

The acid-stable monomer having no acid-labile group preferably contains one or more hydroxyl groups or a lactone ring. When the resin contains the structural unit derived from the acid-stable monomer having no acid-labile group and having one or more hydroxyl groups or a lactone ring, a photoresist composition having good resolution and adhesiveness of photoresist to a substrate tends to be obtained. Hereinafter, the acid-stable monomer having no acid-labile group and having one or more hydroxyl groups is simply referred to as the monomer (a2) and the acid-stable monomer having no acid-labile group and having a lactone ring is simply referred to as the monomer (a3).

When the photoresist composition of the present invention is used for KrF excimer laser (wavelength: 248 nm) lithography, EUV lithography and EB lithography, the resin of the present invention preferably contains a structural unit derived from the acid-stable monomer having no acid-labile group and having one or more phenolic hydroxyl groups. The resin can have two or more kinds of the structural unit derived from the acid-stable monomer having no acid-labile group and having one or more phenolic hydroxyl groups. Examples of the acid-stable monomer having no acid-labile group and having one or more phenolic hydroxyl groups include a monomer represented by the formula (a2-0):

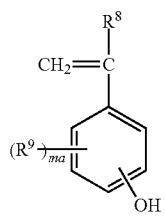
(a2-0)

wherein $R^8$ represents a hydrogen atom, a halogen atom, a C1-C6 alkyl group or a C1-C6 halogenated alkyl group, $R^9$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, ma represents an integer of 0 to 4.

In the formula (a2-0), examples of the halogen atom include a fluorine atom. Examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferable and a C1-C2 alkyl group is more preferable and a methyl group is especially preferable. Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C1-C2 alkoxy group is more preferable and a methoxy group is especially preferable. Examples of the C2-C4 acyl group include an acetyl group, a propionyl group and a butyryl group, and examples of the C2-C4 acyloxy group include an acetyloxy group, a propionyloxy group and a butyryloxy group. In the formula (a2-0), ma is preferably 0, 1 or 2, and is more preferably 0 or 1, and especially preferably 0.

The resin containing the structural unit derived from the monomer represented by the formula (a2-0) can be produced, for example, by polymerizing a monomer obtained by protecting a hydroxyl group of the monomer represented by the formula (a2-0) with an acetyl group with other monomers followed by conducting deacetylation of the obtained polymer with a base.

Examples of the monomer represented by the formula (a2-0) include the followings.

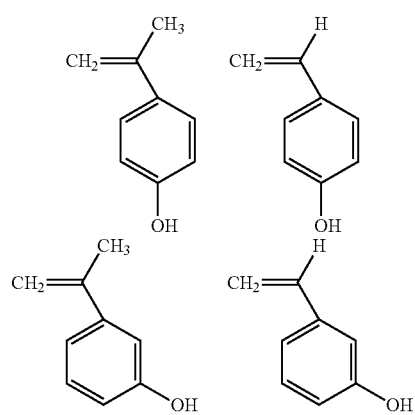

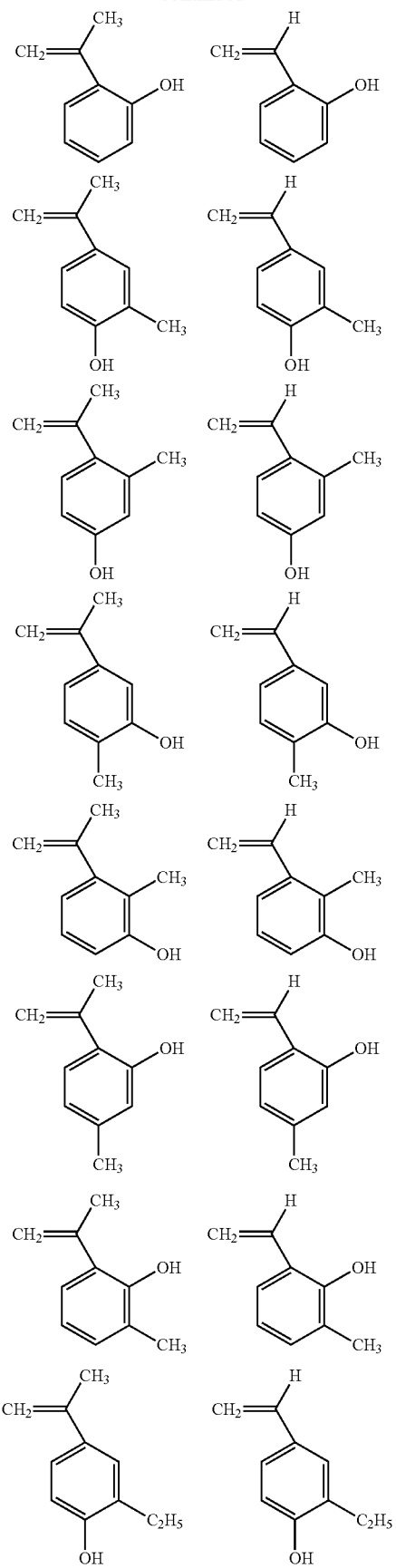

-continued

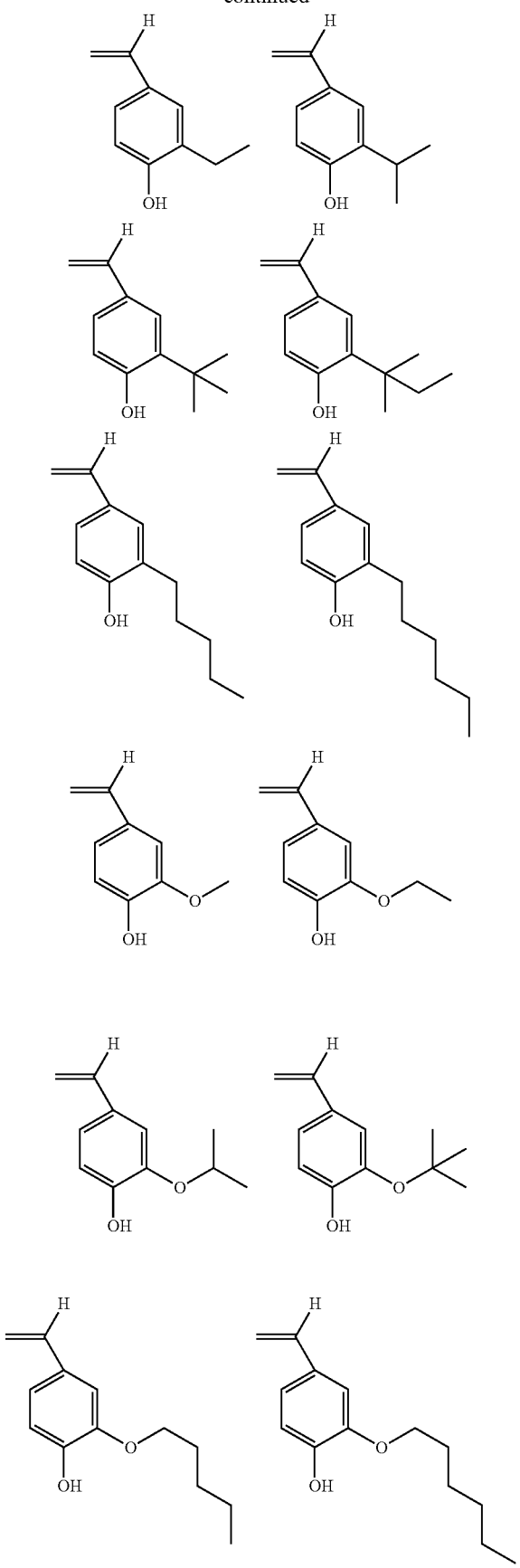
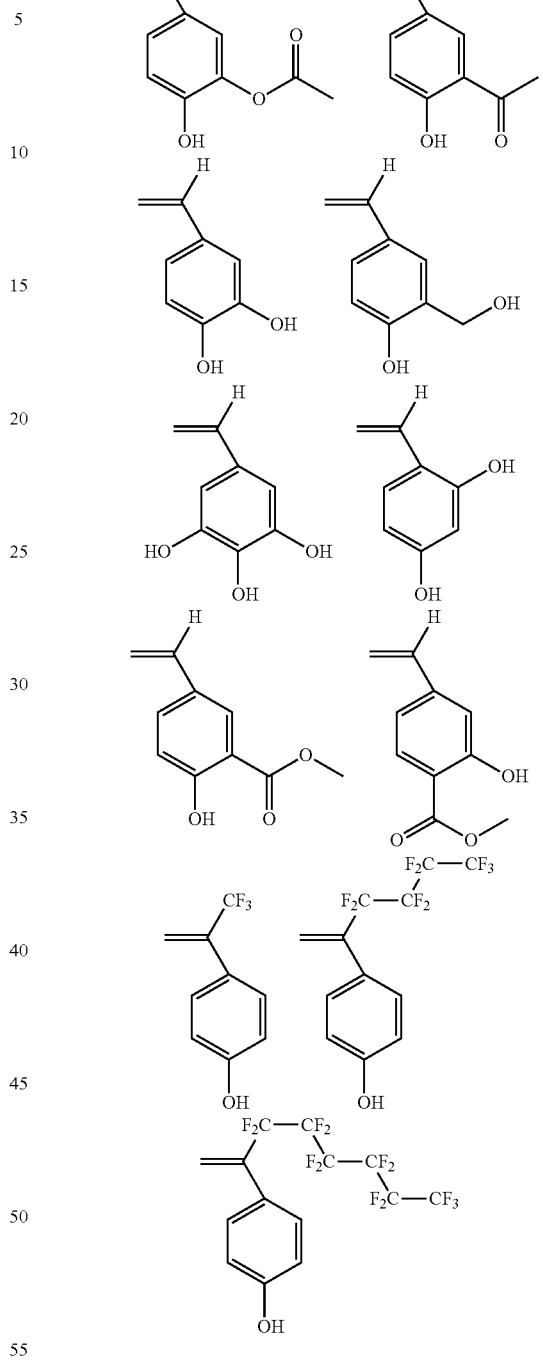

Among them, preferred are 4-hydroxystyrene and 4-hydroxy-α-methylstyrene.

When the resin contains the structural unit derived from the monomer represented by the formula (a2-0), the content of the structural unit derived from the monomer represented by the formula (a2-0) is usually 5 to 90% by mole and preferably 10 to 85% by mole and more preferably 15 to 80% by mole based on total molar of all the structural units of the resin.

When the photoresist composition of the present invention is used for ArF excimer laser (wavelength: 193 nm) lithography, the resin of the present invention preferably contains a structural unit derived from the monomer represented by the formula (a2-1):

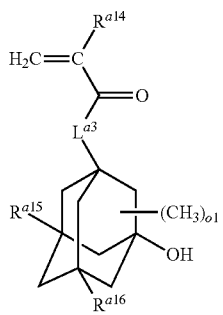

(a2-1)

wherein $R^{a14}$ represents a hydrogen atom or a methyl group, $R^{a15}$ and $R^{a16}$ independently represent a hydrogen atom, a methyl group or a hydroxyl group, $L^{a3}$ represents *—O— or *—O—$(CH_2)_{k2}$—CO—O— in which * represents a binding position to —CO—, and k2 represents an integer of 1 to 7, and of represents an integer of 0 to 10.

In the formula (a2-1) $R^{a14}$ is preferably a methyl group, $R^{a15}$ is preferably a hydrogen atom, $R^{a16}$ is preferably a hydrogen atom or a hydroxyl group, $L^{a3}$ is preferably *—O— or *—O—$(CH_2)_{f1}$—CO—O— in which * represents a binding position to —CO— and f1 represents an integer of 1 to 4, and is more preferably *—O—, and o1 is preferably 0, 1, 2 or 3 and is more preferably 0 or 1.

Examples of the monomer represented by the formula (a2-1) include the followings:

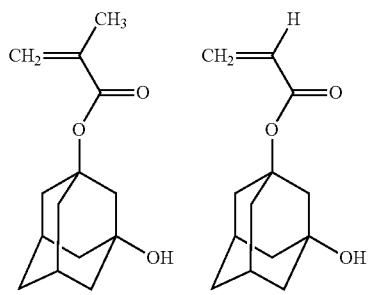

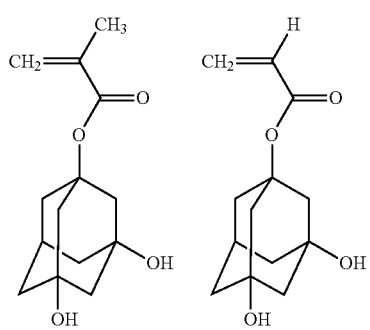

-continued

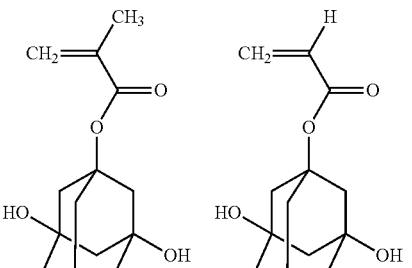

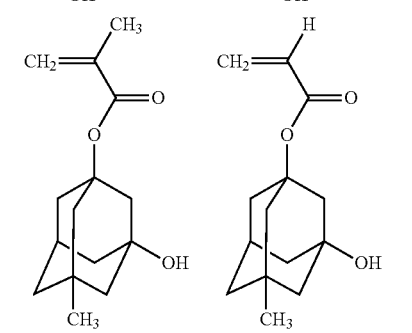

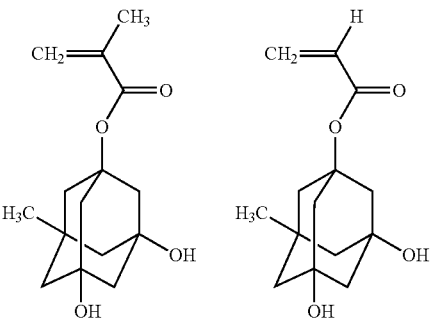

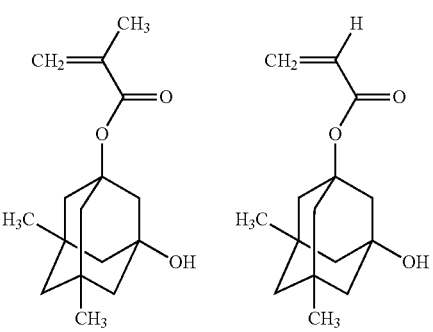

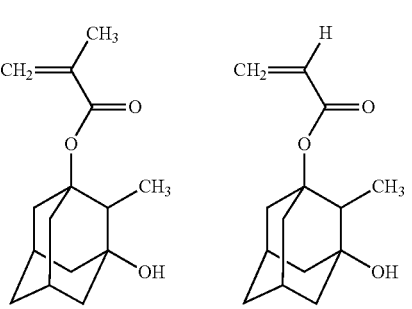

-continued
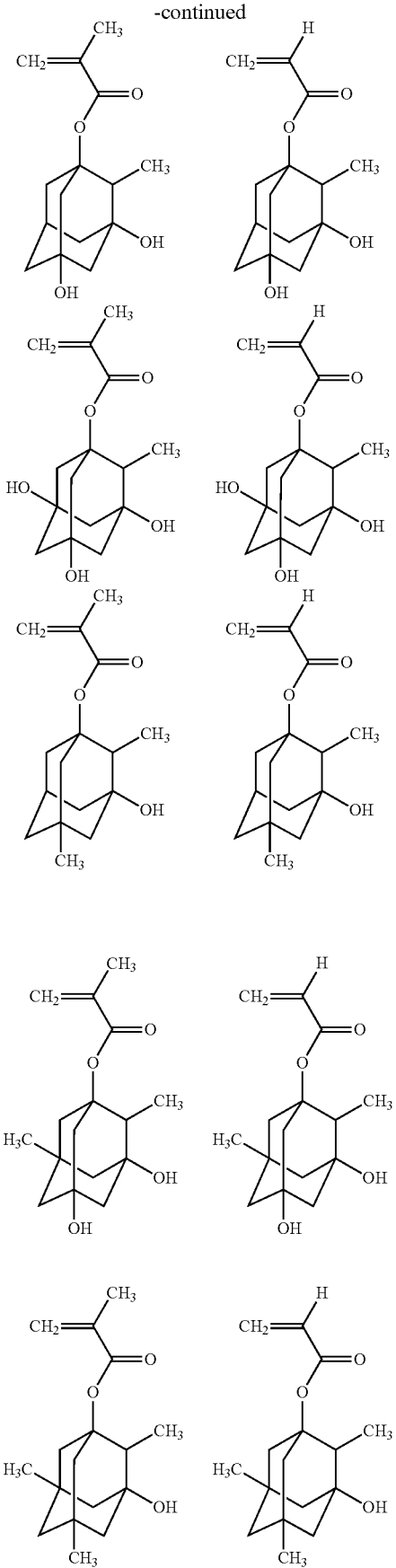
-continued
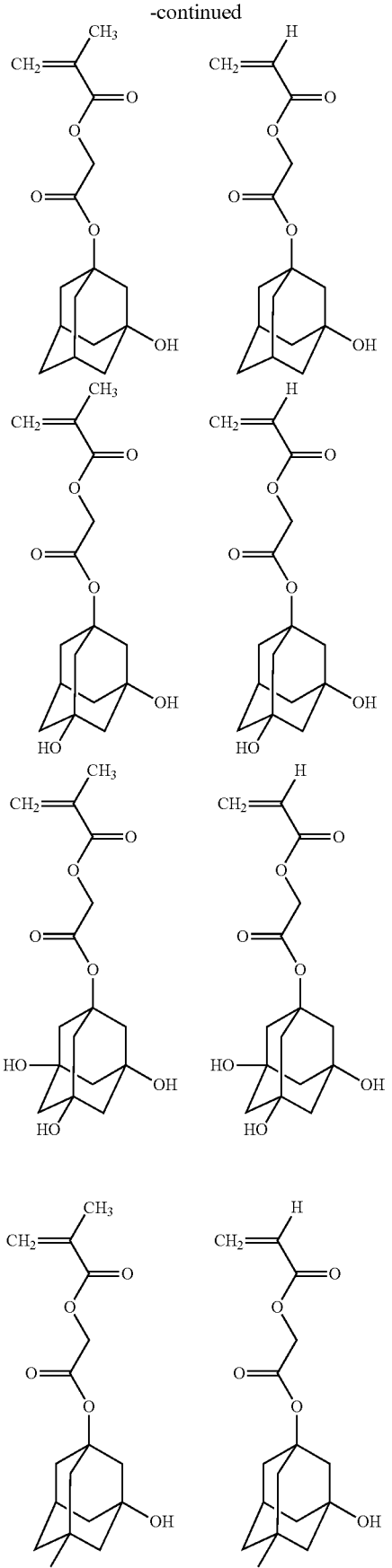

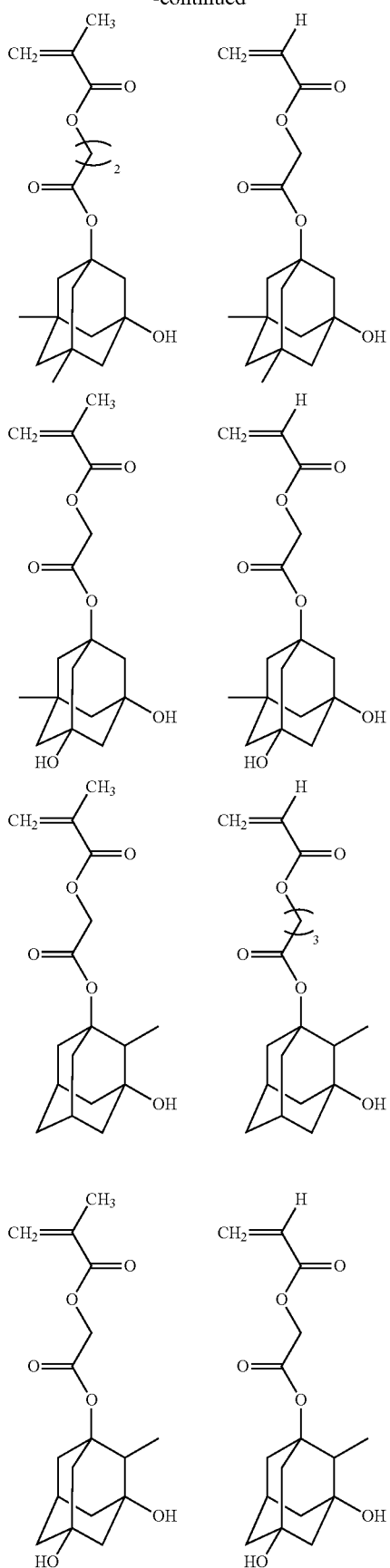

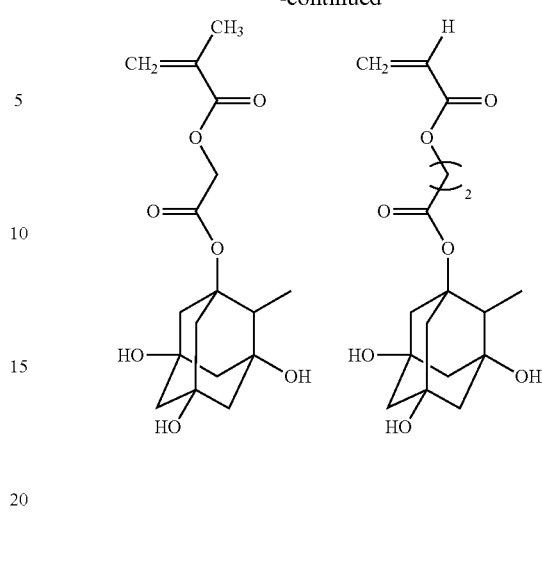

Among them, preferred are 3-hydroxy-1-adamantyl acrylate, 3-hydroxy-1-adamantyl methacrylate, 3,5-dihydroxy-1-adamantyl acrylate, 3,5-dihydroxy-1-adamantyl methacrylate, 1-(3,5-dihydroxy-1-adamantyloxycarbonyl)methyl acrylate and 1-(3,5-dihydroxy-1-adamantyloxycarbonyl)methyl methacrylate, and more preferred are 3-hydroxy-1-adamantyl methacrylate and 3,5-dihydroxy-1-adamantyl methacrylate.

When the resin of the present invention contains the structural unit derived from the monomer represented by the formula (a2-1), the content of the structural unit derived from the monomer represented by the formula (a2-1) is usually 3 to 40% by mole and preferably 5 to 35% by mole and more preferably 5 to 30% by mole based on total molar of all the structural units of the resin.

Examples of the lactone ring of the acid-stable monomer having a lactone ring and no acid-labile group include a monocyclic lactone ring such as β-propiolactone ring, γ-butyrolactone ring and γ-valerolactone ring, and a condensed ring formed from a monocyclic lactone ring and the other ring. Among them, preferred are γ-butyrolactone ring and a condensed lactone ring formed from γ-butyrolactone ring and the other ring.

Preferable examples of the acid-stable monomer having a lactone ring and no acid-labile group include the monomers represented by the formulae (a3-1), (a3-2) and (a3-3):

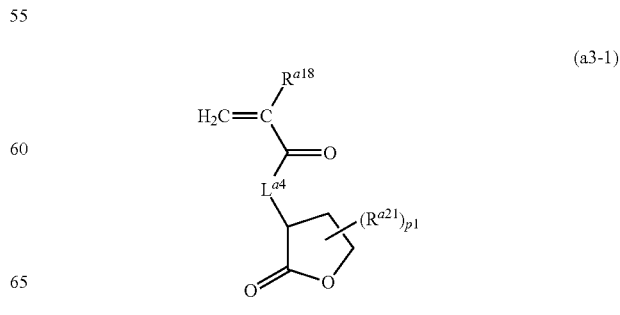

(a3-1)

(a3-2)

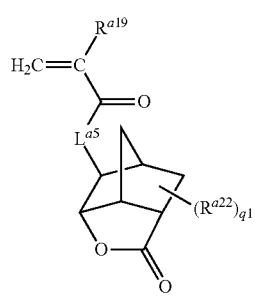

(a3-3)

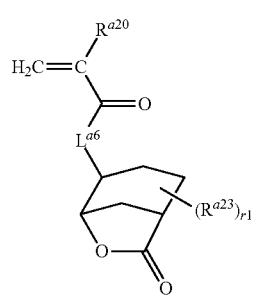

wherein $L^{a4}$, $L^{a5}$ and $L^{a6}$ independently represent *—O— or *—O—$(CH_2)_{k3}$—CO—O— in which * represents a binding position to —CO— and k3 represents an integer of 1 to 7, $R^{a18}$, $R^{a19}$ and $R^{a20}$ independently represent a hydrogen atom or a methyl group, $R^{a21}$ represents a C1-C4 aliphatic hydrocarbon group, $R^{a22}$ and $R^{a23}$ are independently in each occurrence a carboxyl group, a cyano group or a C1-C4 aliphatic hydrocarbon group, and p1 represents an integer of 0 to 5, q1 and r1 independently represent an integer of 0 to 3.

Examples of $L^{a4}$, $L^{a5}$ and $L^{a6}$ include the same as described in $L^{a3}$. It is preferred that $L^{a4}$, $L^{a5}$ and $L^{a6}$ each independently represent *—O— or *—O—$(CH_2)_{d1}$—CO—O— in which * represents a binding position to —CO— and d1 represents an integer of 1 to 4, and it is more preferred that $L^{a4}$, $L^{a5}$ and $L^{a6}$ are *—O—. $R^{a18}$, $R^{a19}$ and $R^{a20}$ are preferably methyl groups. $R^{a21}$ is preferably a methyl group. It is preferred that $R^{a22}$ and $R^{a23}$ are independently in each occurrence a carboxyl group, a cyano group or a methyl group. It is preferred that p1 is an integer of 0 to 2, and it is more preferred that p1 is 0 or 1. It is preferred that q1 and r1 independently each represent an integer of 0 to 2, and it is more preferred that q1 and r1 independently represent 0 or 1.

Examples of the monomer represented by the formula (a3-1) include the followings.

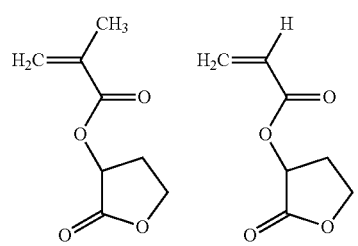

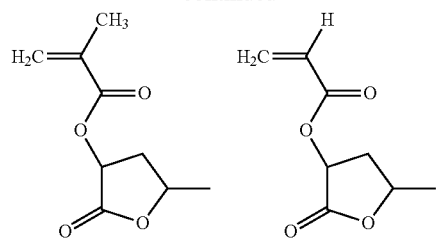

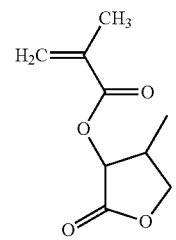

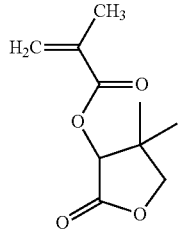

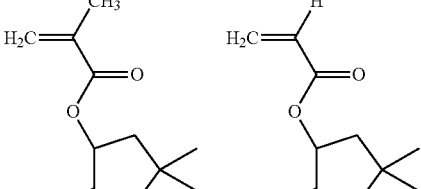

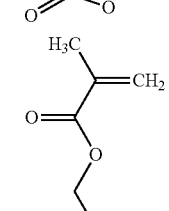

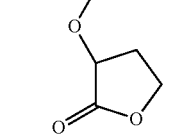

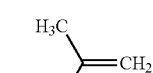 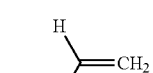

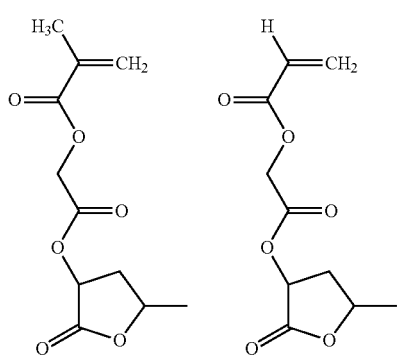

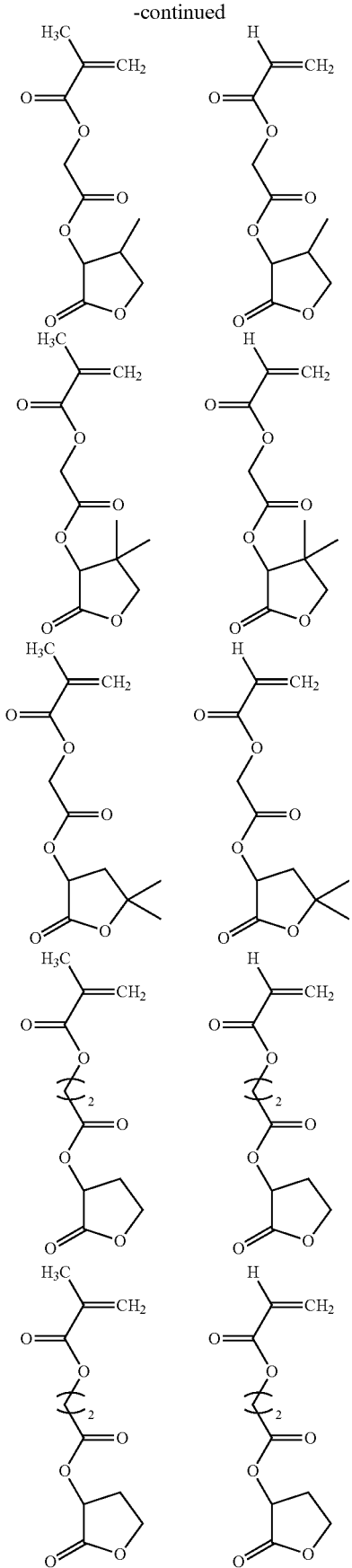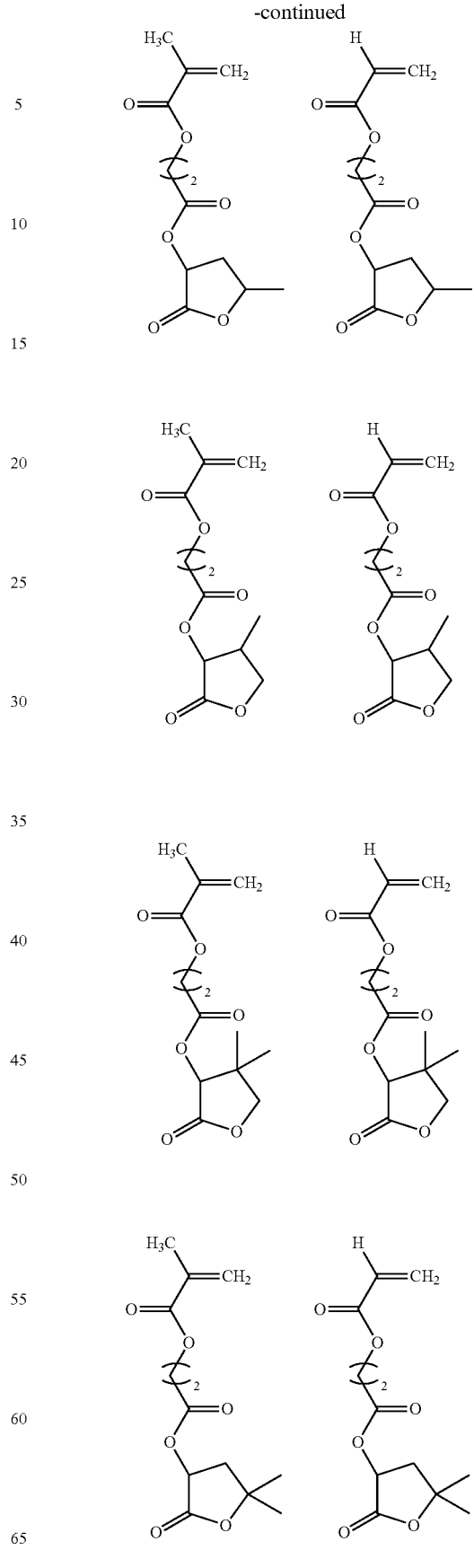

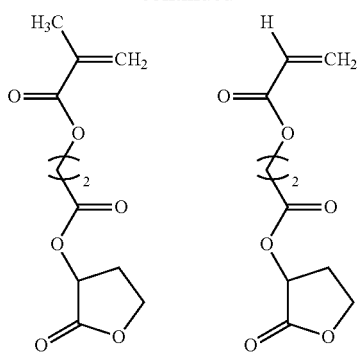
While the following monomer is an acid-labile monomer having a lactone ring, the resin can contain the structural unit derived from the following monomer.
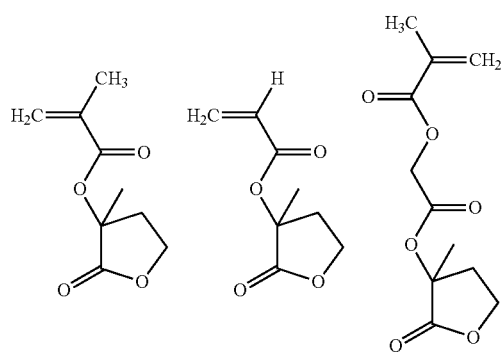
Examples of the monomer represented by the formula (a3-2) include the followings.
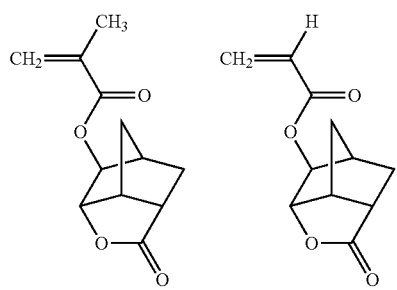
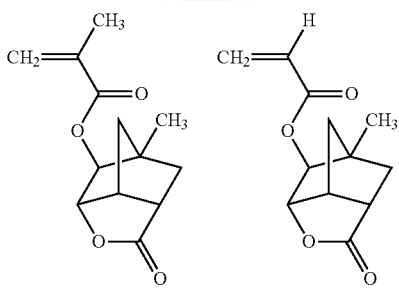
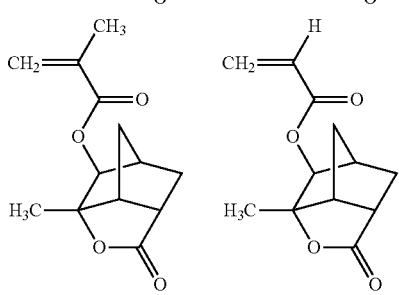
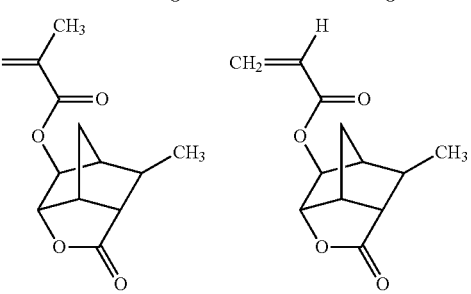
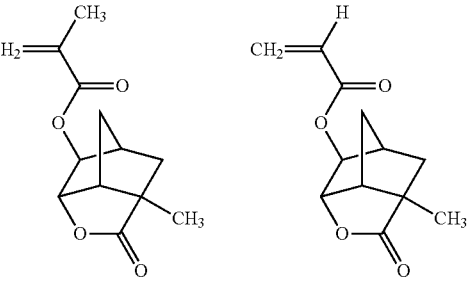
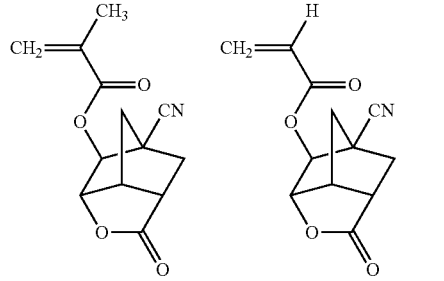
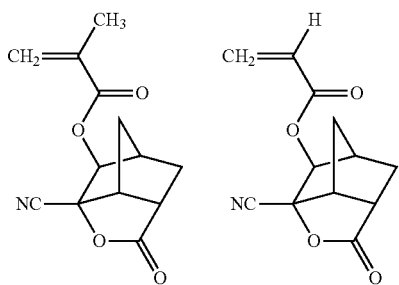

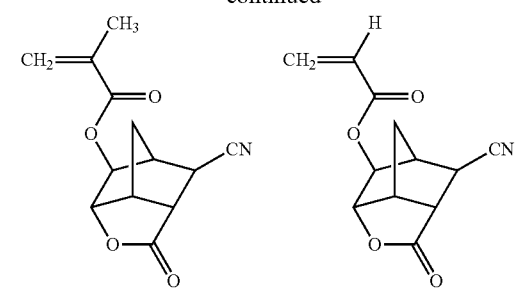
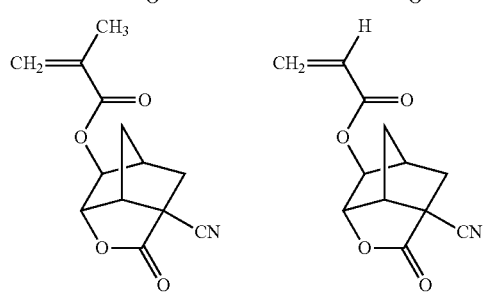
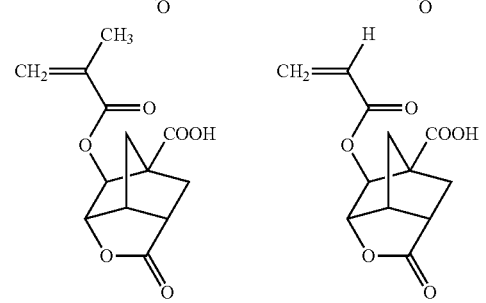
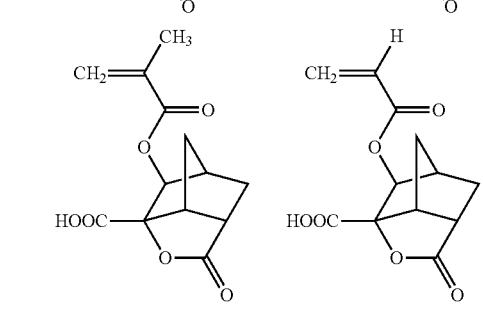
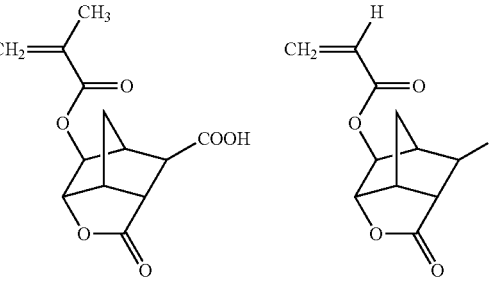
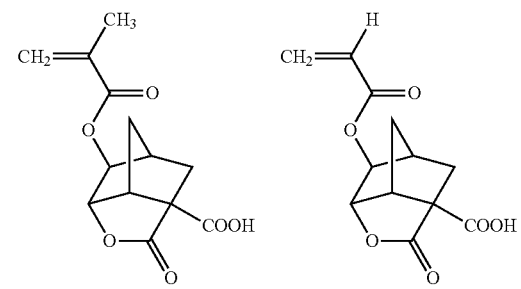
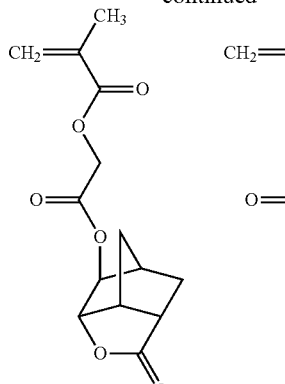
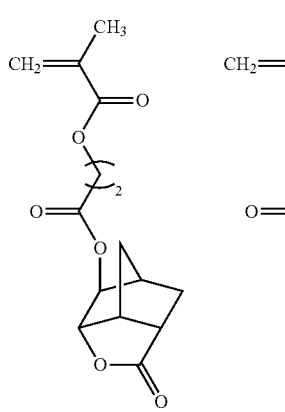
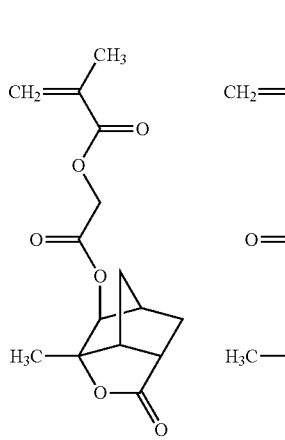
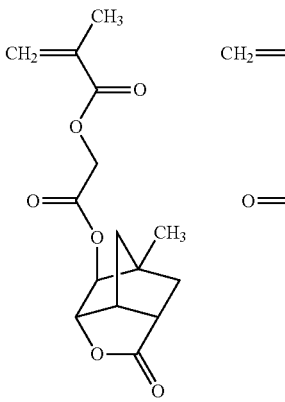

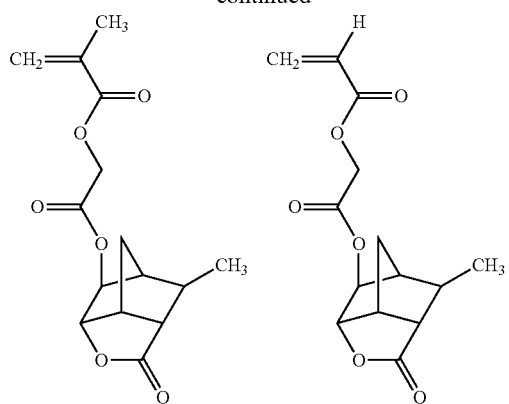
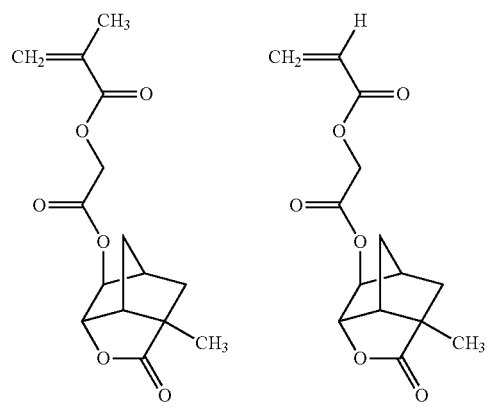
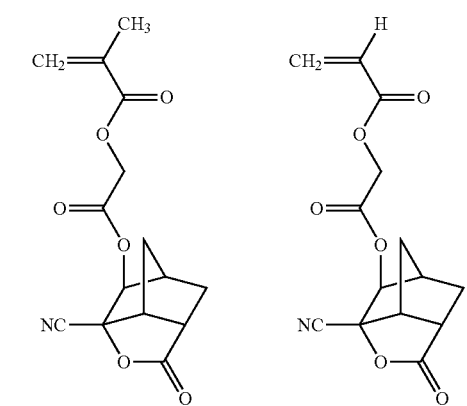
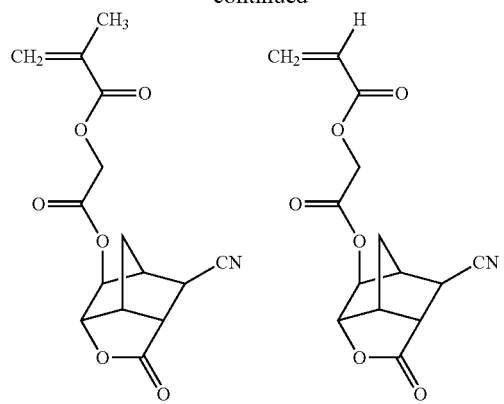

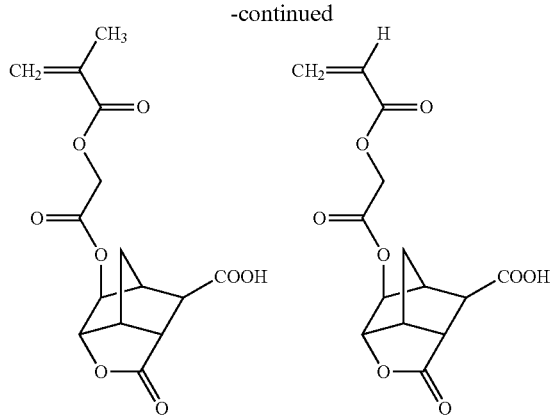
While the following monomer is an acid-labile monomer having a lactone ring; the resin can contain the structural unit derived from the following monomer.
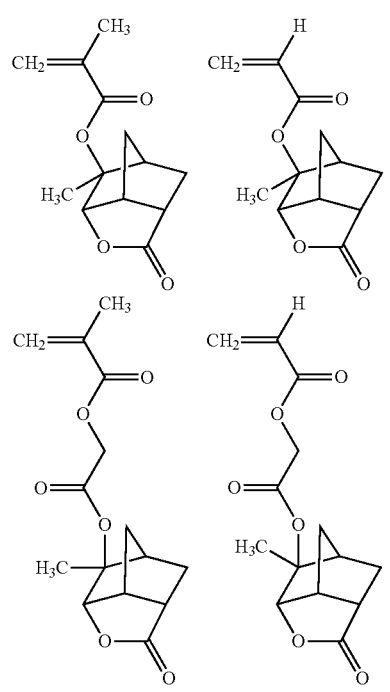
Examples of the monomer represented by the formula (a3-3) include the followings.
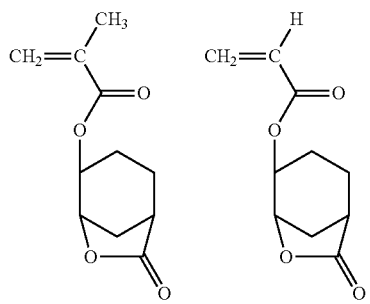
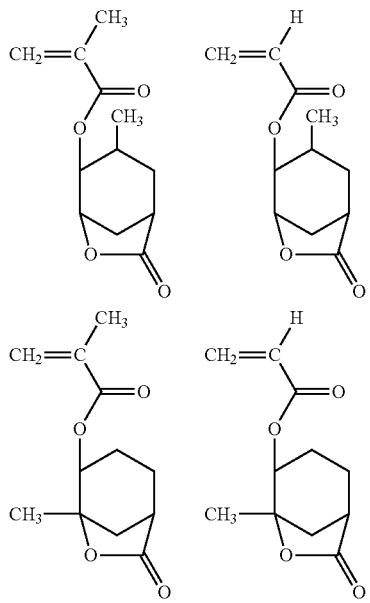

-continued
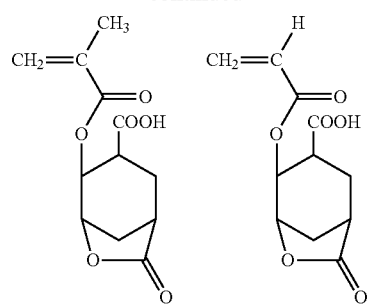
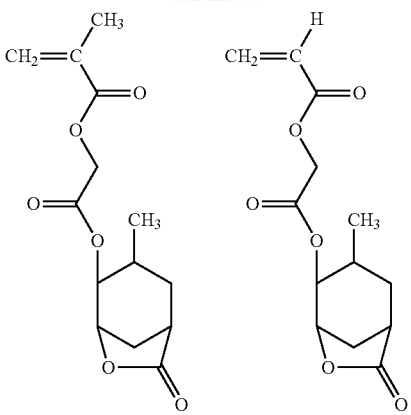
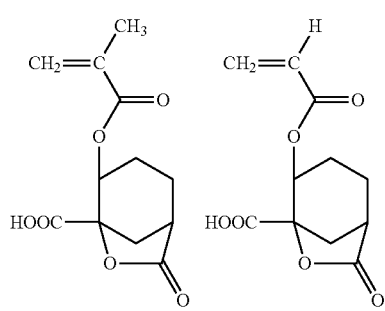
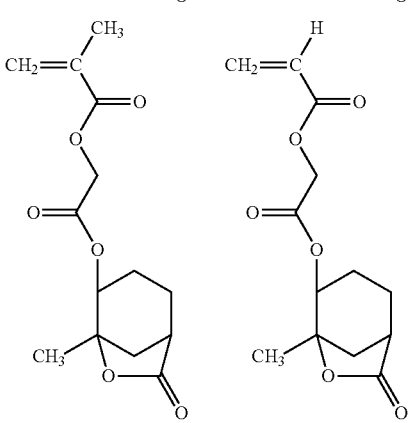
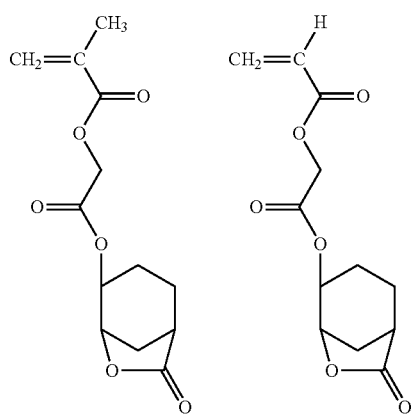
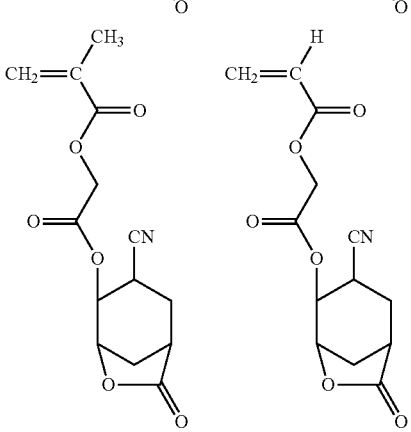
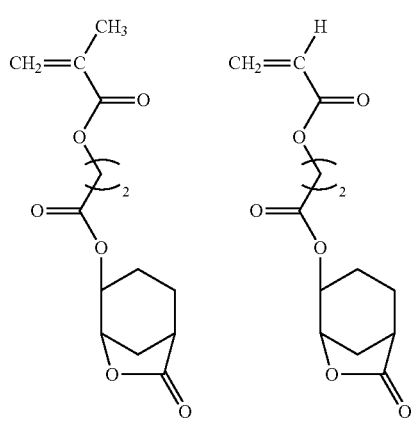
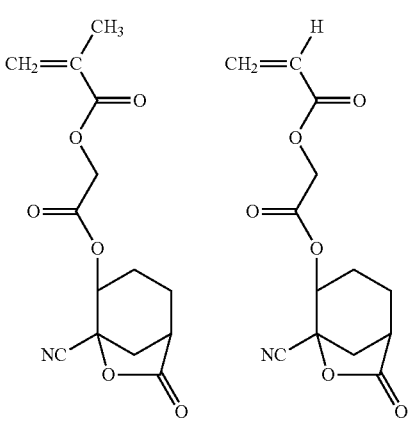 [SMILES: C=C(C)C(=O)OCC(=O)OC1CCC2CC1(C(=O)O)OC2=O ; C=CC(=O)OCC(=O)OC1CCC2CC1(C(=O)O)OC2=O]

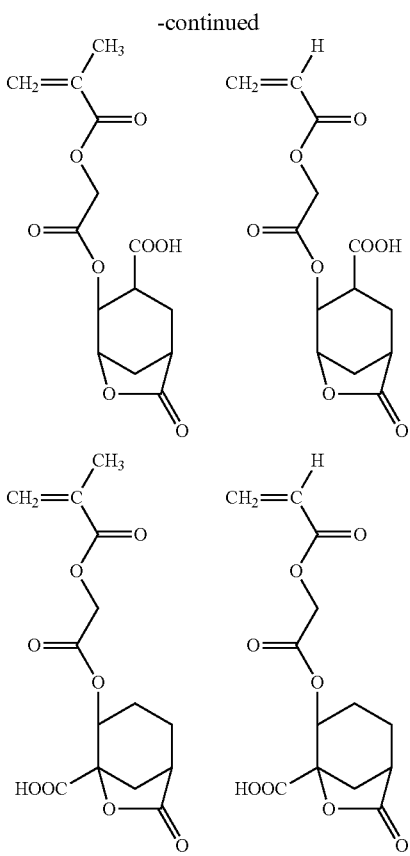

While the following monomer is an acid-labile monomer having a lactone ring, the resin can contain the structural unit derived from the following monomer.

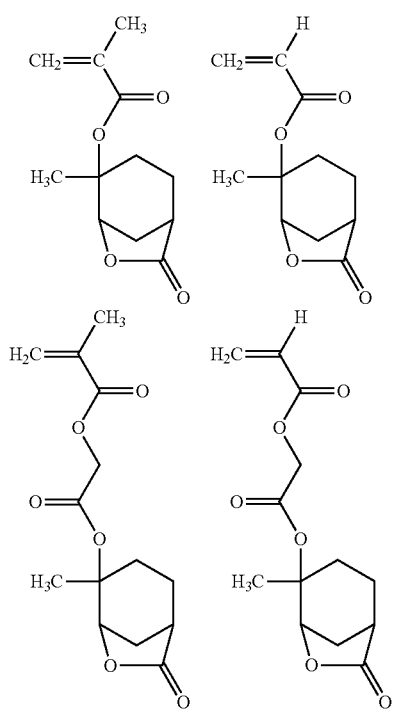

Among them, preferred are 5-oxo-4-oxatricyclo[4.2.1.0$^{3,7}$]nonan-2-yl acrylate, 5-oxo-4-oxatricyclo[4.2.1.0$^{3,7}$]nonan-2-yl methacrylate, tetrahydro-2-oxo-3-furyl acrylate, tetrahydro-2-oxo-3-furyl methacrylate, 2-(5-oxo-4-oxatricyclo[4.2.1.0$^{3,7}$]nonan-2-yloxy)-2-oxoethyl acrylate and 2-(5-oxo-4-oxatricyclo[4.2.1.0$^{3,7}$]nonan-2-yloxy)-2-oxoethyl methacrylate, and more preferred are 5-oxo-4-oxatricyclo[4.2.1.0$^{3,7}$]nonan-2-yl methacrylate, tetrahydro-2-oxo-3-furyl methacrylate and 2-(5-oxo-4-oxatricyclo[4.2.1.0$^{3,7}$]nonan-2-yloxy)-2-oxoethyl methacrylate.

When the resin of the present invention contains the structural unit derived from the acid-stable monomer having a lactone ring and no acid-labile group, the content thereof is usually 5 to 50% by mole and preferably 10 to 45% by mole and more preferably 15 to 40% by mole based on total molar of all the structural units of the resin.

Examples of the other monomer having no acid-labile group include the monomers represented by the formulae (a4-1), (a4-2) and (a4-3):

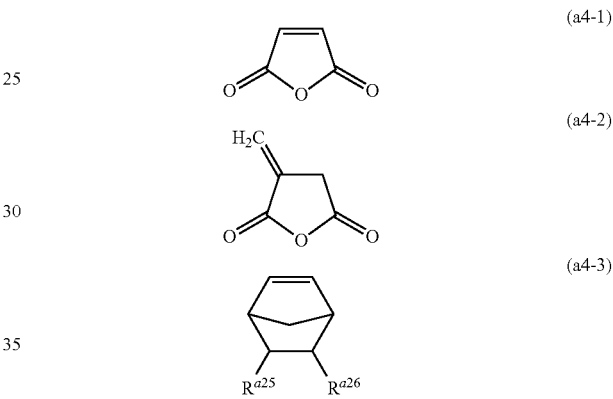

wherein $R^{a25}$ and $R^{a26}$ independently represents a hydrogen atom, a C1-C3 aliphatic hydrocarbon group which can have one or more substituents, a carboxyl group, a cyano group or a —COOR$^{a27}$ group in which R$^{a27}$ represents a C1-C36 aliphatic hydrocarbon group or a C3-C36 saturated cyclic hydrocarbon group, and one or more —CH$_2$— in the C1-C36 aliphatic hydrocarbon group and the C3-C36 saturated cyclic hydrocarbon group can be replaced by —O— or —CO—, with the proviso that the carbon atom bonded to —O— of R$^{a27}$ of —COOR$^{a27}$ is not a tertiary carbon atom, or R$^{a25}$ and R$^{a26}$ are bonded together to form a carboxylic anhydride residue represented by —C(=O)OC(=O)—.

Examples of the substituent of the C1-C3 aliphatic hydrocarbon group include a hydroxyl group. Examples of the C1-C3 aliphatic hydrocarbon group which can have one or more substituents include a C1-C3 alkyl group such as a methyl group, an ethyl group and a propyl group, and a C1-C3 hydroxyalkyl group such a hydroxymethyl group and a 2-hydroxyethyl group. The C1-C36 aliphatic hydrocarbon group represented by R$^5$ is preferably a C1-C8 aliphatic hydrocarbon group and is more preferably a C1-C6 aliphatic hydrocarbon group. The C3-C36 saturated cyclic hydrocarbon group represented by R$^{25}$ is preferably a C4-C36 saturated cyclic hydrocarbon group, and is more preferably C4-C12 saturated cyclic hydrocarbon group. Examples of R$^{25}$ include a methyl group, an ethyl group, a propyl group, a 2-oxo-oxolan-3-yl group and a 2-oxo-oxolan-4-yl group.

Examples of the monomer represented by the formula (a4-3) include 2-norbornene, 2-hydroxy-5-norbornene, 5-norbornene-2-carboxylic acid, methyl 5-norbornene-2-carboxylate, 2-hydroxyethyl 5-norbornene-2-carboxylate, 5-norbornene-2-methanol and 5-norbornene-2,3-dicarboxylic anhydride.

When the resin contains a structural unit derived from a monomer represented by the formula (a4-1), (a4-2) or (a4-3), the content thereof is usually 2 to 40% by mole and preferably 3 to 30% by mole and more preferably 5 to 20% by mole based on total molar of all the structural units of the resin.

Preferable resin is a copolymer comprising one or more structural units derived from the compound (I), one or more structural units derived from the monomer (a1) and the structural units derived from the monomer (a2) and/or the monomer (a3). The monomer (a1) is preferably the monomer represented by the formula (a1-1) or the monomer represented by the formula (a1-2), and is more preferably the monomer represented by the formula (a1-1). The monomer (a2) is preferably the monomer represented by the formula (a2-1), and the monomer (a3) is preferably the monomer represented by the formula (a3-1) or (a3-2).

The resin of the present invention can be produced according to known polymerization methods such as radical polymerization.

The resin of the present invention preferably has 2,500 or more of the weight-average molecular weight, and preferably 3,000 or more of the weight-average molecular weigh. The resin of the present invention preferably has 50,000 or less of the weight-average molecular weight, and preferably 30,000 or less of the weight-average molecular weight. The weight-average molecular weight can be measured with gel permeation chromatography.

The photoresist composition of the present invention contains the resin of the present invention. The content of the resin in the photoresist composition is preferably 80% by weight or more based on sum of solid component. Hereinafter, "solid component" means the components other than a solvent among all components of the photoresist composition. The photoresist composition of the present invention contains an acid generator. The content of the acid generator is usually 1 part by weight or more and preferably 3 parts by weight or more relative to 100 parts by weight of the resin. The content of the acid generator is usually 30 parts by weight or less and preferably 25 parts by weight or less relative to 100 parts by weight of the resin.

The acid generator is a substance which is decomposed to generate an acid by applying a radiation such as a light, an electron beam or the like on the substance itself or on a photoresist composition containing the substance. The acid generated from the acid generator acts on the resin resulting in cleavage of the acid-labile group existing in the resin.

Examples of the acid generator include a nonionic acid generator, an ionic acid generator and the combination thereof. Examples of the nonionic acid generator include an organo-halogen compound, a sulfone compound such as a disulfone, a ketosulfone and a sulfonyldiazomethane, a sulfonate compound such as a 2-nitrobenzylsulfonate, an aromatic sulfonate, an oxime sulfonate, an N-sulfonyloxyimide, a sulfonyloxyketone and DNQ 4-sulfonate. Examples of the ionic acid generator include an onium salt compound such as a diazonium salt, a phosphonium salt, a sulfonium salt and an iodonium salt. Examples of the anion of the onium salt include a sulfonic acid anion, a sulfonylimide anion and a sulfonylmethide anion. The onium salt compound is preferable.

Other examples of the acid generator include acid generators described in JP 63-26653A, JP55-164824A, JP62-69263A, JP63-146038 A, JP 63-163452 A, JP 62-153853 A, JP 63-146029 A, U.S. Pat. No. 3,779,778, U.S. Pat. No. 3,849,137, DE Pat. No. 3914407 and EP Patent No. 126,712.

Preferable examples of the acid generator include a fluorine-containing acid generator, and more preferable acid generator is a salt represented by the formula (B1):

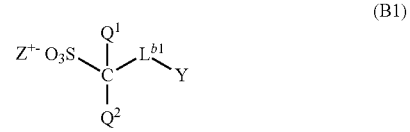

wherein $Q^1$ and $Q^2$ each independently represent a fluorine atom or a C1-C6 perfluoroalkyl group,
$L^{b1}$ represents a single bond or a C1-C17 saturated divalent hydrocarbon group which can have one or more substituents, and one or more —CH$_2$— in the saturated divalent hydrocarbon group can be replaced by —O— or —CO—,
Y represents a C1-C18 aliphatic hydrocarbon group or a C3-C18 saturated cyclic hydrocarbon group, and the aliphatic hydrocarbon group and the saturated cyclic hydrocarbon group can have one or more substituents, and one or more —CH$_2$— in the aliphatic hydrocarbon group and the saturated cyclic hydrocarbon group can be replaced by —O—, —SO$_2$— or —CO—,
$Z^+$ represents an organic cation.

Examples of the C1-C6 perfluoroalkyl group include a trifluoromethyl group, a pentafluoroethyl group, a heptafluoropropyl group, a nonafluorobutyl group, an undecafluoropentyl group and a tridecafluorohexyl group, and a trifluoromethyl group is preferable. $Q^1$ and $Q^2$ each independently preferably represent a fluorine atom or a trifluoromethyl group, and $Q^1$ and $Q^2$ are more preferably fluorine atoms.

Examples of the C1-C17 saturated divalent hydrocarbon group include a C1-C17 alkylene group and a divalent group having an alicyclic divalent hydrocarbon group. Examples of the alkylene group include a linear alkanediyl group such as a methylene group, an ethylene group, a propane-1,3-diyl group, a butane-1,4-diyl group, a pentane-1,5-diyl, a hexane-1,6-diyl group, a heptane-1,7-diyl group, an octane-1,8-diyl group, a nonane-1,9-diyl group, a decane-1,10-diyl group, an undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group, a branched chain alkanediyl group formed by replacing one or more hydrogen atom of the above-mentioned linear alkanediyl group by a C1-C4 alkyl group such as a 1-methylpropane-1,3-diyl group, a 2-methylpropane-1,3-diyl group, a 2-methylpropane-1,2-diyl group, a 1-methylbutane-1,4-diyl group and a 2-methylbutane-1,4-diyl group,
a divalent saturated monocyclic hydrocarbon group such as a cycloalkylene group such as a 1,3-cyclobutylene group, a 1,3-cyclopentylene group, a 1,4-cyclohexylene group and 1,5-cyclooctylene group,
a divalent saturated polycyclic hydrocarbon group such as a norbornane-1,4-diyl group, a norbornane-2,5-diyl group, a adamantane-1,5-diyl group and a adamantane-2,6-diyl group, and a group formed by combining two or more groups selected from the group consisting of the above-mentioned groups.

Examples of the C1-C17 divalent saturated hydrocarbon group in which one or more —CH$_2$— are replaced by —O— or —CO— include *—CO—O-L$^{b2}$-, *—CO—O-L$^{b4}$-CO—O-L$^{b3}$-, *-L$^{b5}$-O, *-L$^{b7}$-O-L$^{b6}$-, *—CO—O-L$^{b8}$-O—, and

*—CO—O-$L^{b10}$-O-$L^{b9}$-CO—O—, wherein $L^{b2}$ represents a single bond or a C1-C15 saturated hydrocarbon group, $L^{b3}$ represents a single bond or a C1-C12 saturated hydrocarbon group, $L^{b4}$ represents C1-C13 saturated hydrocarbon group, with the proviso that total carbon number of $L^{b3}$ and $L^{b4}$ is 1 to 13, $L^{b5}$ represents a C1-C15 saturated hydrocarbon group, $L^{b6}$ represents a C1-C15 saturated hydrocarbon group, $L^{b7}$ represents a C1-C15 saturated hydrocarbon group, with the proviso that total carbon number of $L^{b6}$ and $L^{b7}$ is 1 to 16, $L^{b8}$ represents a C1-C14 saturated hydrocarbon group, $L^{b9}$ represents a C1-C11 saturated hydrocarbon group, $L^{b10}$ represents a C1-C11 saturated hydrocarbon group, with the proviso that total carbon number of $L^{b9}$ and $L^{b10}$ is 1 to 12, and * represents a binding position to —C($R^1$)($R^2$)—. Among them, preferred is *—CO—O-$L^{b2}$-, and more preferred is *—CO—O-$L^{b2}$- in which $L^{b2}$ is a single bond or —$CH_2$—.

Examples of *—CO—O-$L^{b2}$- include *—CO—O— and *—CO—O—$CH_2$—. Examples of *—CO—O-$L^{b4}$-CO—O-$L^{b3}$- include *—CO—O—$CH_2$—CO—O—, *—CO—O—($CH_2$)$_2$—CO—O—, *—CO—O—($CH_2$)$_3$—CO—O—, *—CO—O—($CH_2$)$_4$—CO—O—, *—CO—O—($CH_2$)$_6$—CO—O—, *—CO—O—($CH_2$)$_8$—CO—O, *—CO—O—$CH_2$—CH($CH_3$)—CO—O— and *—CO—O—$CH_2$—C($CH_3$)$_2$—CO—O—. Examples of *-$L^{b5}$-O—CO— include *—$CH_2$—O—CO—, *—($CH_2$)$_2$—O—CO—, *—($CH_2$)$_3$—O—CO—, *—($CH_2$)$_4$—O—CO—, *—($CH_2$)$_6$—O—CO— and *—($CH_2$)$_8$—O—CO—. Examples of *-$L^{b7}$-O-$L^{b6}$- include *—$CH_2$—O—$CH_2$—. Examples of *—CO—O-$L^{b8}$-O— include *—CO—O—$CH_2$—O—, *—CO—O—($CH_2$)$_2$—O—, *—CO—O—($CH_2$)$_3$—O—, *—CO—O—($CH_2$)$_4$—O— and *—CO—O—($CH_2$)$_6$—O—. Examples of *—CO—O-$L^{b10}$-O-$L^{b9}$-CO—O— include the followings.

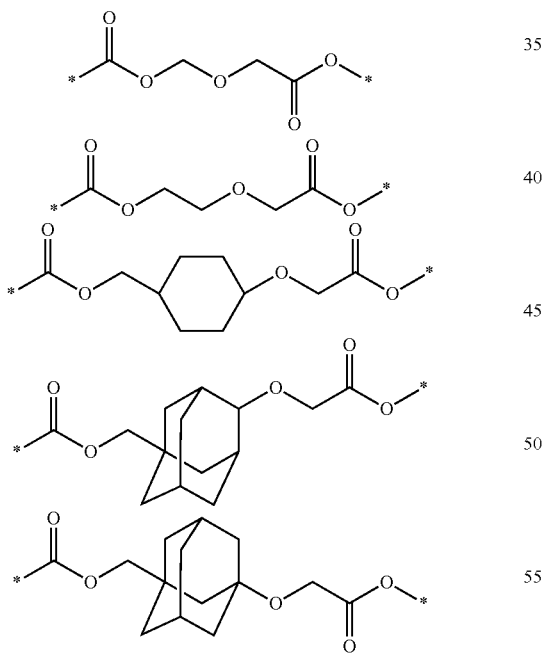

The saturated hydrocarbon group of $L^{b1}$ may have one or more substituents, and examples thereof include a halogen atom, a hydroxyl group, a carboxyl group, a C6-C18 aromatic hydrocarbon group, a C7-C21 aralkyl group, a C2-C4 acyl group and a glycidyloxy group. Examples of the aralkyl group include a benzyl group, a phenylethyl group, a phenylpropyl group, a trityl group, a naphthylmethyl group and a naphthylethyl group.

Examples of the substituent in Y include a halogen atom, a hydroxyl group, an oxo group, a glycidyloxy group, a C2-C4 acyl group, a C1-C12 alkoxy group, a C2-C7 alkoxycarbonyl group, a C1-C12 aliphatic hydrocarbon group, a C1-C12 hydroxy-containing aliphatic hydrocarbon group, a C3-C16 saturated cyclic hydrocarbon group, a C6-C18 aromatic hydrocarbon group, a C7-C21 aralkyl group and -($CH_2$)$_{j2}$—O—CO—$R^{b1}$— in which $R^{b1}$ represents a C1-C16 aliphatic hydrocarbon group, a C3-C16 saturated cyclic hydrocarbon group or a C6-C18 aromatic hydrocarbon group and j2 represents an integer of 0 to 4. Examples of the halogen atom include a fluorine atom, a chlorine atom, a bromine atom and an iodine atom. Examples of the acyl group include an acetyl group and a propionyl group, and examples of the alkoxy group include a methoxy group, an ethoxy group, a propoxy group, an isopropoxy group and a butoxy group. Examples of the alkoxycarbonyl group include a methoxycarbonyl group, an ethoxycarbonyl group, a propoxycarbonyl group, an isopropoxycarbonyl group and a butoxycarbonyl group. Examples of the aliphatic hydrocarbon group include the same as described above. Examples of the hydroxyl-containing aliphatic hydrocarbon group include a hydroxymethyl group. Examples of the C3-C16 saturated cyclic hydrocarbon group include the same as described above, and examples of the aromatic hydrocarbon group include a phenyl group, a naphthyl group, an anthryl group, a p-methylphenyl group, a p-tert-butylphenyl group and a p-adamantylphenyl group. Examples of the aralkyl group include a benzyl group, a phenethyl group, a phenylpropyl group, a trityl group, a naphthylmethyl group and a naphthylethyl group.

Examples of the C1-C18 aliphatic hydrocarbon group represented by Y include a methyl group, an ethyl group, a propyl group, an isopropyl group, a butyl group, an isobutyl group, a sec-butyl group, a tert-butyl group, a pentyl group, a neopentyl group, a 1-methylbutyl group, a 2-methylbutyl group, a 1,2-dimethylpropyl group, a 1-ethylpropyl group, a hexyl group, a 1-methylpentyl group, a heptyl group, an octyl group, a 2-ethylhexyl group, a nonyl group, a decyl group, an undecyl group and a dodecyl group, and a C1-C6 alkyl group is preferable. Examples of the C3-C36 saturated cyclic hydrocarbon group represented by Y include the groups represented by the formulae (Y1) to (Y26):

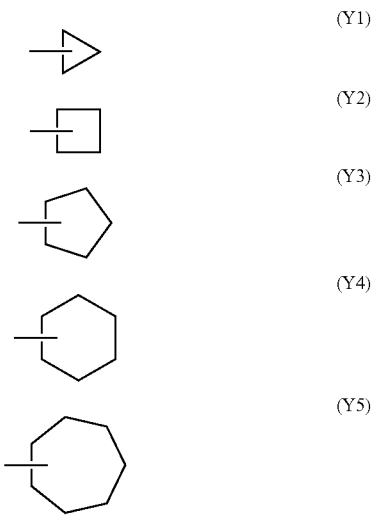

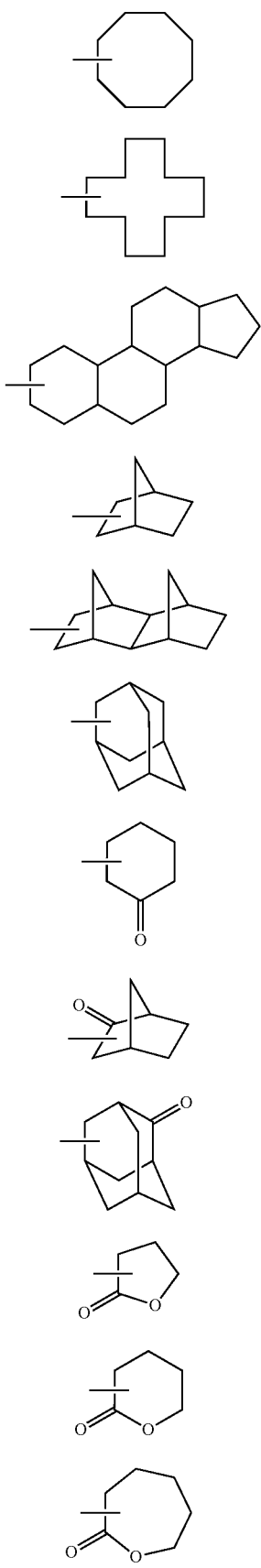
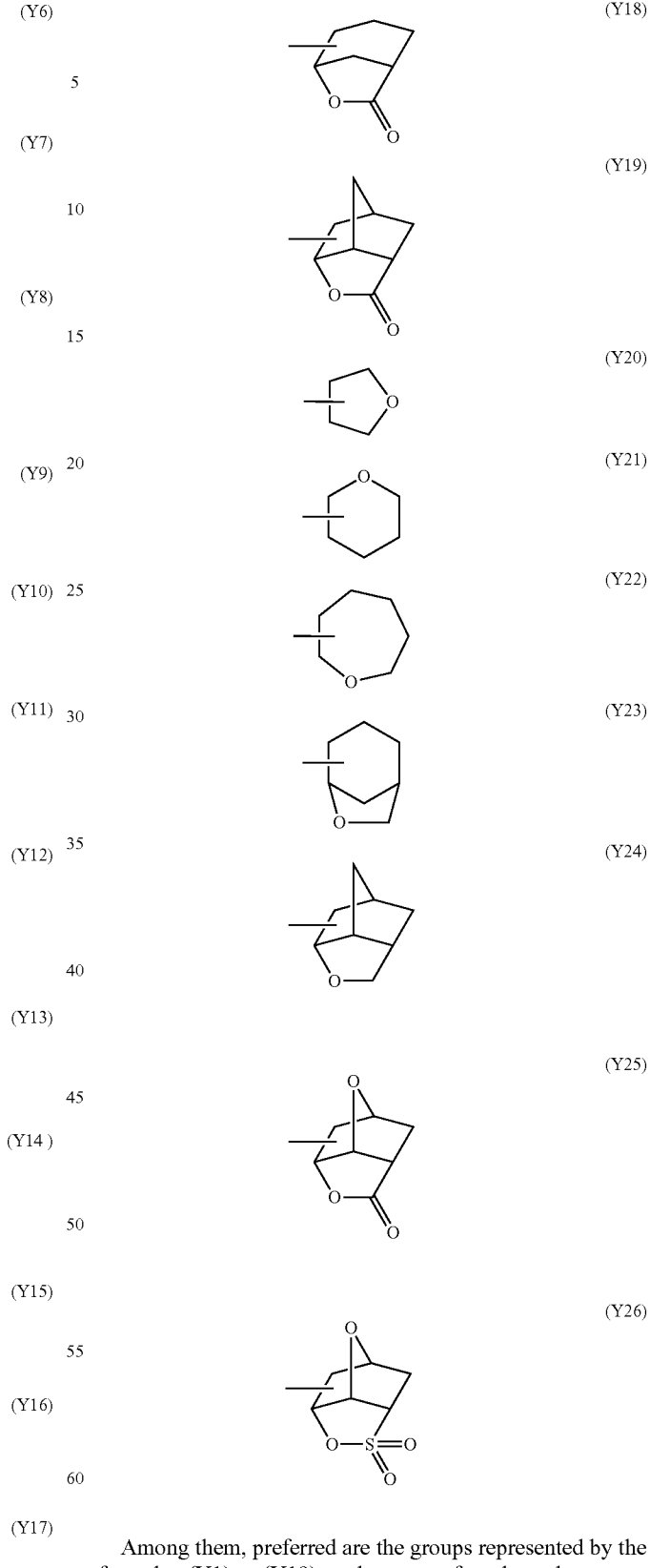
Among them, preferred are the groups represented by the formulae (Y1) to (Y19), and more preferred are the groups represented by the formulae (Y11), (Y14), (Y15) and (Y19). The groups represented by the formulae (Y11) and (Y14) are especially preferable.

Examples of Y having one or more substituents include the followings:

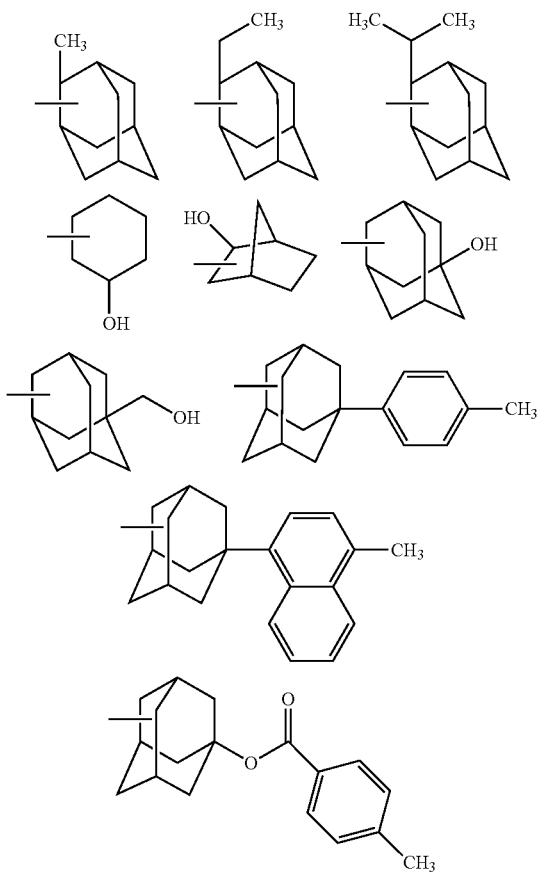

Y is preferably an adamantyl group which can have one or more substituents, and is more preferably an adamantyl group or an oxoadamantyl group.

Among the sulfonic acid anions of the salt represented by the formula (B1), preferred is a sulfonic acid anion in which $L^{b1}$ is *—CO—O-$L^{b2}$-, and more preferred are anions represented by the formulae (b1-1-1) to (b1-1-9).

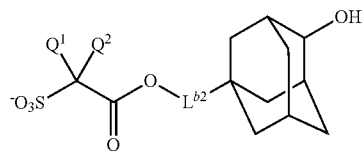
(b1-1-1)

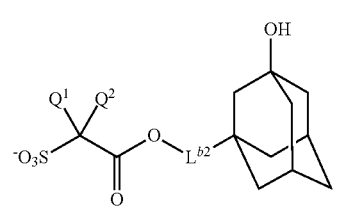
(b1-1-2)

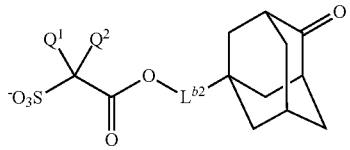
(b1-1-3)

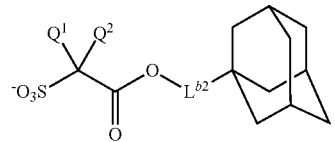
(b1-1-4)

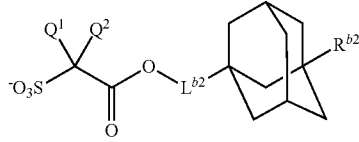
(b1-1-5)

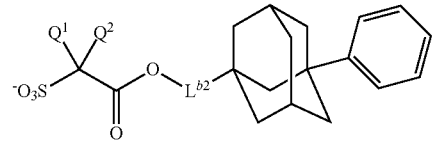
(b1-1-6)

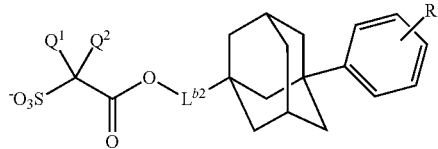
(b1-1-7)

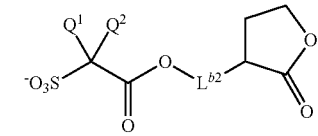
(b1-1-8)

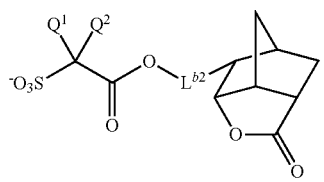
(b1-1-9)

wherein $Q^1$, $Q^2$ and $L^{b2}$ are the same as defined above, and $R^{b2}$ and $R^{b3}$ each independently represent a C1-C4 aliphatic hydrocarbon group, preferably a methyl group.

Examples of the anions of the salt represented by the formula (B1) include the following.

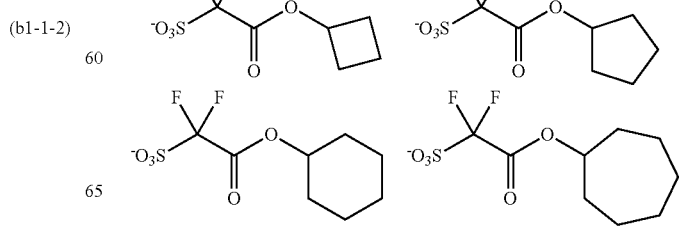

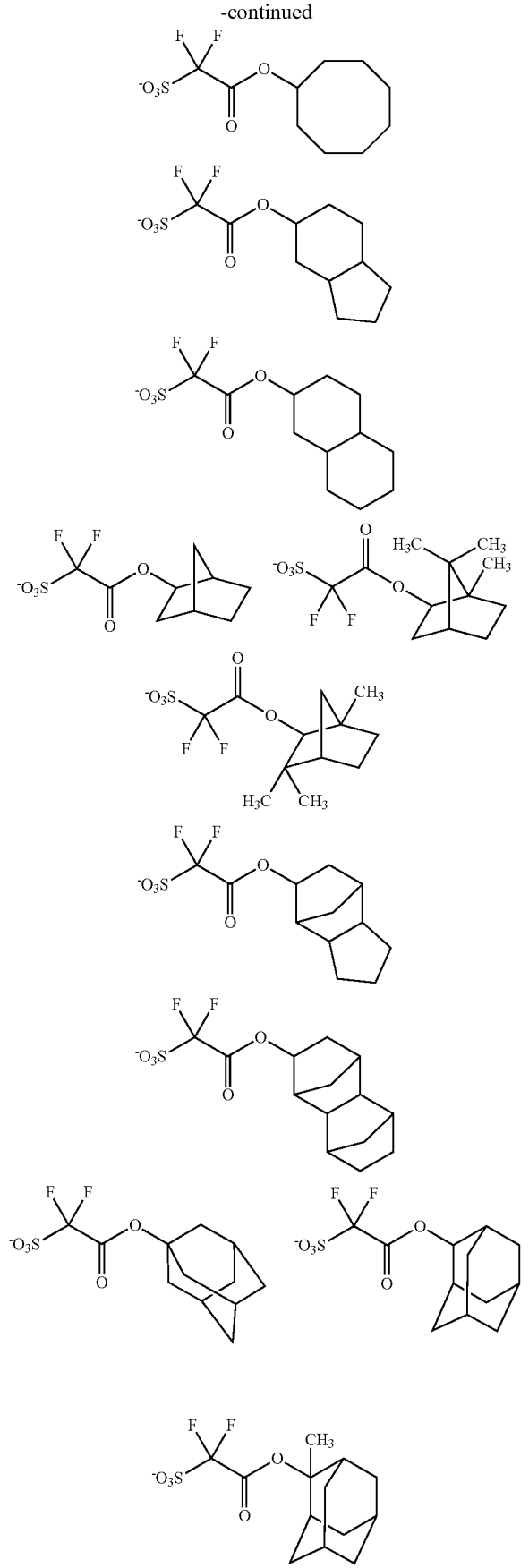
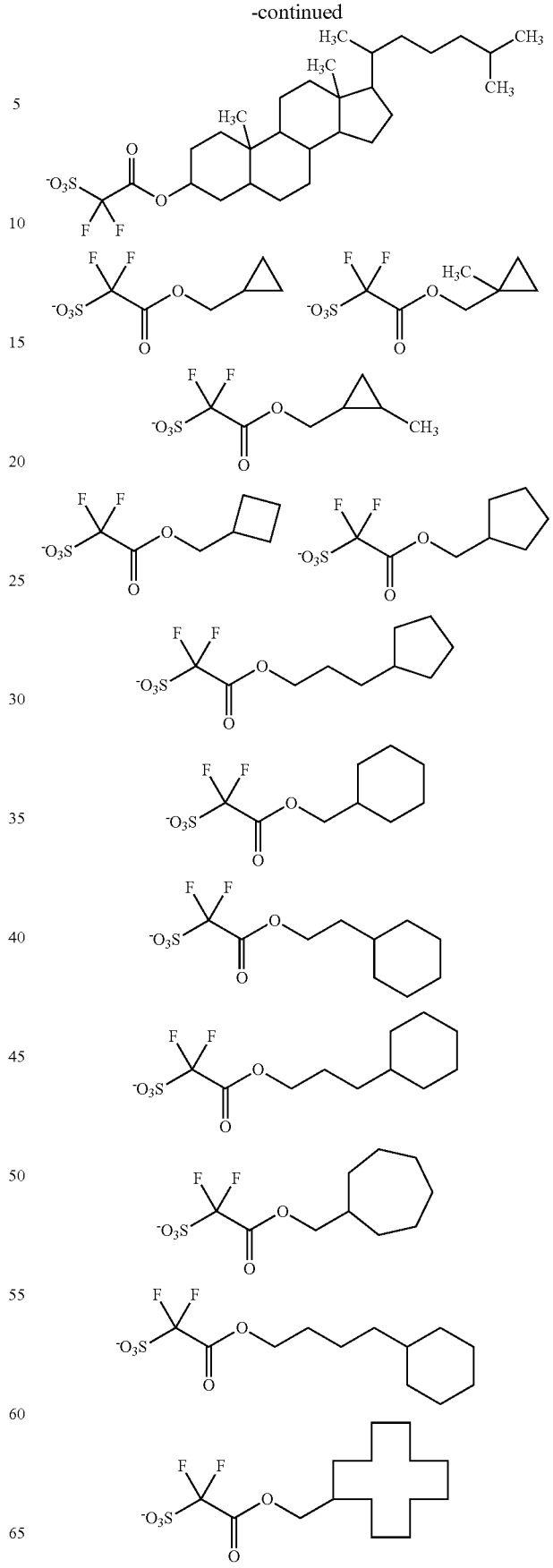

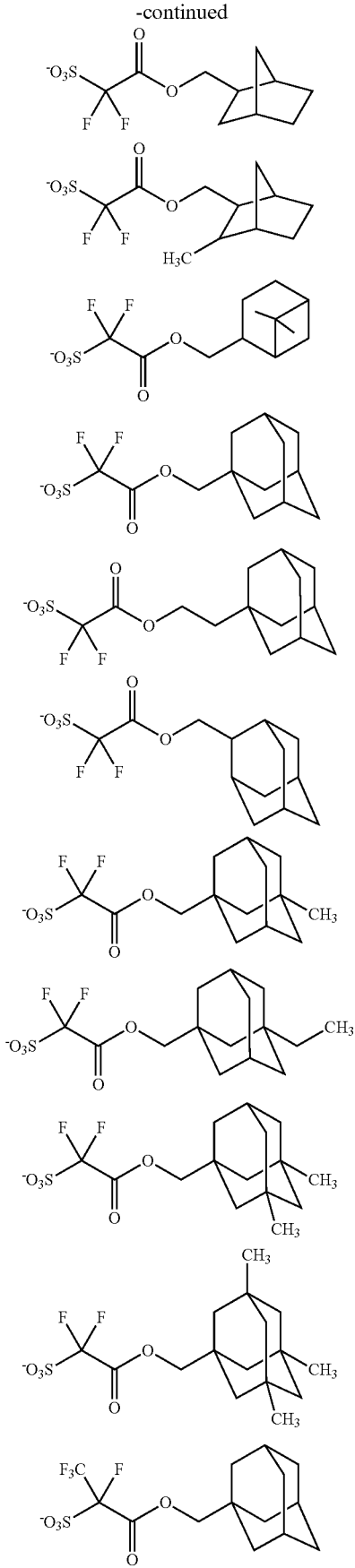
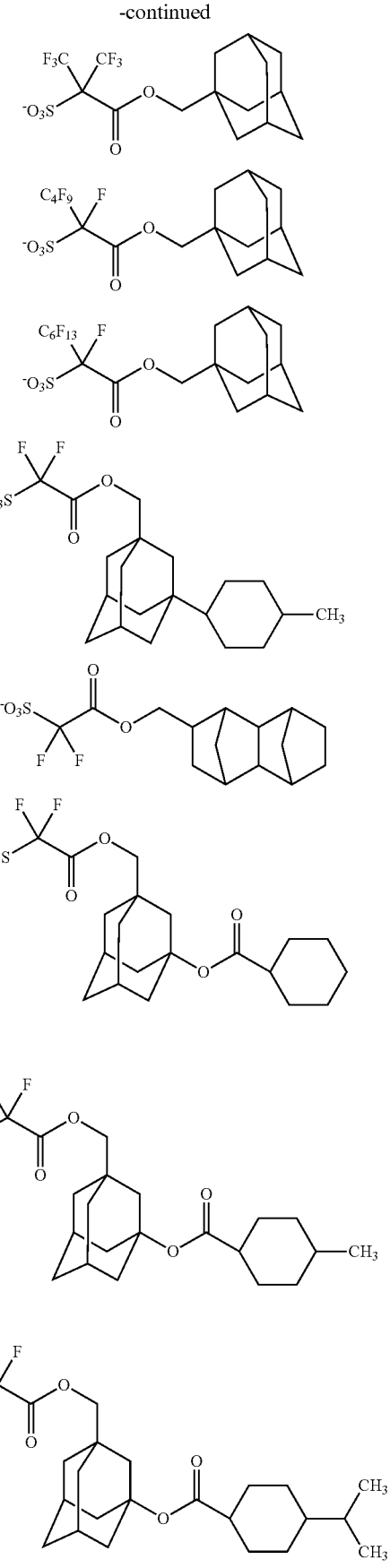

87
-continued
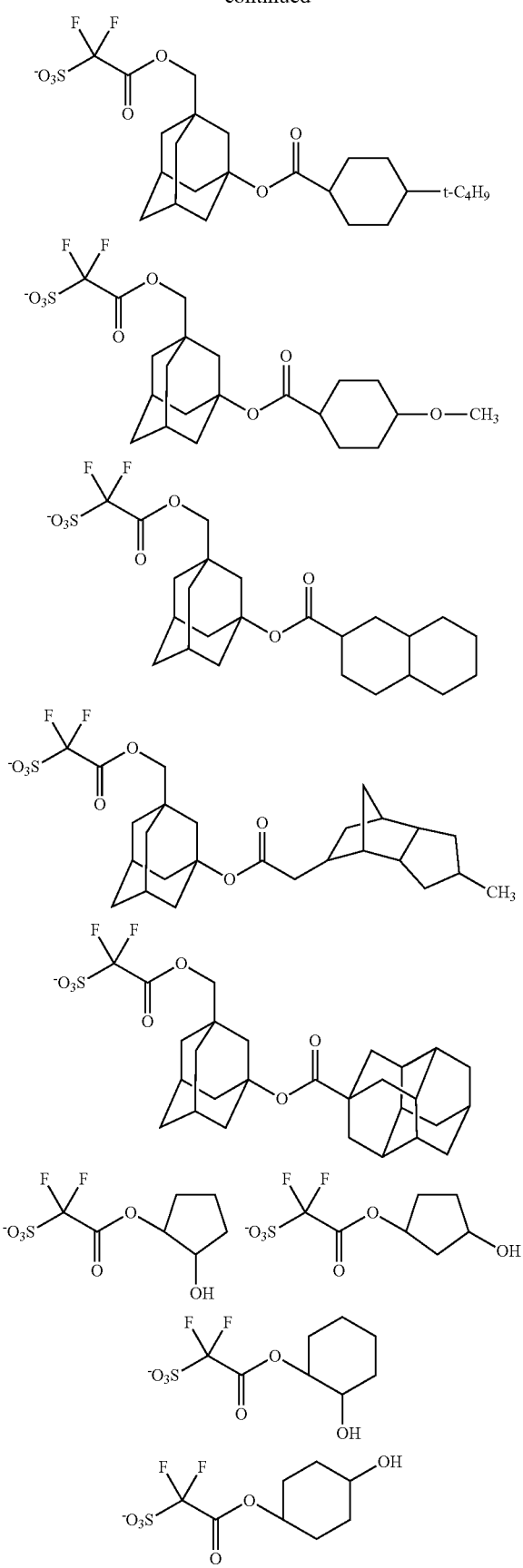
88
-continued
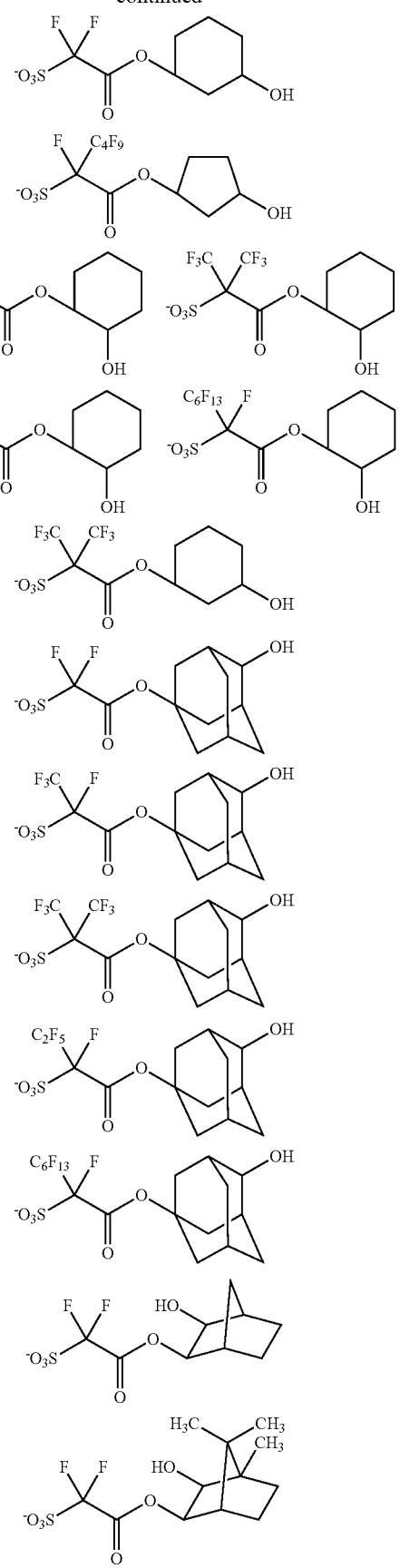

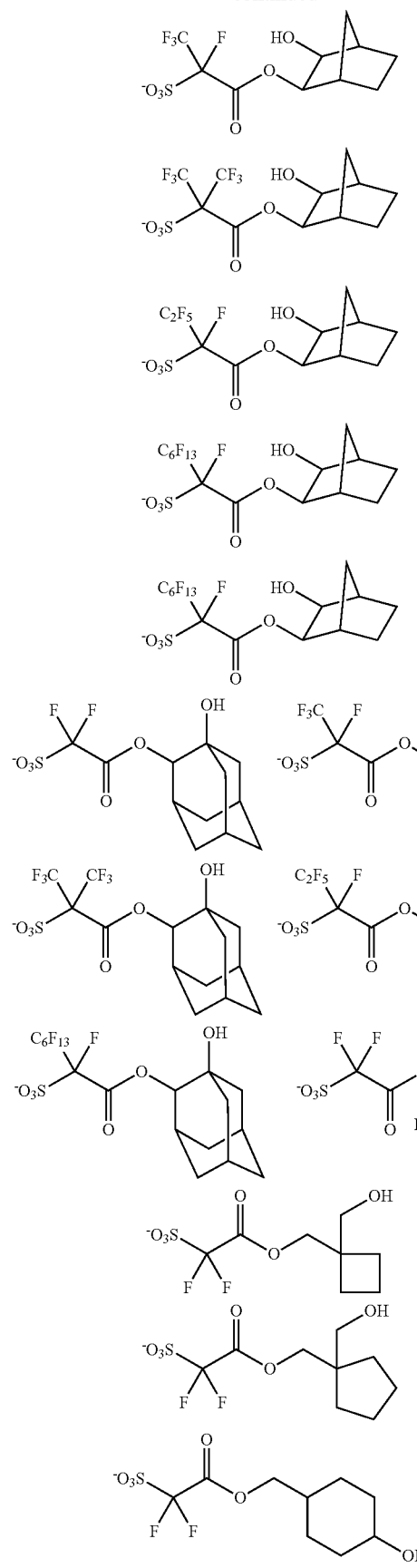
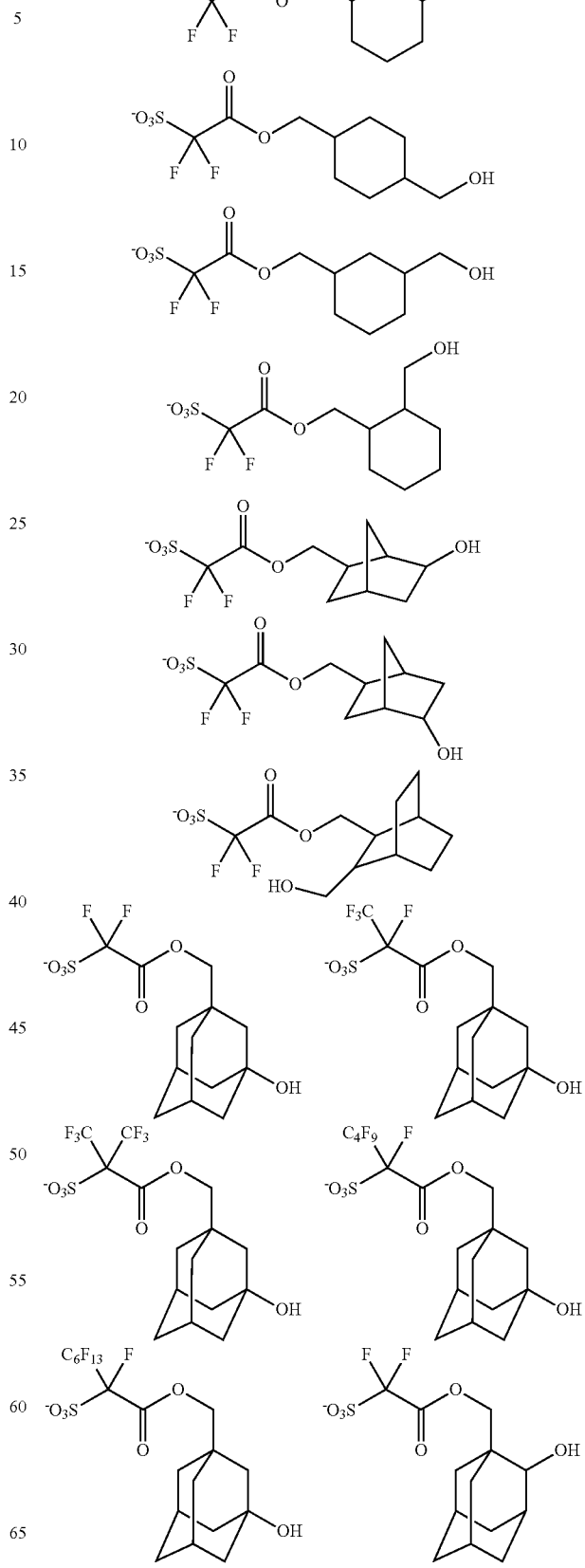

91
-continued
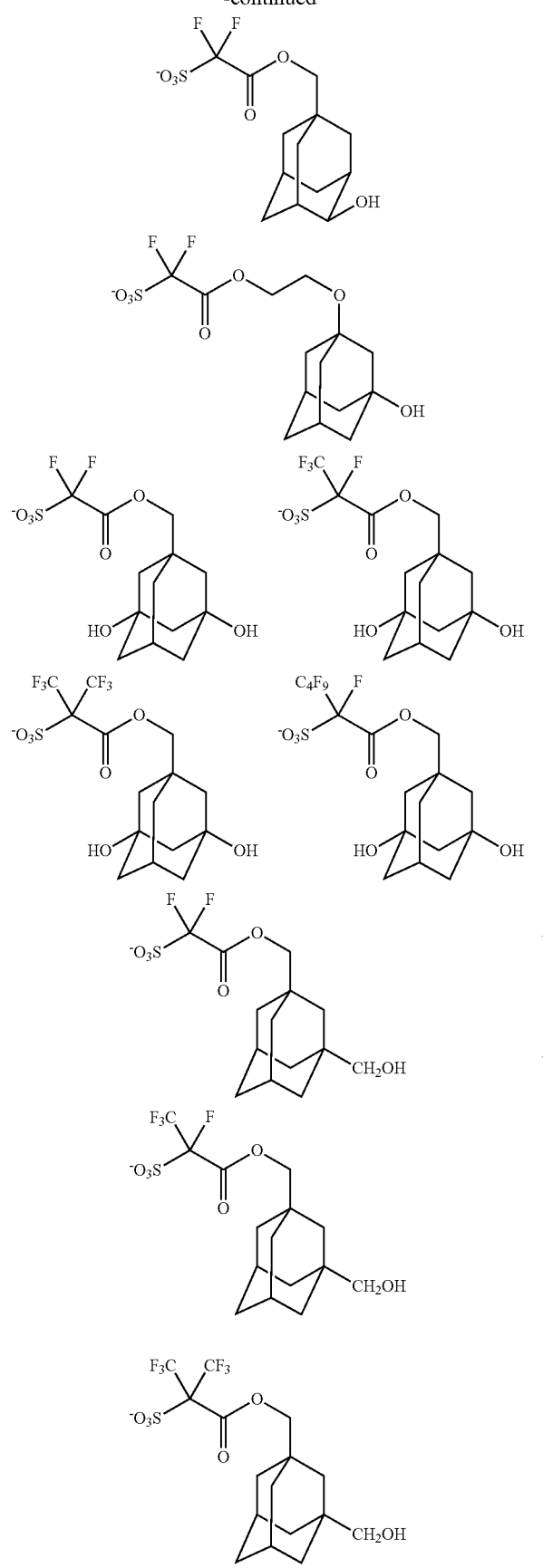
92
-continued
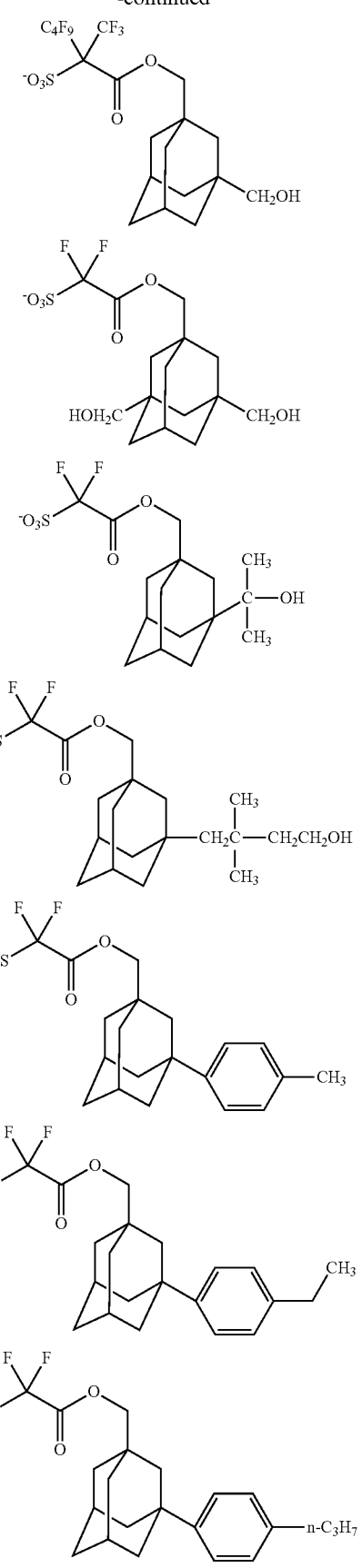

-continued
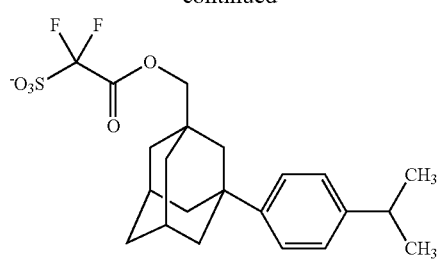
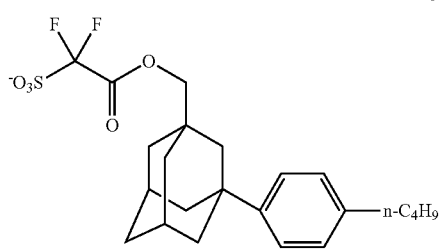
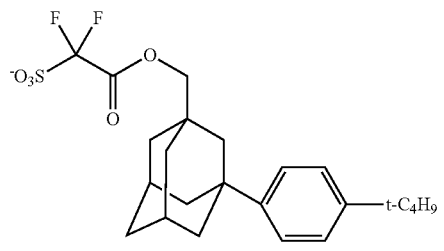
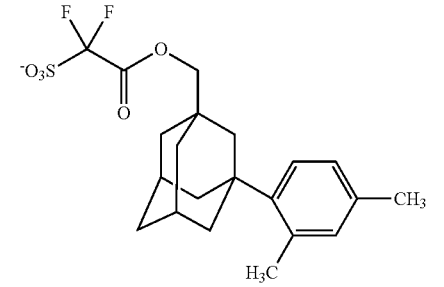
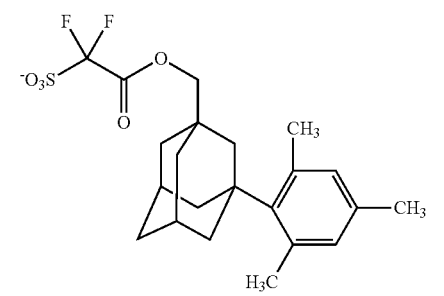
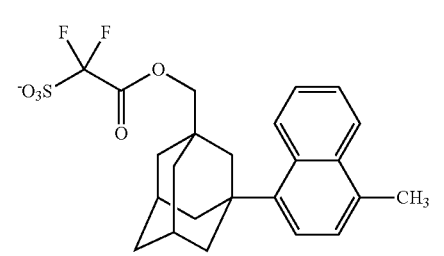
-continued
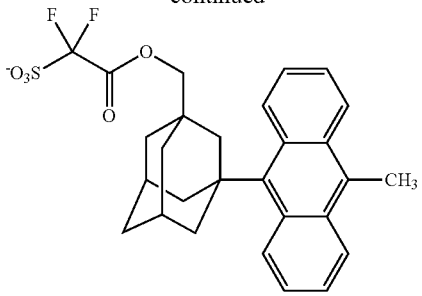
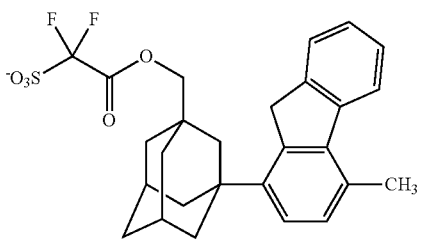
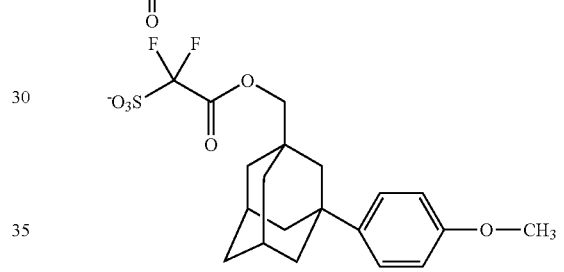
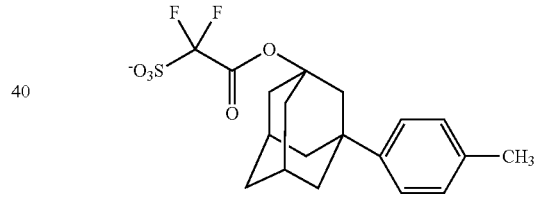
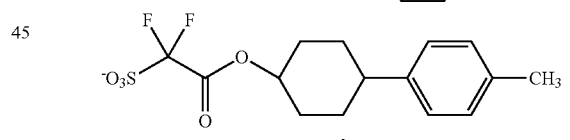
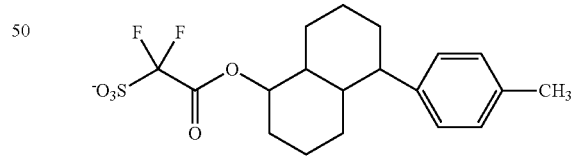
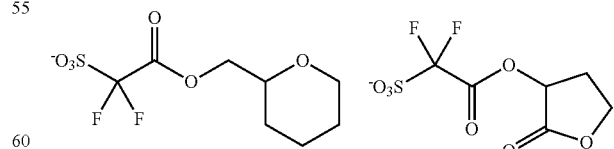
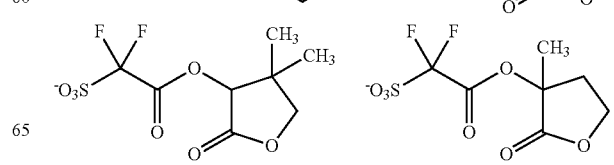

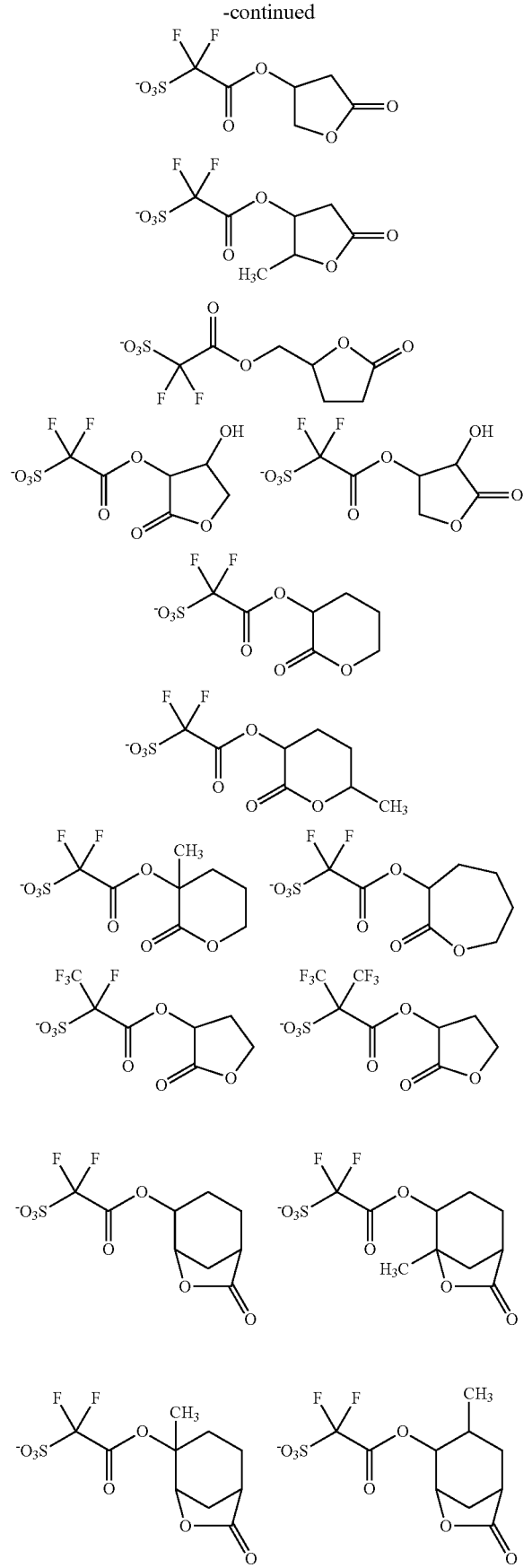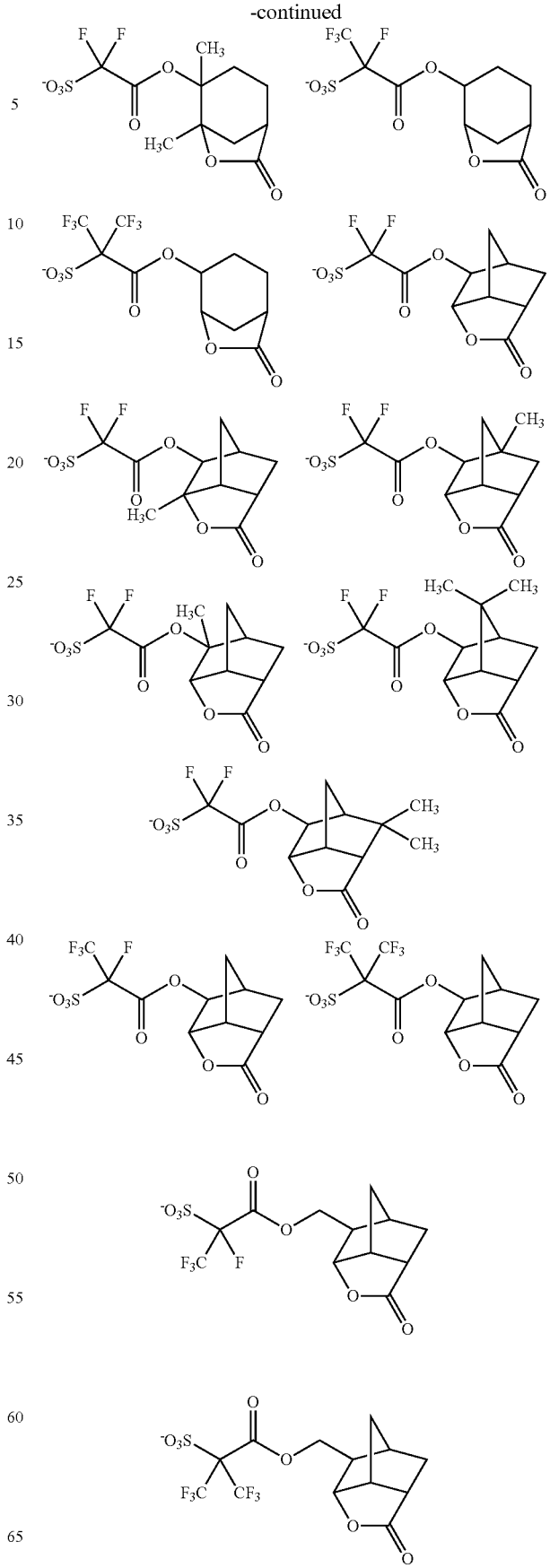

-continued

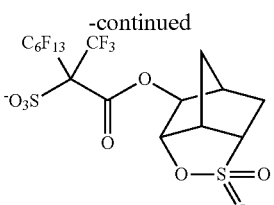
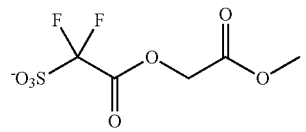
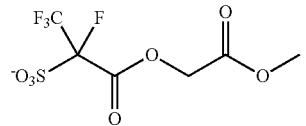
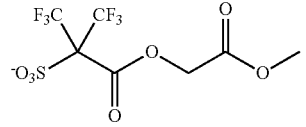
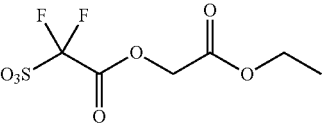
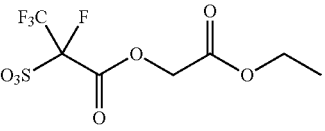
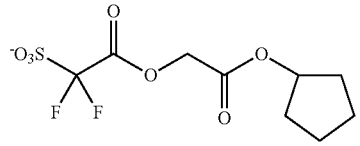
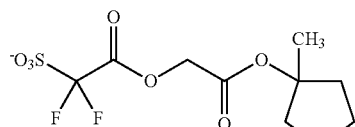
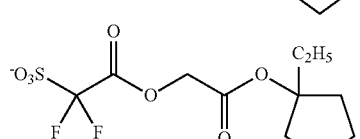
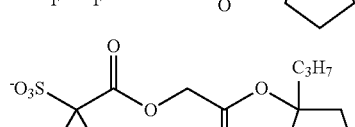
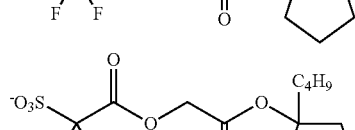
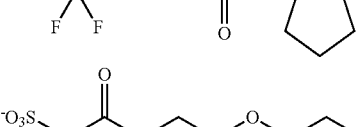
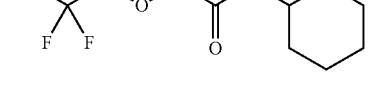
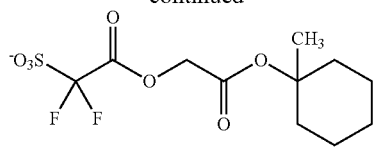
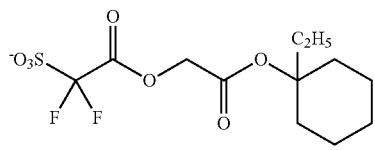
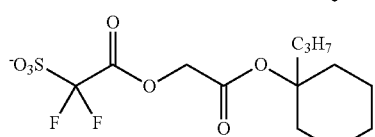
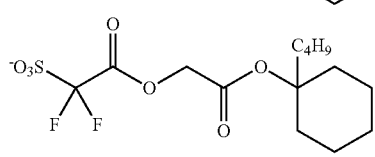
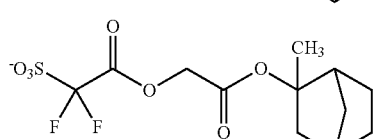
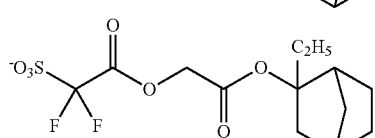
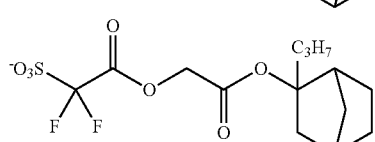
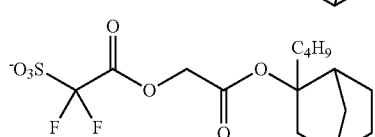
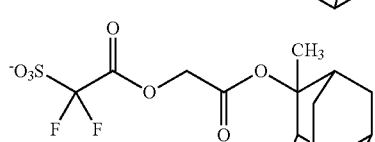
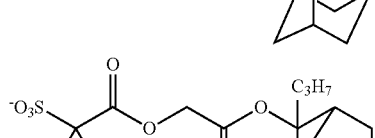
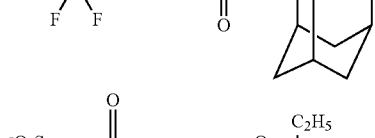
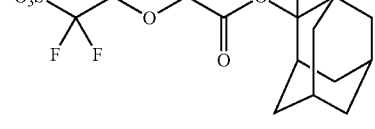

101
-continued
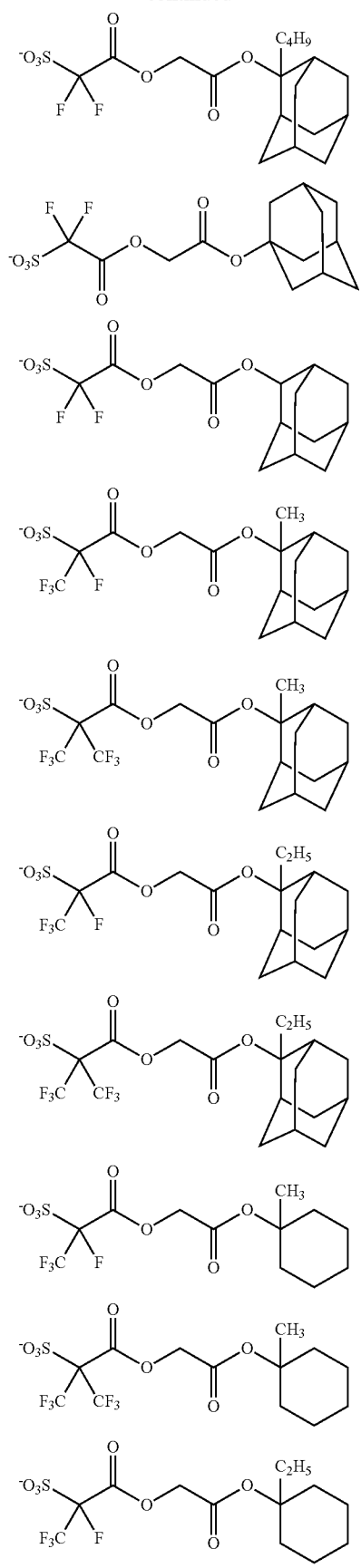
102
-continued
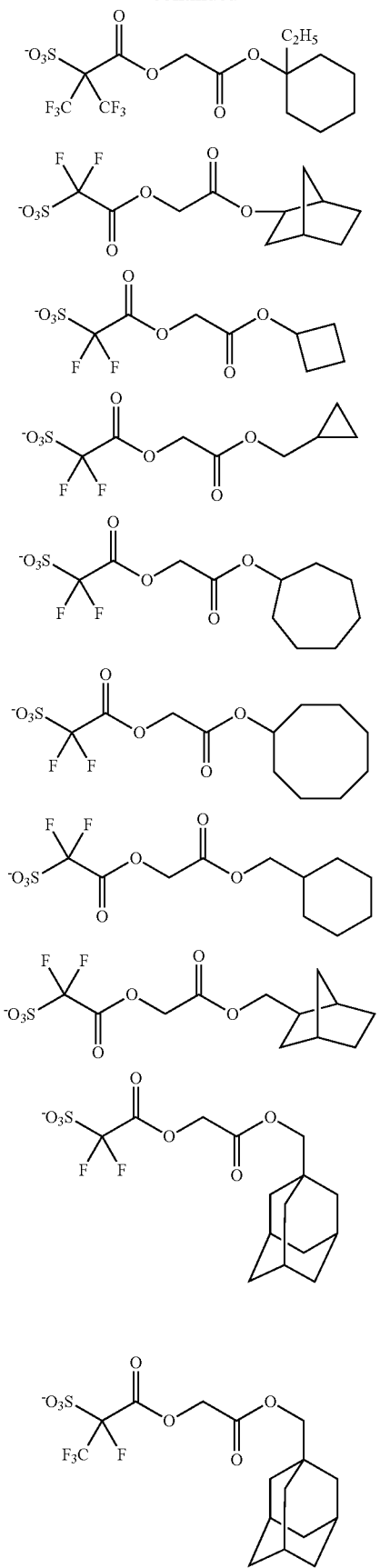

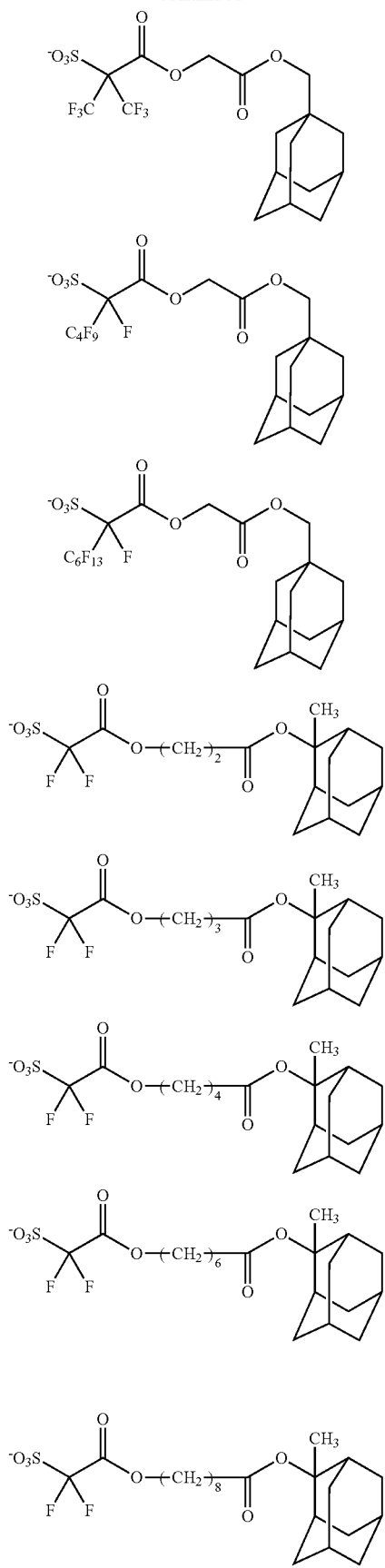
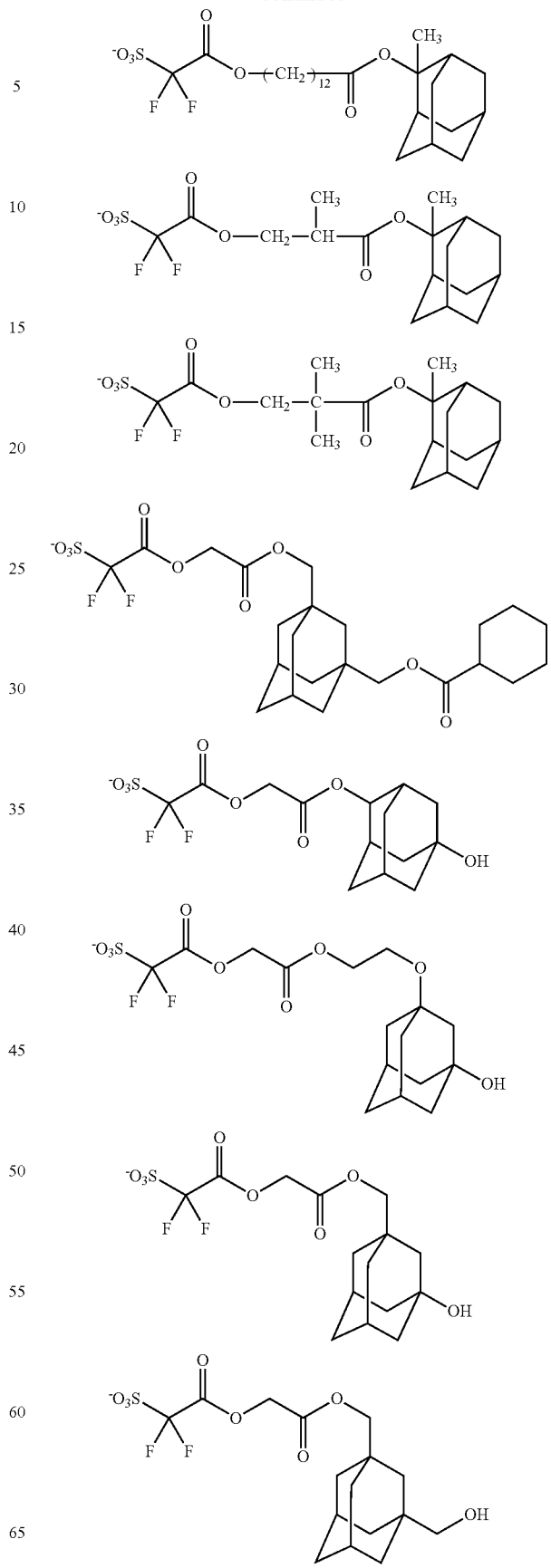

-continued

107
-continued
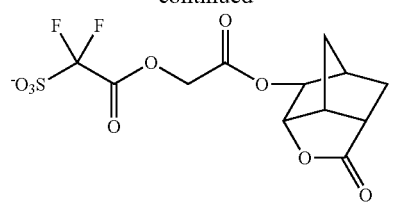
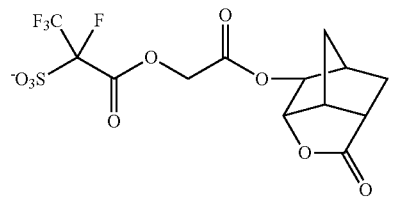
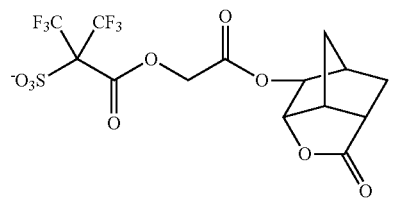
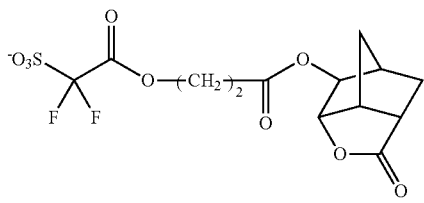
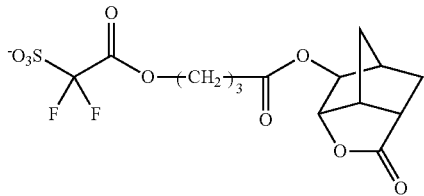
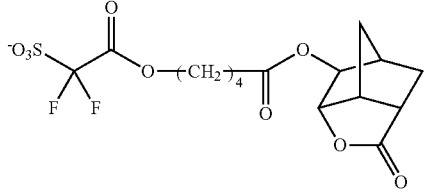
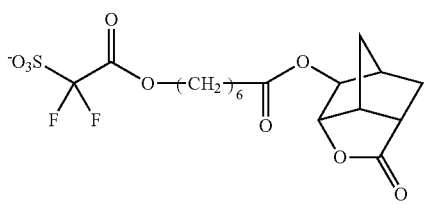
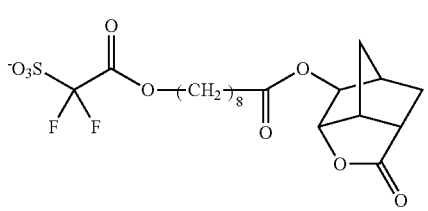
108
-continued
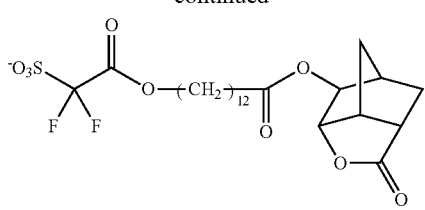
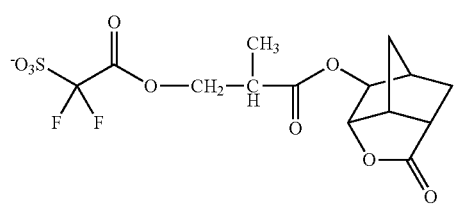
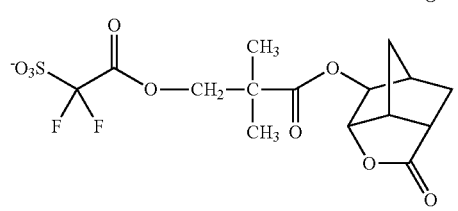
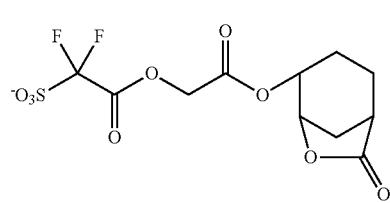
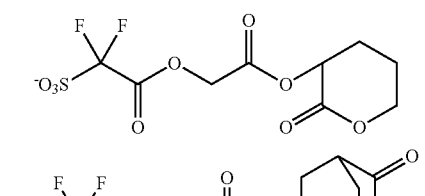
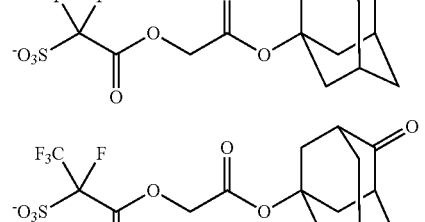
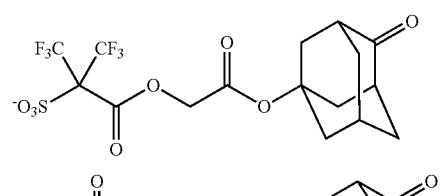
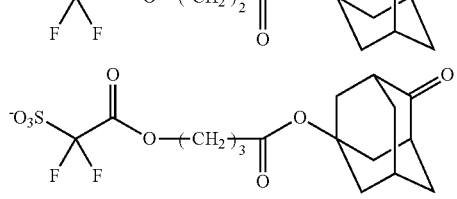

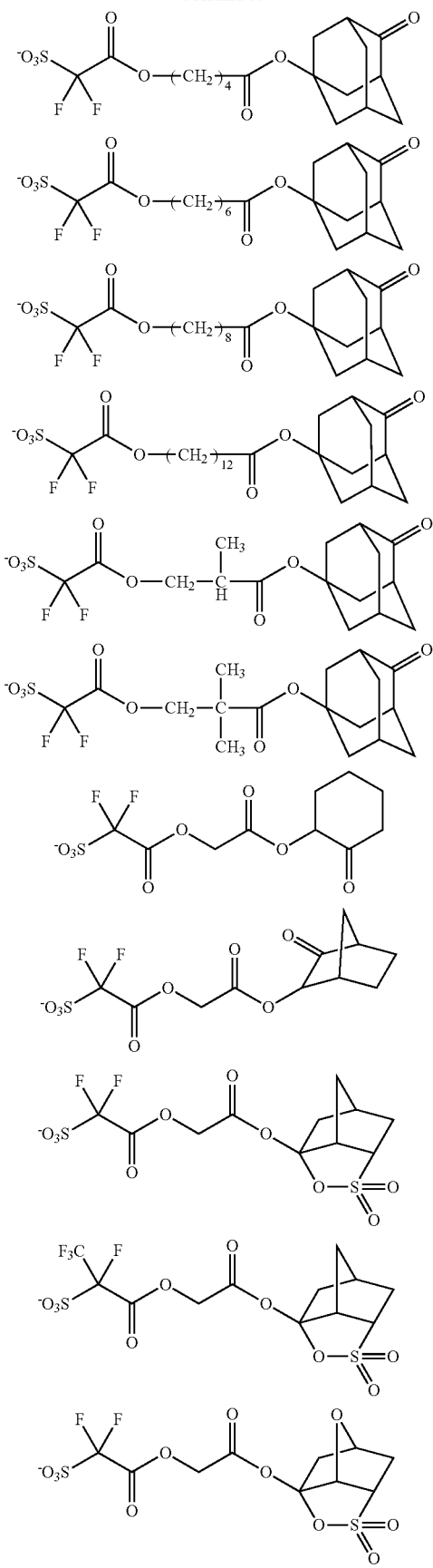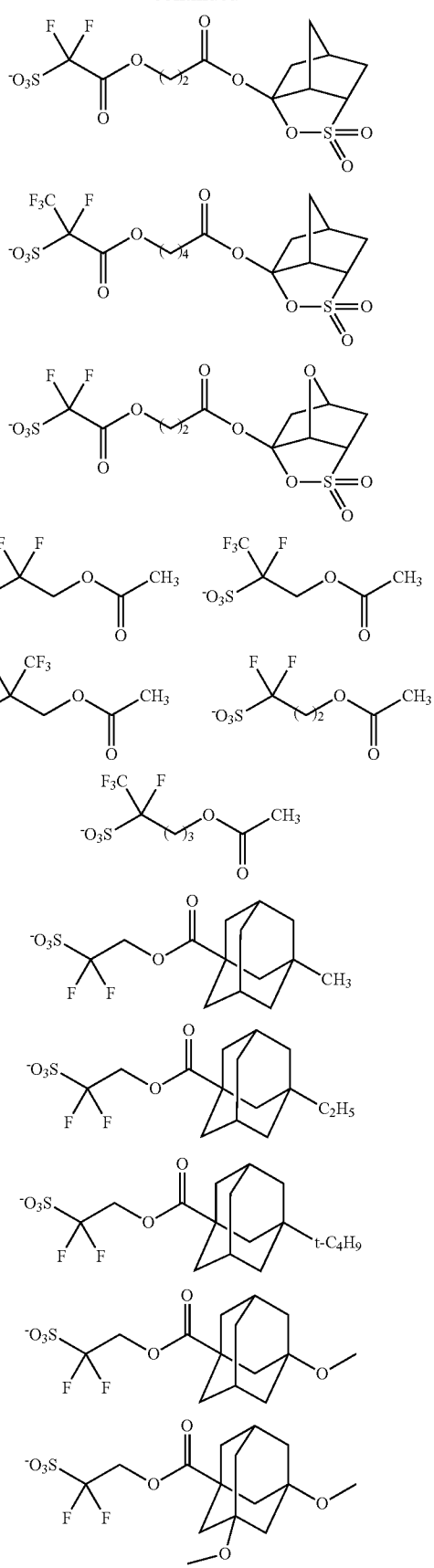

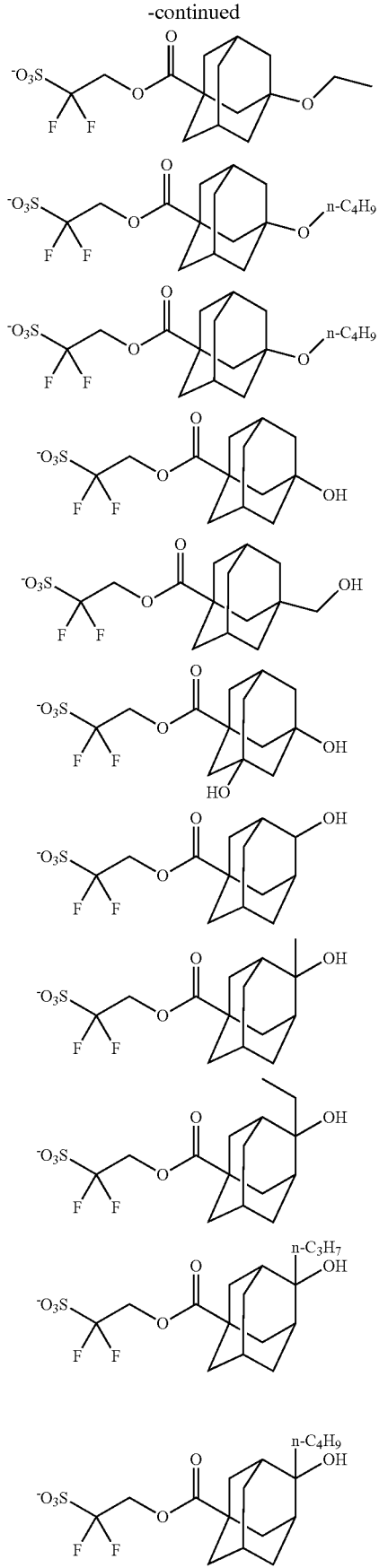

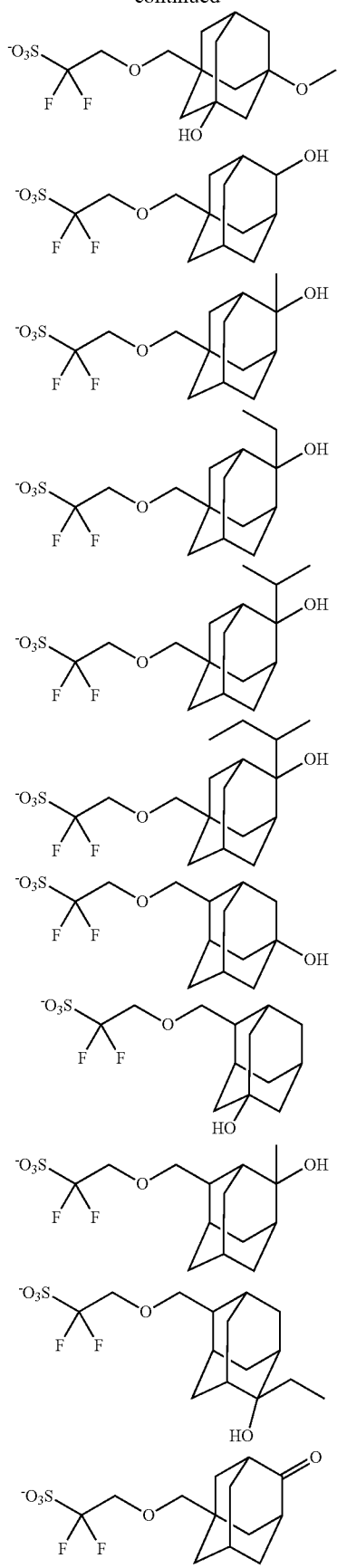

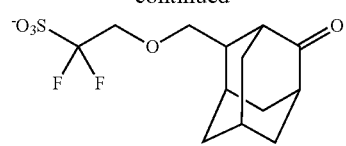

Among them, preferred are the following anions.

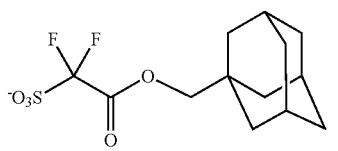

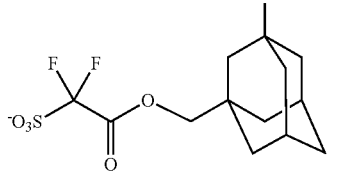

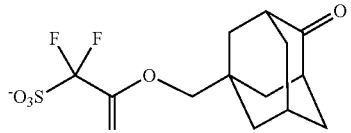

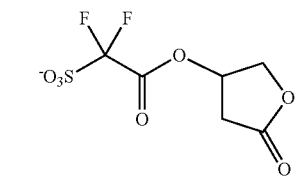

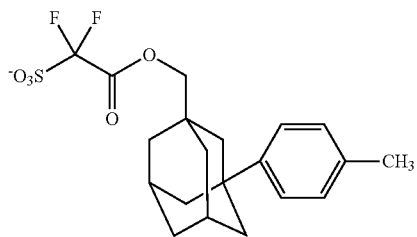

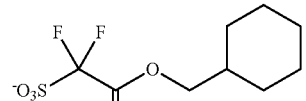

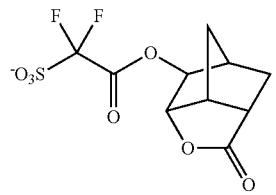

Examples of the cation part represented by $Z^+$ of the salt represented by the formula (B1) include an onium cation such as a sulfonium cation, an iodonium cation, an ammonium cation, a benzothiazolium cation and a phosphonium cation. Among them, preferred are a sulfonium cation and an iodonium cation, and more preferred is an arylsulfonium cation.

Preferable examples of the cation part include the cations represented by the formulae (b2-1) to (b2-4):

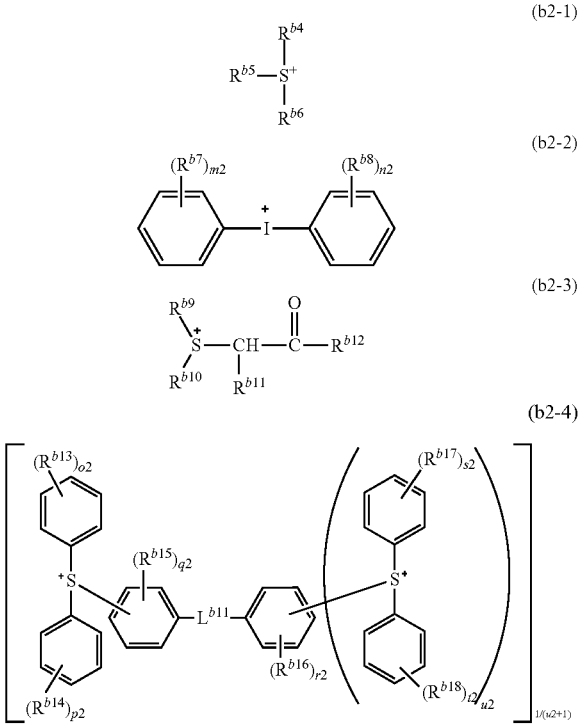

wherein $R^{b4}$, $R^{b5}$ and $R^{b6}$ independently represent a C1-C30 aliphatic hydrocarbon group which can have one or more substituents selected from the group consisting of a hydroxyl group, a C1-C12 alkoxy group and a C6-C18 aromatic hydrocarbon group, a C3-C18 saturated cyclic hydrocarbon group which can have one or more substituents selected from the group consisting of a halogen atom, a C2-C4 acyl group and a glycidyloxy group, or a C6-C18 aromatic hydrocarbon group which can have one or more substituents selected from the group consisting of a halogen atom, a hydroxyl group, a C1-C18 aliphatic hydrocarbon group, a C3-C18 saturated cyclic hydrocarbon group and a C1-C12 alkoxy group, $R^{b7}$ and $R^{b8}$ are independently in each occurrence a hydroxyl group, a C1-C12 aliphatic hydrocarbon group or a C1-C12 alkoxy group, m2 and n2 independently represents an integer of 0 to 5, $R^{b9}$ and $R^{b10}$ independently represent a C1-C18 aliphatic hydrocarbon group or a C3-C18 saturated cyclic hydrocarbon group, or $R^{b9}$ and $R^{b10}$ are bonded to form a C2-C11 divalent acyclic hydrocarbon group which forms a ring together with the adjacent $S^+$, and one or more —$CH_2$— in the divalent acyclic hydrocarbon group may be replaced by —CO—, —O— or —S—, and $R^{b11}$ represents a hydrogen atom, a C1-C18 aliphatic hydrocarbon group, a C3-C18 saturated cyclic hydrocarbon group or a C6-C18 aromatic hydrocarbon group, $R^{b12}$ represents a C1-C12 aliphatic hydrocarbon group, a C3-C18 saturated cyclic hydrocarbon group or a C6-C18 aromatic hydrocarbon group and the aromatic hydrocarbon group can have one or more substituents selected from the group consisting of a C1-C12 aliphatic hydrocarbon group, a C1-C12 alkoxy group, a C3-C18 saturated cyclic hydrocarbon group and a C2-C13 acyloxy group, or $R^{b11}$ and $R^{b12}$ are bonded each other to form a C1-C10 divalent acyclic hydrocarbon group which forms a 2-oxocycloalkyl group together with the adjacent —CHCO—, and one or more —$CH_2$— in the divalent acyclic hydrocarbon group may be replaced by —CO—, —O— or —S—, and $R^{b13}$, $R^{b14}$, $R^{b15}$, $R^{b16}$, $R^{b17}$ and $R^{b18}$ independently represent a hydroxyl group, a C1-C12 aliphatic hydrocarbon group or a C1-C12 alkoxy group, $L^{b11}$ represents —S— or —O— and o2, p2, s2 and t2 each independently, represents an integer of 0 to 5, q2 and r2 each independently represents an integer of 0 to 4, and u2 represents 0 or 1.

The aliphatic hydrocarbon group represented by $R^{b9}$ to $R^{b11}$ has preferably 1 to 12 carbon atoms. The saturated cyclic hydrocarbon group represented by $R^{b9}$ to $R^{b11}$ has preferably 3 to 18 carbon atoms and more preferably 4 to 12 carbon atoms.

Preferable examples of the aliphatic hydrocarbon group include an alkyl group such as a methyl group, an ethyl group, a propyl group, an isopropyl group, a butyl group, a sec-butyl group, a tert-butyl group, a pentyl group, a hexyl group, an octyl group and a 2-ethylhexyl group. Preferable examples of the saturated cyclic hydrocarbon group include a cyclopropyl group, a cyclobutyl group, a cyclopentyl group, a cyclohexyl group, a cycloheptyl group, a cyclodecyl group, a 2-alkyl-a-adamantyl group, a 1-(1-adamantyl)-1-alkyl group and an isobornyl group. Preferable examples of the aromatic group include a phenyl group, a 4-methylphenyl group, a 4-ethylphenyl group, a 4-tert-butylphenyl group, a 4-cyclohexylphenyl group, a 4-methoxyphenyl group, a biphenyl group and a naphthyl group. Examples of the aliphatic hydrocarbon group having an aromatic hydrocarbon group include a benzyl group. Examples of the alkoxy group include a methoxy group, an ethoxy group, a propoxy group, an isopropoxy group, a butoxy group, a sec-butoxy group, a tert-butoxy group, a pentyloxy group, a hexyloxy group, a heptyloxy group, an octyloxy group, a 2-ethylhexyloxy group, a nonyloxy group, a decyloxy group, an undecyloxy group and a dodecyloxy group.

Examples of the C3-C12 divalent acyclic hydrocarbon group formed by bonding $R^{b9}$ and $R^{b10}$ include a trimethylene group, a tetramethylene group and a pentamethylene group. Examples of the ring group formed together with the adjacent $S^+$ and the divalent acyclic hydrocarbon group include a thiolan-1-ium ring (tetrahydrothiphenium ring), a thian-1-ium ring and a 1,4-oxathian-4-ium ring. A C3-C7 divalent acyclic hydrocarbon group is preferable.

Examples of the C1-C10 divalent acyclic hydrocarbon group formed by bonding $R^{b11}$ and $R^{b12}$ include a methylene group, an ethylene group, a trimethylene group, a tetramethylene group and a pentamethylene group and examples of the ring group include the followings.

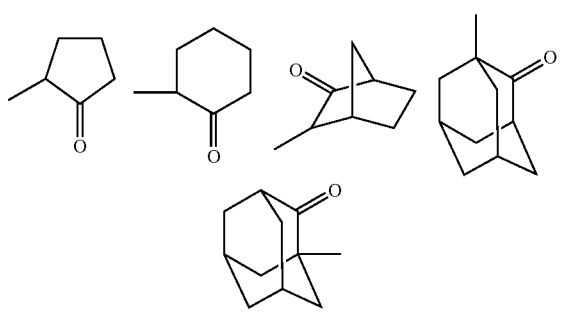

A C1-C5 divalent acyclic hydrocarbon group is preferable.

Among the above-mentioned cations, preferred is the cation represented by the formula (b2-1), and more preferred is the cation represented by the formula (b2-1-1). A triphenylsulfonium cation is especially preferable.

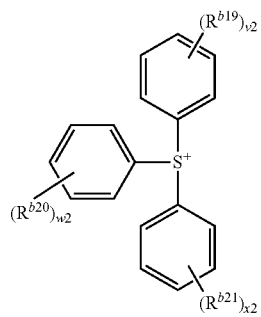

(b2-1-1)

wherein $R^{b19}$, $R^{b20}$ and $R^{b21}$ are independently in each occurrence a halogen atom (preferably a fluorine atom), a hydroxyl group, a C1-C18 aliphatic hydrocarbon group, a C3-C18 saturated cyclic hydrocarbon group or a C1-C12 alkoxy group, and one or more hydrogen atoms of the aliphatic hydrocarbon group can be replaced by a hydroxyl group, a C1-C12 alkoxy group or a C6-C18 aromatic hydrocarbon group, and one or more hydrogen atoms of the saturated cyclic hydrocarbon group can be replaced by a halogen atom, a glycidyloxy group or a C2-C4 acyl group, and v2, w2 and x2 independently each represent an integer of 0 to 5.

The aliphatic hydrocarbon group has preferably 1 to 12 carbon atoms, and the saturated cyclic hydrocarbon group has preferably 4 to 18 carbon atoms, and v2, w2 and x2 independently each preferably represent 0 or 1.

It is preferred that $R^{b19}$, $R^{b20}$ and $R^{b21}$ are independently in each occurrence a halogen atom, a hydroxyl group, a C1-C12 alkyl group or a C1-C12 alkoxy group, and v2, w2 and x2 independently each represent an integer of 0 to 5. It is more preferred that $R^{b19}$, $R^{b20}$ and $R^{b21}$ are independently in each occurrence a fluorine atom, a hydroxyl group, a C1-C12 alkyl group or a C1-C12 alkoxy group, and v2, w2 and x2 independently each represent 0 or 1.

Examples of the cation represented by the formula (b2-1) include the following.

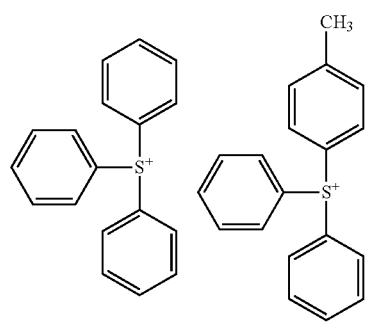

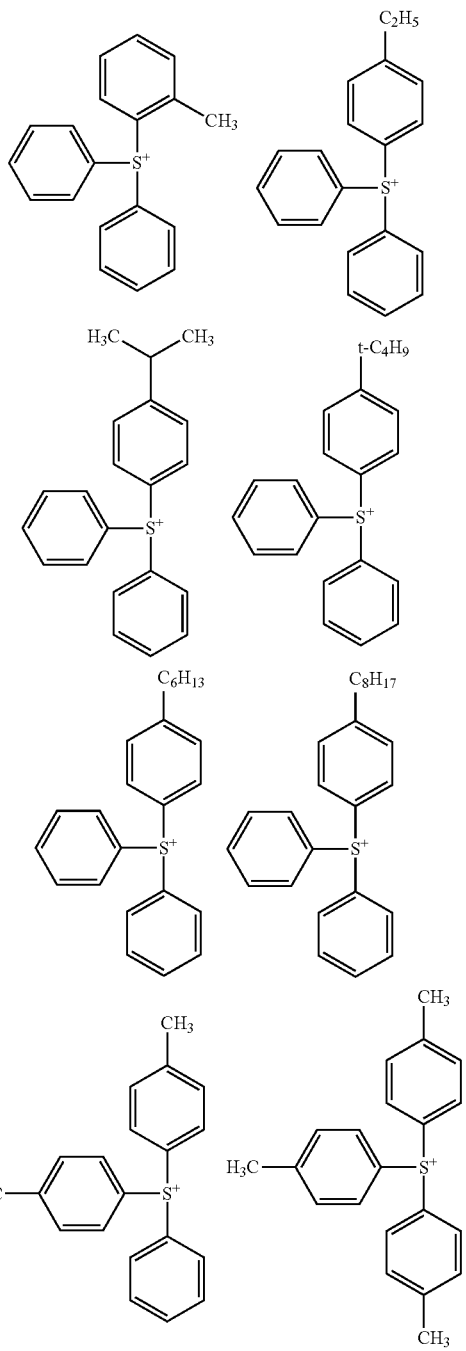

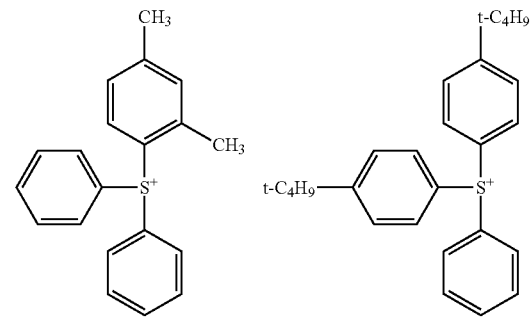

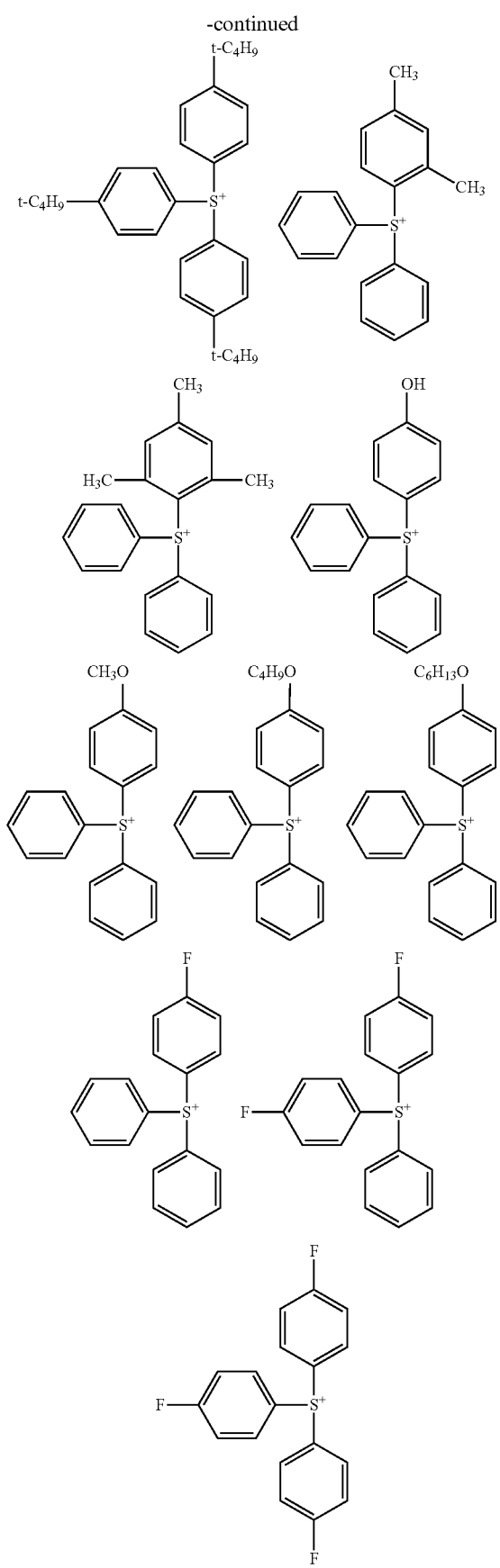
Examples of the cation represented by the formula (b2-2) include the followings.
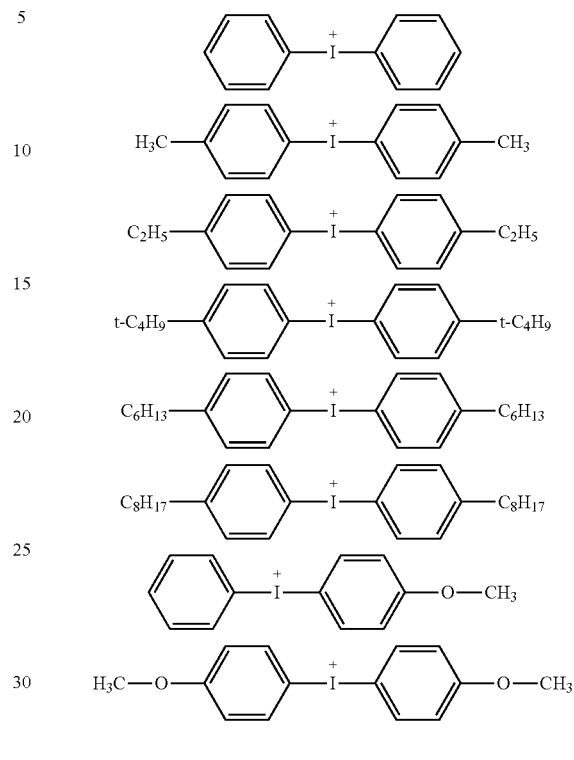
Examples of the cation represented by the formula (b2-3) include the followings.
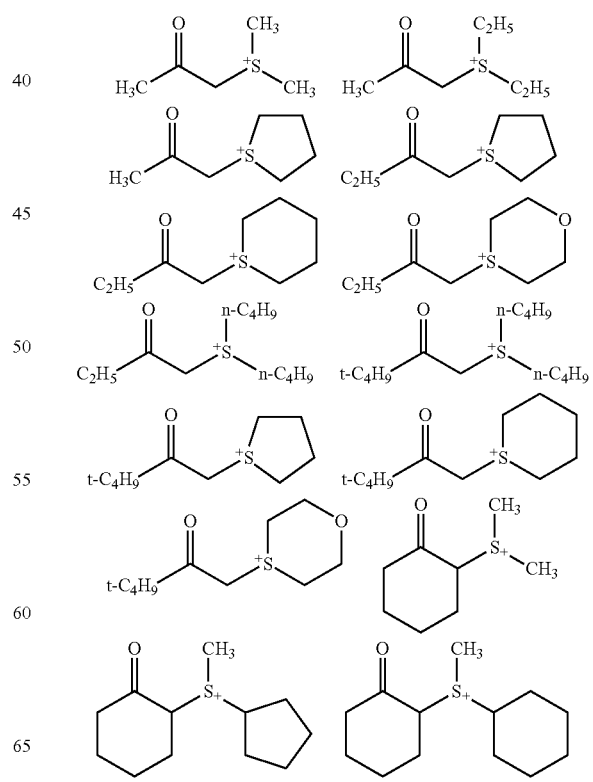

121
-continued
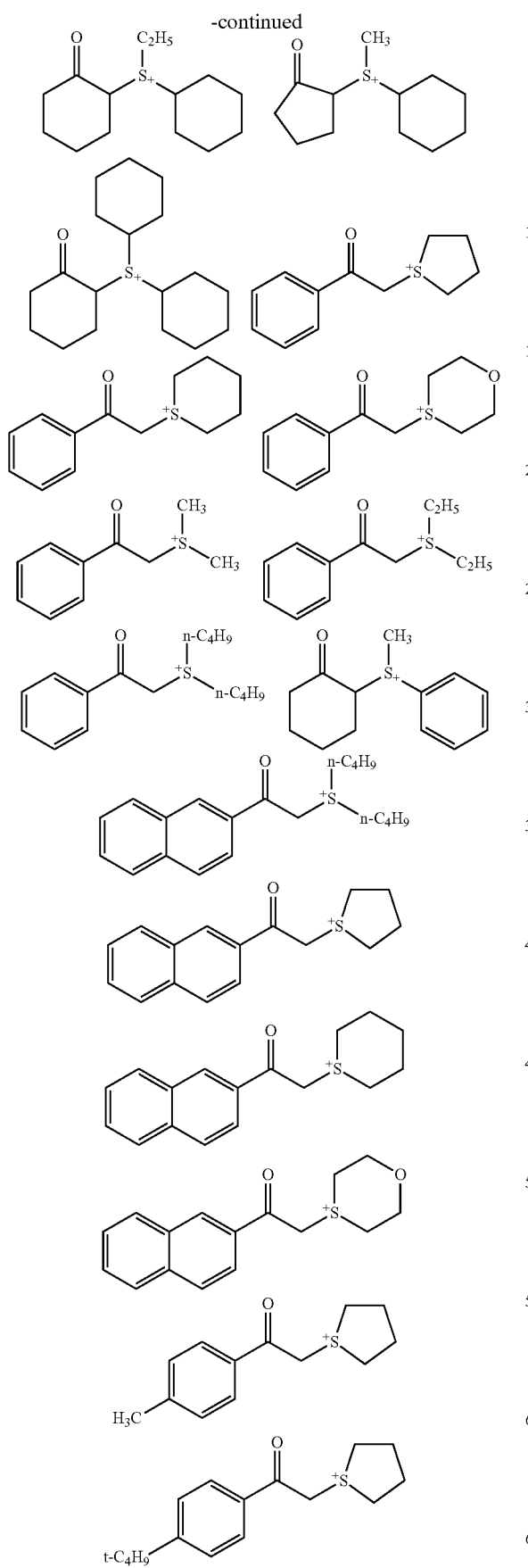
122
-continued
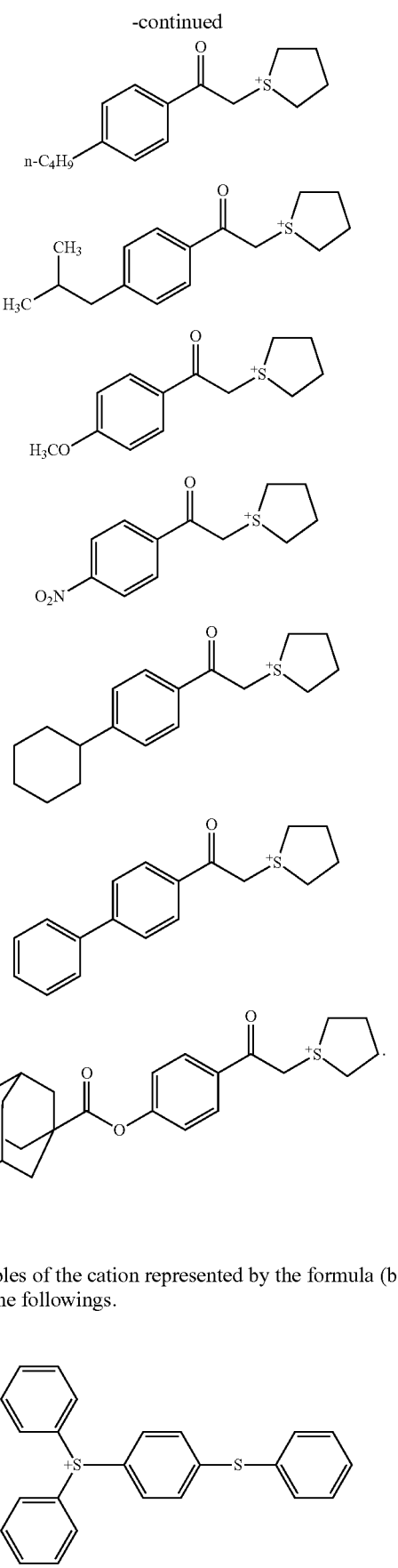
Examples of the cation represented by the formula (b2-4) include the followings.

123
-continued
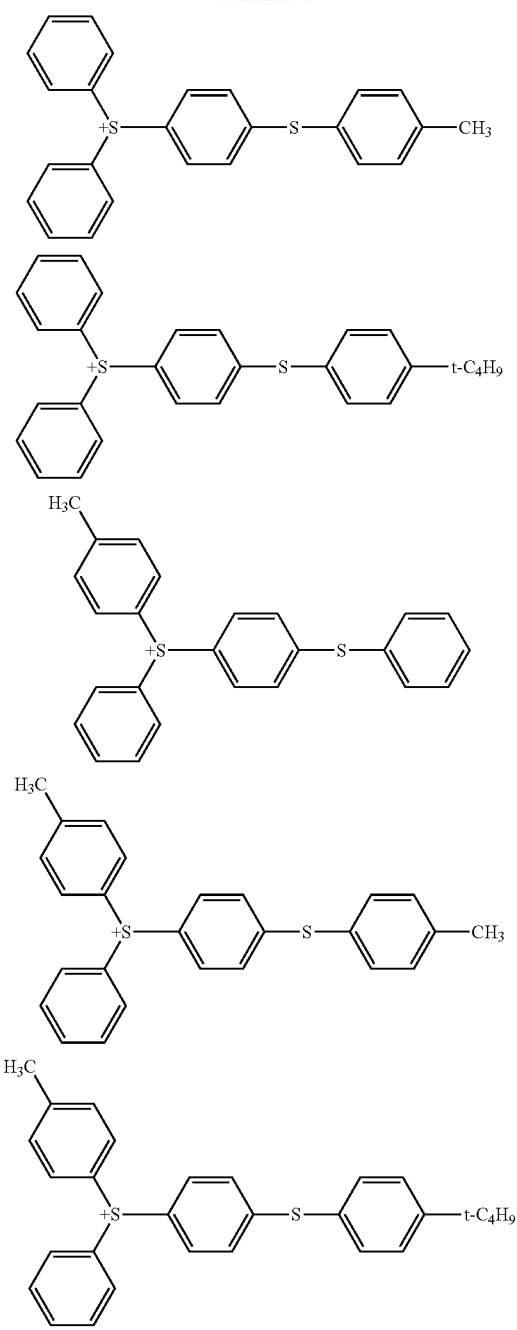
124
-continued
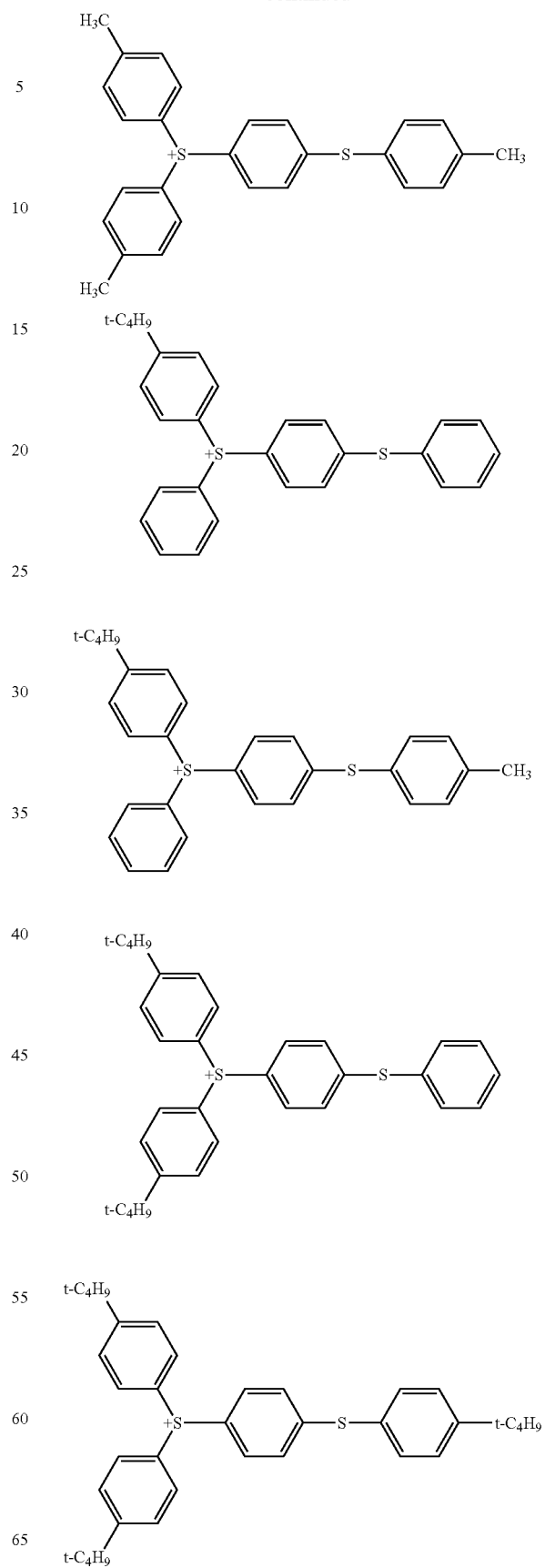

125
-continued
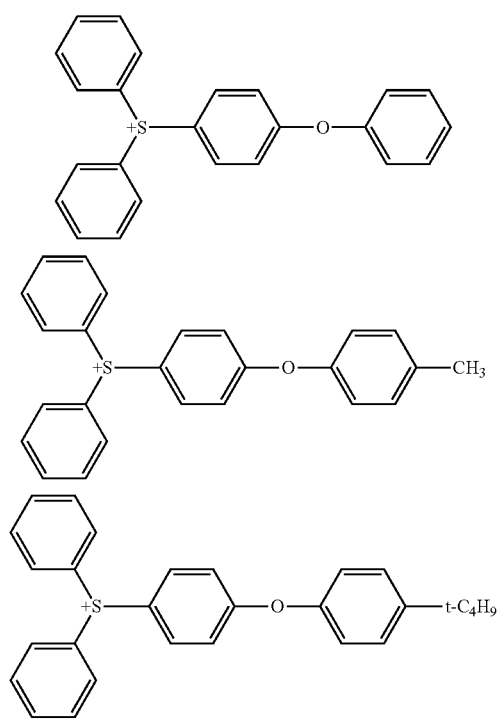
126
-continued
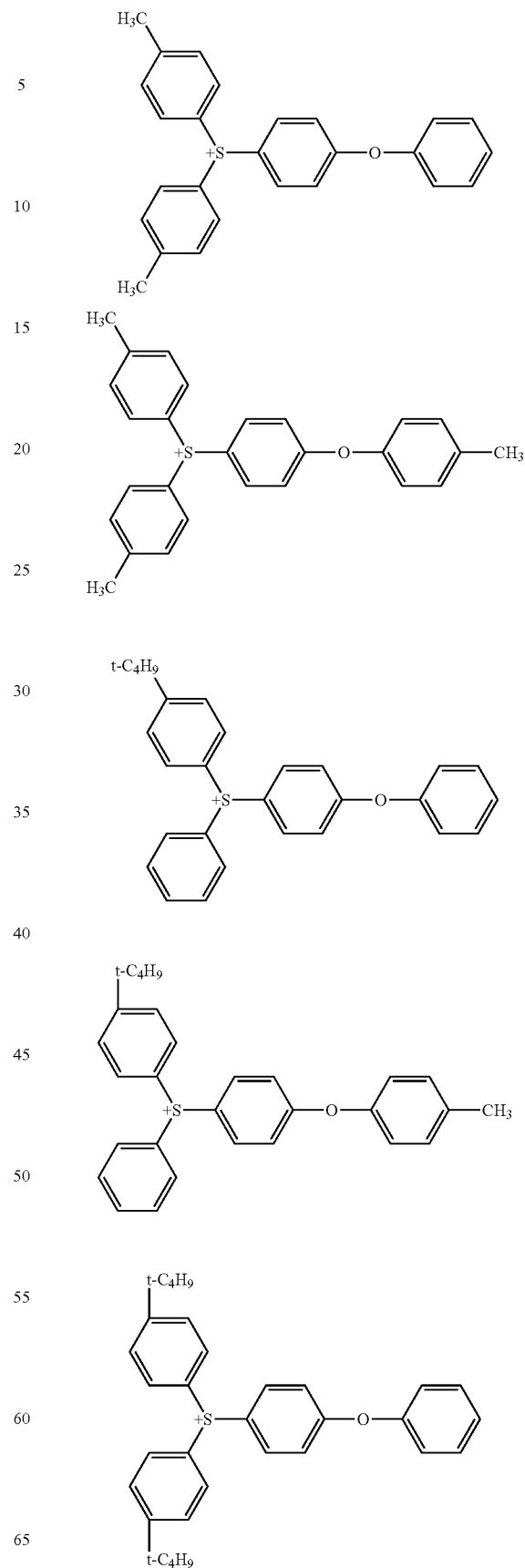

127
-continued
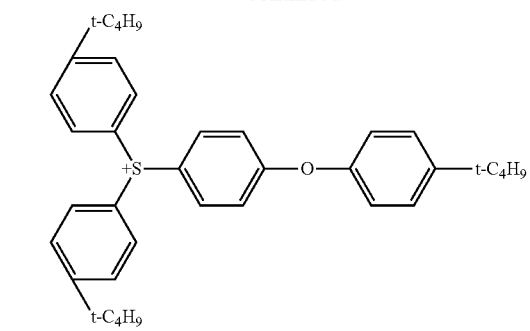
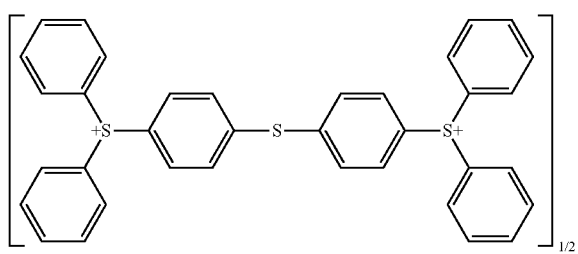
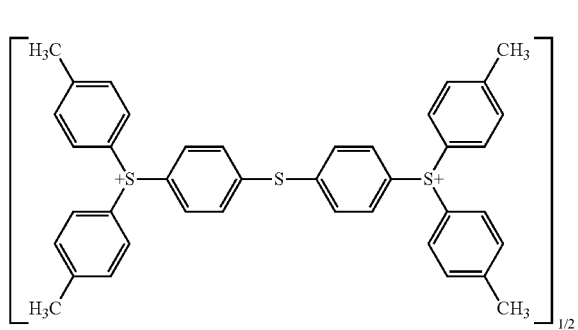
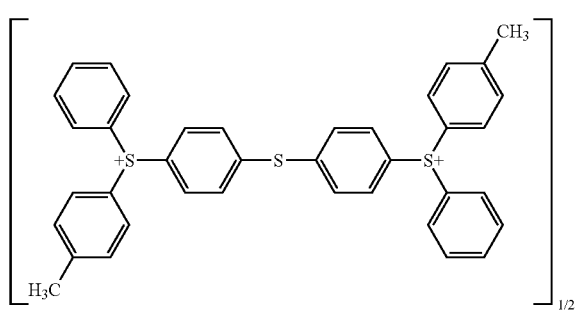
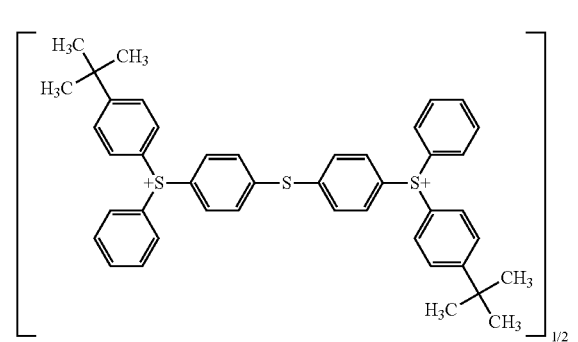
128
-continued
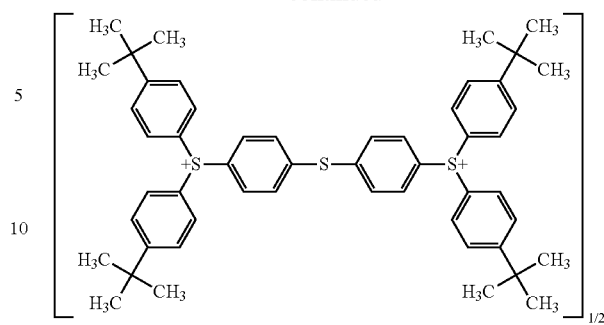
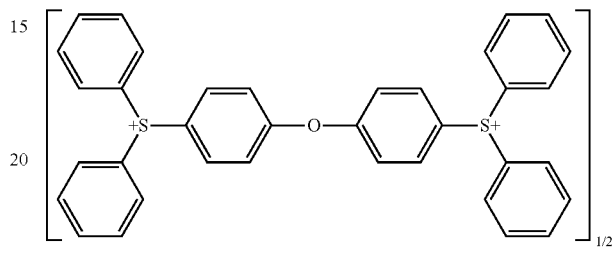
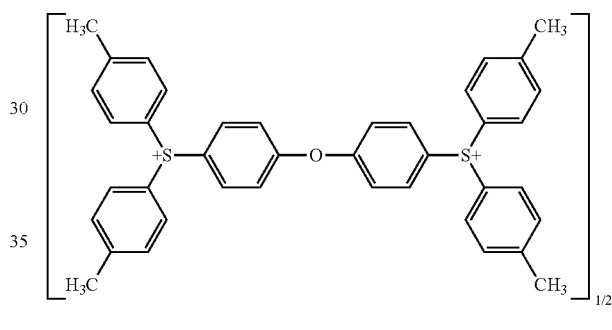
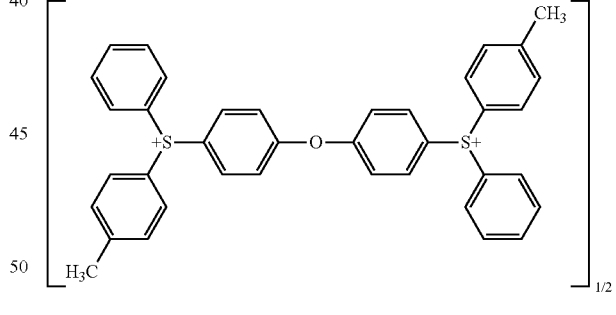
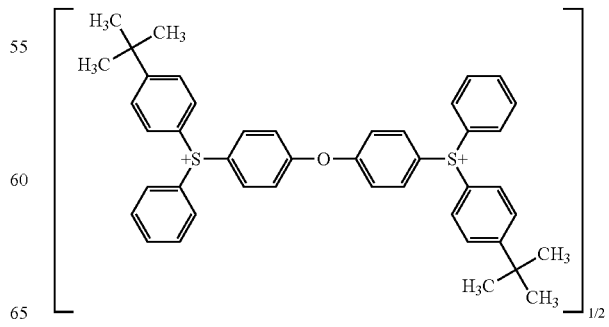

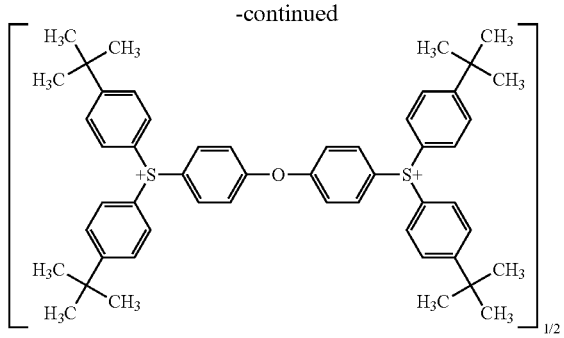

Examples of the salt represented by the formula (B1) include a salt wherein the anion is any one of the above-mentioned anions and the cation is any one of organic cations. Preferable examples of the salt include a combination of any one of anions represented by the formulae (b1-1-1) to (b1-1-9) and the cation represented by the formulae (b2-1-1), and a combination of any one of anions represented by the formulae (b1-1-3) to (b1-1-5) and the cation represented by the formulae (b2-3).

The salt represented by the formulae (B1-1) to (B1-17) are preferable, and the salt represented by the formulae (B1-1), (B1-2), (B1-6), (B1-11), (B1-12), (B1-13) and (B1-14) are more preferable.

(B1-1)

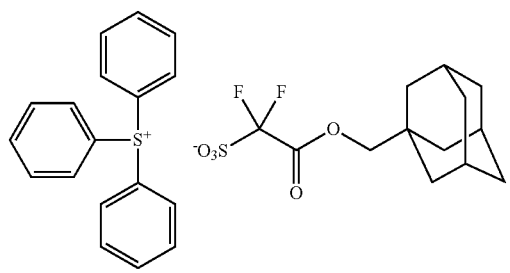

(B1-2)

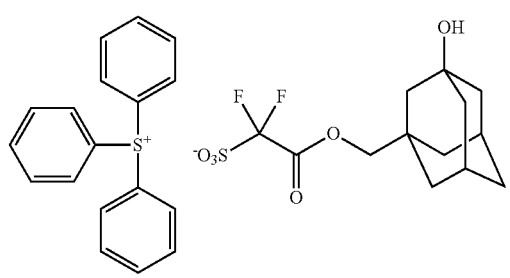

(B1-3)

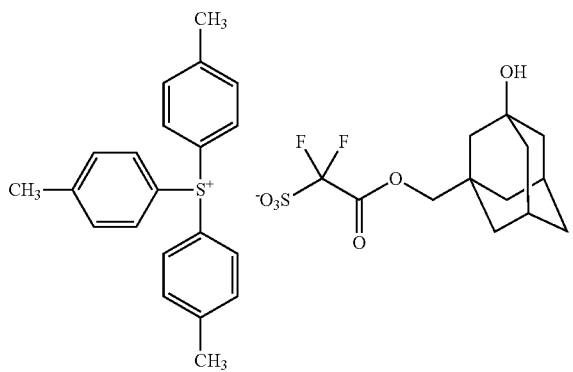

(B1-4)

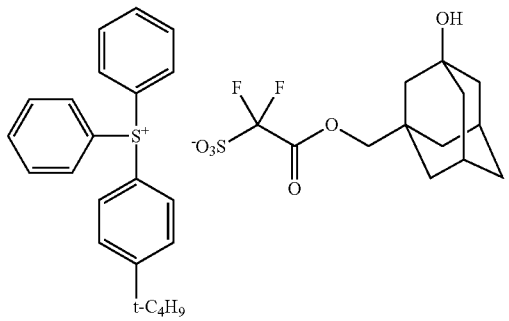

(B1-5)

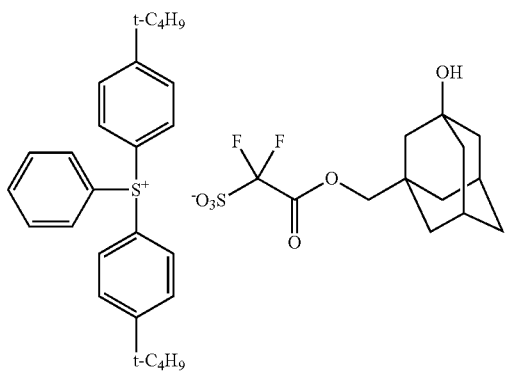

(B1-6)

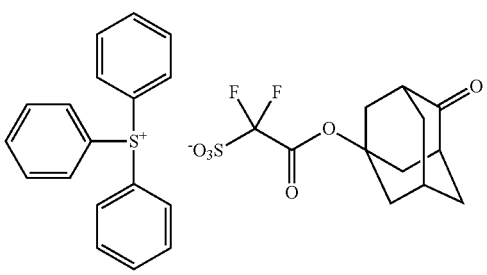

(B1-7)

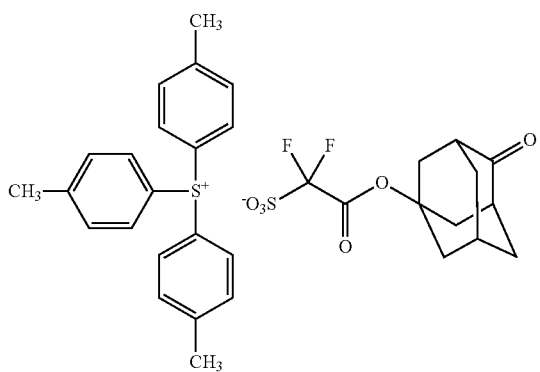

(B1-8)
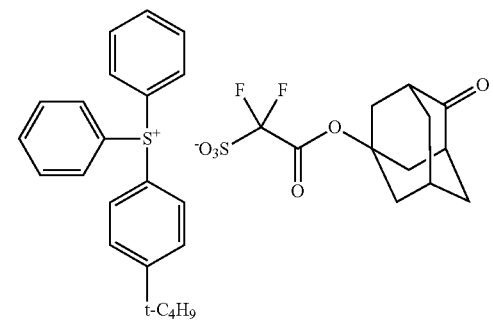

(B1-9)
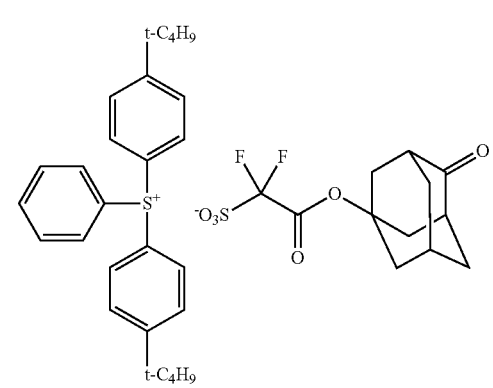

(B1-10)
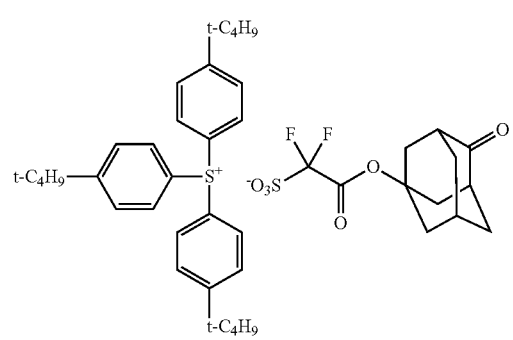

(B1-11)
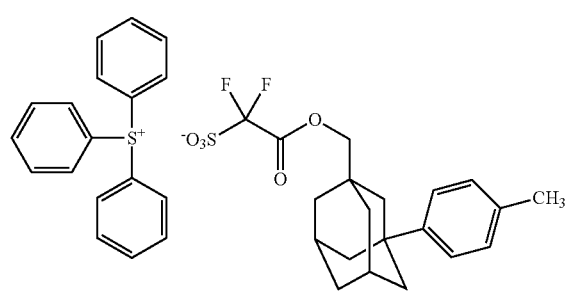

(B1-12)
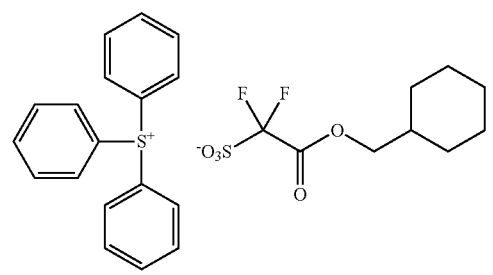

(B1-13)
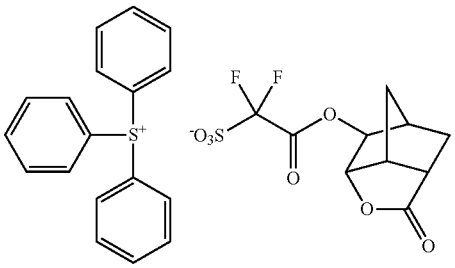

(B1-14)
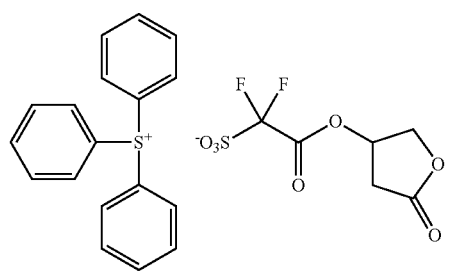

(B1-15)
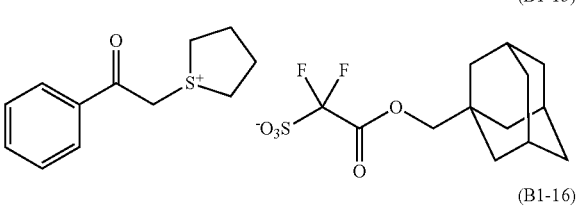

(B1-16)
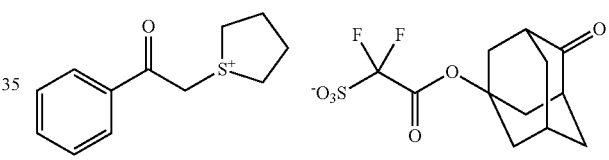

(B1-17)
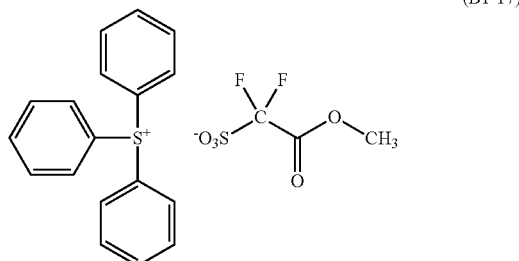

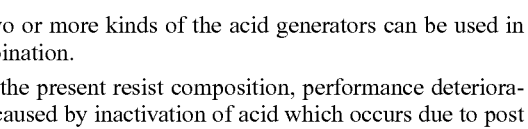

Two or more kinds of the acid generators can be used in combination.

In the present resist composition, performance deterioration caused by inactivation of acid which occurs due to post exposure delay can be diminished by adding a quencher such as a basic compound. The content of the basic compound is usually 0.01 to 1% by weight based on solid component.

The basic compound is preferably an organic base compound, and more preferably a nitrogen-containing organic base compound.

Examples thereof include an amine compound such as an aliphatic amine and an aromatic amine and an ammonium salt. Examples of the aliphatic amine include a primary amine, a secondary amine and a tertiary amine. Examples of the aromatic amine include an aromatic amine in which aromatic ring has one or more amino groups such as aniline and a heteroaromatic amine such as pyridine. Preferable examples thereof include an aromatic amine represented by the formula (C2):

wherein $Ar^{c1}$ represents an aromatic hydrocarbon group, and $R^{c5}$ and $R^{c6}$ each independently represent a hydrogen atom, an aliphatic hydrocarbon group, a saturated cyclic hydrocarbon group or an aromatic hydrocarbon group, and the aliphatic hydrocarbon group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group.

The aliphatic hydrocarbon group is preferably an alkyl group and the saturated cyclic hydrocarbon group is preferably a cycloalkyl group. The aliphatic hydrocarbon group preferably has 1 to 6 carbon atoms. The saturated cyclic hydrocarbon group preferably has 5 to 10 carbon atoms. The aromatic hydrocarbon group preferably has 6 to 10 carbon atoms.

As the aromatic amine represented by the formula (C2), an amine represented by the formula (C2-1):

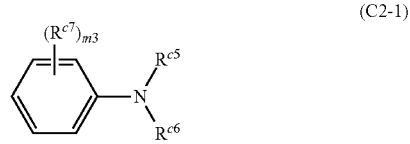

wherein $R^{c5}$ and $R^{c6}$ are the same as defined above, and $R^{c7}$ is independently in each occurrence an aliphatic hydrocarbon group, an alkoxy group, a saturated cyclic hydrocarbon group or an aromatic hydrocarbon group, and the aliphatic hydrocarbon group, the alkoxy group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, and m3 represents an integer of 0 to 3, is preferable. The aliphatic hydrocarbon group is preferably an alkyl group and the saturated cyclic hydrocarbon group is preferably a cycloalkyl group. The aliphatic hydrocarbon group preferably has 1 to 6 carbon atoms. The saturated cyclic hydrocarbon group preferably has 5 to 10 carbon atoms. The aromatic hydrocarbon group preferably has 6 to 10 carbon atoms. The alkoxy group preferably has 1 to 6 carbon atoms.

An ammonium salt represented by the formula (C2-2):

wherein $R^{c8'}$, $R^{c9'}$, $R^{c10'}$ and $R^{c11'}$ each independently represent an aliphatic hydrocarbon group, a saturated cyclic hydrocarbon group or an aromatic hydrocarbon group, and the aliphatic hydrocarbon group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, and $An^-$ represents $OH^-$, is also preferable. The aliphatic hydrocarbon group is preferably an alkyl group and the saturated cyclic hydrocarbon group is preferably a cycloalkyl group. The aliphatic hydrocarbon group preferably has 1 to 8 carbon atoms. The saturated cyclic hydrocarbon group preferably has 5 to 10 carbon atoms. The aromatic hydrocarbon group preferably has 6 to 10 carbon atoms. The alkoxy group preferably has 1 to 6 carbon atoms.

Examples of the aromatic amine represented by the formula (C2) include 1-naphthylamine, 2-naphthylamine, aniline, diisopropylaniline, 2-methylaniline, 3-methylaniline, 4-methylaniline, 4-nitroaniline, N-methylaniline, N,N-dimethylaniline, and diphenylamine, and among them, preferred is diisopropylaniline and more preferred is 2,6-diisopropylaniline. Examples of the ammonium salt represented by the formula (C2-C2) include tetramethylammonium hydroxide and tetrabutylammonium hydroxide.

Other examples of the basic compound include amines represented by the formulae (C3) to (C11):

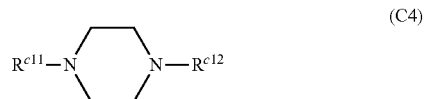

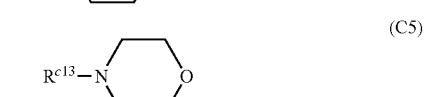

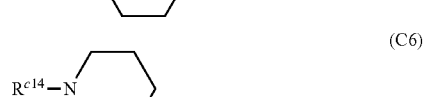

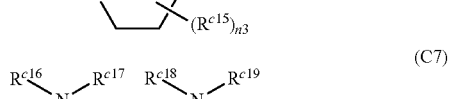

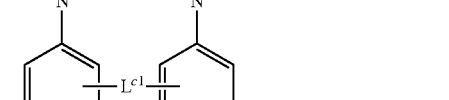

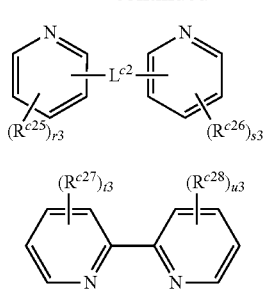

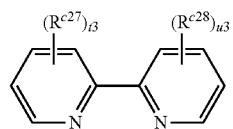

wherein $R^{c8}$, $R^{c20}$, $R^{c21}$, and $R^{c23}$ to $R^{c28}$ each independently represent an aliphatic hydrocarbon group, an alkoxy group, a saturated cyclic hydrocarbon group or an aromatic hydrocarbon group, and the aliphatic hydrocarbon group, the alkoxy group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group,
$R^{c9}$, $R^{c10}$, $R^{c11}$ to $R^{c14}$, $R^{c16}$ to $R^{c19}$, and $R^{c22}$ each independently represents a hydrogen atom, an aliphatic hydrocarbon group, a saturated cyclic hydrocarbon group or an aromatic hydrocarbon group, and the aliphatic hydrocarbon group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group,
$R^{c15}$ is independently in each occurrence an aliphatic hydrocarbon group, a saturated cyclic hydrocarbon group or an alkanoyl group,
$L^{c1}$ and $L^{c2}$ each independently represents a divalent aliphatic hydrocarbon group, —CO—, —C(=NH)—, —C(=NR$^{c3}$)—, —S—, —S—S— or a combination thereof and $R^{c3}$ represents a C1-C4 alkyl group,
O3 to u3 each independently represents an integer of 0 to 3 and n3 represents an integer of 0 to 8.

The aliphatic hydrocarbon group has preferably 1 to 6 carbon atoms, and the saturated cyclic hydrocarbon group has preferably 3 to 6 carbon atoms, and the alkanoyl group has preferably 2 to 6 carbon atoms, and the divalent aliphatic hydrocarbon group has preferably 1 to 6 carbon atoms. The divalent aliphatic hydrocarbon group is preferably an alkylene group.

Examples of the amine represented by the formula (C3) include hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethydipentylamine, ethyldihexylamine, ethydiheptylamine, ethyldioctylamine, ethyldinonylamine, ethyldidecylamine, dicyclohexylmethylamine, tris[2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane and 4,4'-diamino-3,3'-diethyldiphenylmethane.

Examples of the amine represented by the formula (C4) include piperazine. Examples of the amine represented by the formula (C5) include morpholine. Examples of the amine represented by the formula (C6) include piperidine and hindered amine compounds having a piperidine skeleton as disclosed in JP 11-52575 A. Examples of the amine represented by the formula (C7) include 2,2'-methylenebisaniline. Examples of the amine represented by the formula (C8) include imidazole and 4-methylimidazole. Examples of the amine represented by the formula (C9) include pyridine and 4-methylpyridine. Examples of the amine represented by the formula (C10) include di-2-pyridyl ketone, 1,2-di(2-pyridyl)ethane, 1,2-di(4-pyridyl)ethane, 1,3-di(4-pyridyl) propane, 1,2-bis(2-pyridyl)ethene, 1,2-bis(4-pyridyl)ethene, 1,2-di(4-pyridyloxy)ethane, 4,4'-dipyridyl sulfide, 4,4'-dipyridyl disulfide, 2,2'-dipyridylamine and 2,2'-dipicolylamine. Examples of the amine represented by the formula (C11) include bipyridine.

The photoresist composition of the present invention usually contains one or more solvents. Examples of the solvent include a glycol ether ester such as ethyl cellosolve acetate, methyl cellosolve acetate and propylene glycol monomethyl ether acetate; a glycol ether such as propylene glycol monomethyl ether; an acyclic ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone.

The amount of the solvent is usually 90% by weight or more, preferably 92% by weight or more preferably 94% by weight or more based on total amount of the photoresist composition of the present invention. The amount of the solvent is usually 99.9% by weight or less based on total amount of the photoresist composition of the present invention. The photoresist composition containing a solvent can be preferably used for producing a thin layer photoresist pattern.

The photoresist composition of the present invention can contain, if necessary, a small amount of various additives such as a sensitizer, a dissolution inhibitor, other polymers, a surfactant, a stabilizer and a dye as long as the effect of the present invention is not prevented.

A photoresist pattern can be produced by the following steps (1) to (5):
(1) a step of applying the photoresist composition of the present invention on a substrate,
(2) a step of forming a photoresist film by conducting drying,
(3) a step of exposing the photoresist film to radiation,
(4) a step of baking the exposed photoresist film, and
(5) a step of developing the baked photoresist film with an alkaline developer, thereby forming a photoresist pattern.

The applying of the photoresist composition on a substrate is usually conducted using a conventional apparatus such as spin coater.

The formation of the photoresist film is usually conducted using a heating apparatus such as hot plate or a decompressor, and the heating temperature is usually 50 to 200° C., and the operation pressure is usually 1 to $1.0*10^5$ Pa.

The photoresist film obtained is exposed to radiation using an exposure system. The exposure is usually conducted through a mask having a pattern corresponding to the desired photoresist pattern. Examples of the exposure source include a light source radiating laser light in a UV-region such as a KrF excimer laser (wavelength: 248 nm), an ArF excimer laser (wavelength: 193 nm) and a $F_2$ laser (wavelength: 157 nm), and a light source radiating harmonic laser light in a far UV region or a vacuum UV region by wavelength conversion of laser light from a solid laser light source (such as YAG or semiconductor laser).

The temperature of baking of the exposed photoresist film is usually 50 to 200° C., and preferably 70 to 150° C.

The development of the baked photoresist film is usually carried out using a development apparatus. The alkaline developer used may be any one of various alkaline aqueous solution used in the art. Generally, an aqueous solution of tetramethylammonium hydroxide or (2-hydroxyethyl)trimethylammoniumhydroxide (commonly known as "choline") is often used. After development, the photoresist pattern formed is preferably washed with ultrapure water, and the remained water on the photoresist pattern and the substrate is preferably removed.

The photoresist composition of the present invention provides a photoresist pattern showing good line edge roughness and exposure latitude, and therefore, the photoresist composition of the present invention is suitable for ArF excimer laser lithography, KrF excimer laser lithography, ArF immersion lithography, EUV (extreme ultraviolet) lithography, EUV immersion lithography and EB (electron beam) lithography.

EXAMPLES

The present invention will be described more specifically by Examples, which are not construed to limit the scope of the present invention.

The "%" and "part(s)" used to represent the content of any component and the amount of any material used in the following examples and comparative examples are on a weight basis unless otherwise specifically noted. The weight-average molecular weight of any material used in the following examples is a value found by gel permeation chromatography [HLC-8120GPC Type, Column (Three Columns with guard column): TSKgel Multipore $H_{XL}$-M, manufactured by TOSOH CORPORATION, Solvent: Tetrahydrofuran, Flow rate: 1.0 mL/min., Detector: RI detector, Column temperature: 40° C., Injection volume: 100 µL] using standard polystyrene as a standard reference material manufactured by TOSOH CORPORATION. Structures of compounds were determined by NMR (ECA-500 Type, manufactured by JEOL LTD.) and mass spectrometry (JMS-700, manufactured by JEOL LTD.).

Example 1

Synthesis of Compound Represented by the Formula (I-1)

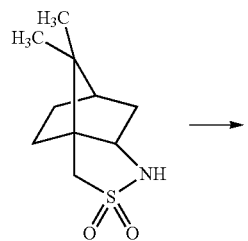

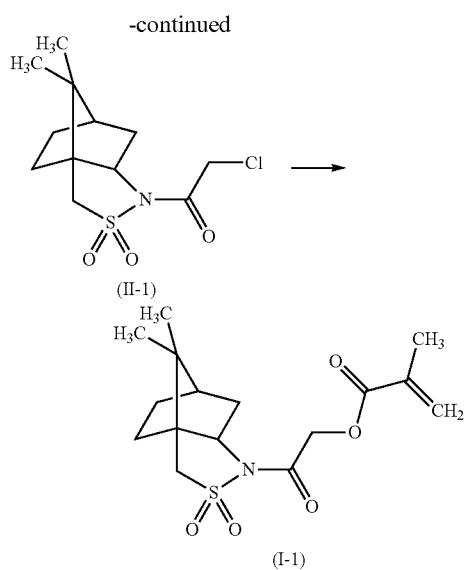

To a four-necked flask equipped with a condenser and a stirrer, 16.89 parts of sodium hydride and 152 parts of toluene were added. The resultant mixture was adjusted at the inner temperature of 23° C. To the mixture, a solution prepared by dissolving 55.56 parts of (−)-2,10-camphorsultam in 345 parts of toluene was added dropwise over 1 hour. To the resultant mixture, a solution prepared by diluting 34.97 parts of chloroacetyl chloride with 108 parts of toluene was added dropwise over 1 hour. The mixture obtained was stirred for 6 hours. To the reaction mixture obtained, 305 parts of water was added followed by extracting with 457 parts of ethyl acetate.

The organic layer obtained was washed with 152 parts of 1M aqueous saturated sodium hydrogen carbonate solution and then with 251 parts of aqueous sodium chloride solution. The organic layer was dried over magnesium sulfate. After drying, the organic layer was concentrated and the residue was purified with silica gel chromatography (developing solvent: heptane and ethyl acetate) to obtain 58.67 parts of the compound represented by the formula (II-1).

$^1$H-NMR (500.16 MHz, CDCl$_3$): δ 0.98 (s, 3H), 1.15 (s, 3H), 1.35-1.47 (m, 2H), 1.87-1.97 (m, 3H), 2.10 (q, J=7.65 Hz, 1H), 2.15-2.20 (m, 1H), 3.52 (q, J=13.75 Hz, 2H), 3.90 (q, J=5.35 Hz, 1H), 4.50 (s, 2H)

$^{13}$C-NMR (125.77 MHz, CDCl$_3$): δ 19.78, 20.66, 26.31, 32.69, 37.93, 42.29, 44.46, 47.81, 49.11, 52.60, 65.40, 164.59

FD-MS: calculated 291.07, measured 291

To a four-necked flask equipped with a condenser and a stirrer, 25.95 parts of methacrylic acid and 259 parts of N,N-dimethylformamide were added. To the resultant mixture, 41.65 parts of potassium carbonate and 12.51 parts of potassium iodide were added, and then, the resultant mixture was heated up to 50° C. To the mixture, a solution prepared by dissolving 58.63 parts of the compound represented by the formula (II-1) in 120 parts of N,N-dimethylformamide was added dropwise over 1 hour. The resultant mixture was stirred for 6 hours. To the reaction mixture obtained, 520 parts of water and 390 parts of ethyl acetate were added, and then, the extraction was conducted. The organic layer obtained was washed with 520 parts of water. The organic layer was dried over magnesium sulfate. After drying, the organic layer was concentrated and the residue was purified with silica gel chromatography (developing solvent: heptane and ethyl acetate) to obtain 67.24 parts of the compound represented by the formula (I-1).

$^1$H-NMR (500.16 MHz, CDCl$_3$): δ 0.98 (s, 3H), 1.17 (s, 3H), 1.35 (q, J=9.20 Hz, 1H), 1.46 (t, J=9.20 Hz, 1H), 1.88-1.95 (m, 3H), 1.97 (s, 3H), 2.05 (d, J=8.45 Hz, 1H), 2.17-2.22 (m, 1H), 3.53 (q, J=13.75 Hz, 2H), 3.89 (q, J=4.55 Hz, 1H), 5.06 (s, 2H), 5.65 (d, J=1.55 Hz, 1H), 6.21 (s, 1H)

$^{13}$C-NMR (125.77 MHz, CDCl$_3$): δ 17.82, 19.41, 20.32, 20.54, 23.61, 26.01, 28.84, 32.26, 37.60, 44.22, 47.47, 49.13, 52.05, 61.66, 64.50, 126.35, 134.97, 165.43, 165.89

FD-MS: calculated 341.13, measured 342

In the following Examples, Monomer (A), Monomer (B), Monomer (C), Monomer (D) and Monomer (1-1) represented by the followings were used.

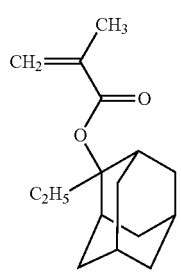
(A)

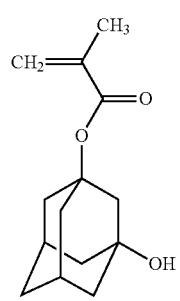
(B)

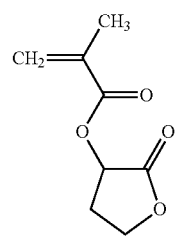
(C)

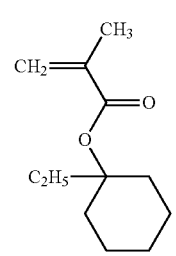
(D)

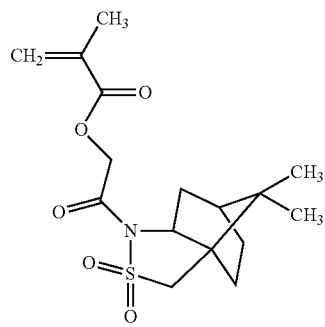
(I-1)

Example 2

Synthesis of Resin A1

To a four-necked flask equipped with a condenser and a stirrer, Monomer (A), Monomer (B), Monomer (C), Monomer (D) and Monomer (I-1) were mixed in a molar ratio of 25/3/43/14/15 (Monomer (A)/Monomer (B)/Monomer (C)/Monomer (D)/Monomer (I-1)), and 1,4-dioxane in 1.5 times part based on total parts of all monomers was added thereto to prepare a solution. To the solution obtained, azobisisobutyronitrile as an initiator in a ratio of 0.8 mol % based on all monomer molar amount and azobis(2,4-dimethylvaleronitrile) as an initiator in a ratio of 2.4 mol % based on all monomer molar amount were added, and the obtained mixture was heated at 66° C. for about 5 hours. The reaction mixture obtained was poured into a mixture of a large amount of methanol and water to cause precipitation, and this operation was further repeated twice for purification. As a result, a resin having a weight-average molecular weight of 1.6×10$^4$ was obtained in a yield of 74%. The resin had the following structural units. This is called as resin A1.

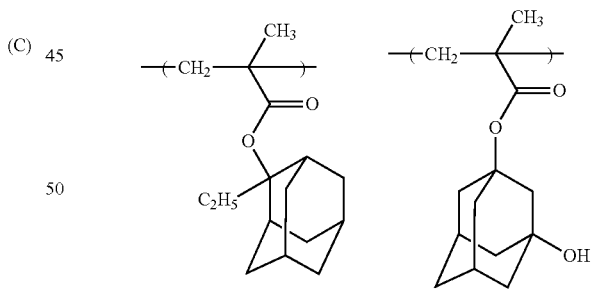

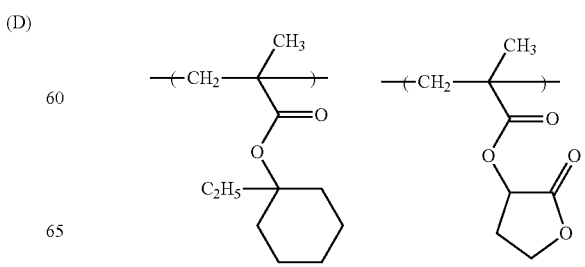

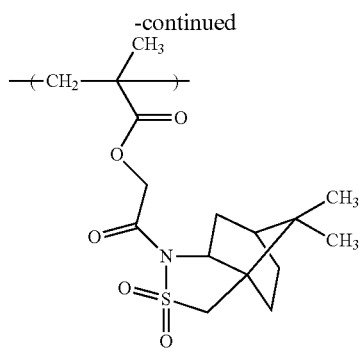

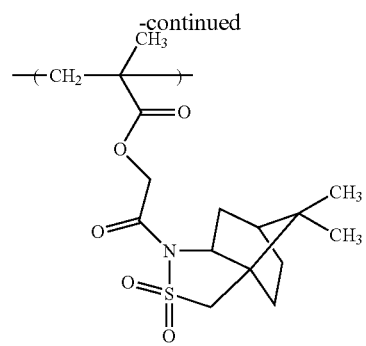

Example 3

Synthesis of Resin A2

To a four-necked flask equipped with a condenser and a stirrer, Monomer (A), Monomer (B), Monomer (C), Monomer (D) and Monomer (I-1) were mixed in a molar ratio of 25/3/45/18/9 (Monomer (A)/Monomer (B)/Monomer (C)/Monomer (D)/Monomer (I-1)), and 1,4-dioxane in 1.5 times part based on total parts of all monomers was added thereto to prepare a solution. To the solution obtained, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 75° C. for about 5 hours. The reaction mixture obtained was poured into a mixture of a large amount of methanol and water to cause precipitation, and this operation was further repeated twice for purification. As a result, a resin having a weight-average molecular weight of $8.2 \times 10^3$ was obtained in a yield of 71%. The resin had the following structural units. This is called as resin A2.

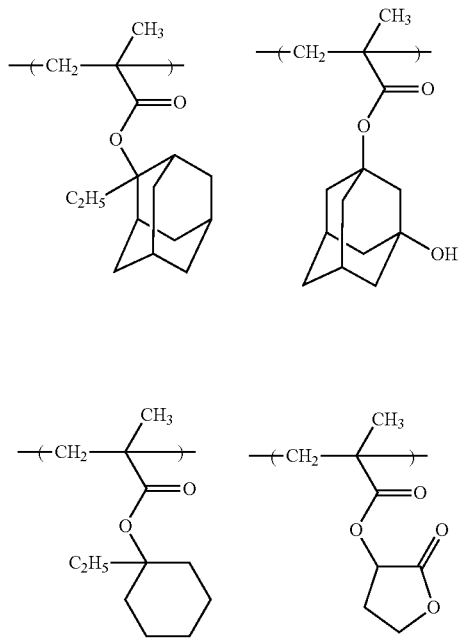

Example 4

Synthesis of Resin A3

To a four-necked flask equipped with a condenser and a stirrer, Monomer (A), Monomer (C), Monomer (D) and Monomer (I-1) were mixed in a molar ratio of 25/45/18/12 (Monomer (A)/Monomer (C)/Monomer (D)/Monomer (I-1)), and 1,4-dioxane in 1.5 times part based on total parts of all monomers was added thereto to prepare a solution. To the solution obtained, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 75° C. for about 5 hours. The reaction mixture obtained was poured into a mixture of a large amount of methanol and water to cause precipitation, and this operation was further repeated twice for purification. As a result, a resin having a weight-average molecular weight of $8.5 \times 10^3$ was obtained in a yield of 71%. The resin had the following structural units. This is called as resin A3.

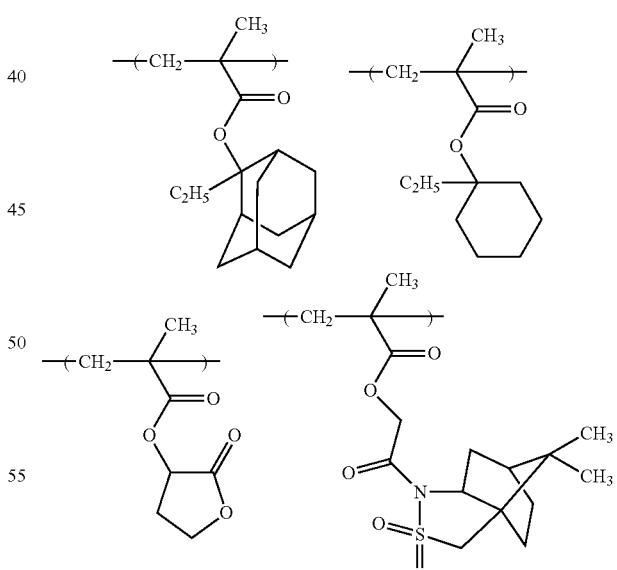

Comparative Resin Synthesis Example 1

Synthesis of Resin H1

To a four-necked flask equipped with a condenser and a thermometer, Monomer (A), Monomer (B) and Monomer (C)

were mixed in a molar ratio of 50/25/25 (Monomer (A)/Monomer (B)/Monomer (C)), and 1,4-dioxane in 1.5 times part based on total parts of all monomers was added thereto to prepare a solution. To the solution obtained, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 77° C. for about 5 hours. The reaction mixture obtained was poured into a mixture of a large amount of methanol and water (methanol/water=3/1) to cause precipitation, and this operation was further repeated twice for purification. As a result, a resin having a weight-average molecular weight of about $8.0 \times 10^3$ was obtained in a yield of 60%. The resin had the following structural units. This is called as resin H1.

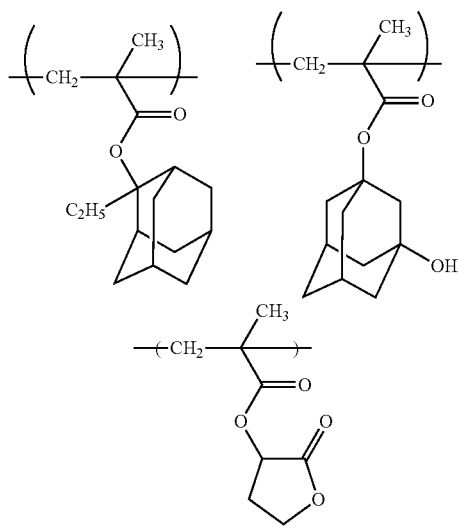

Examples 5 to 7 and Comparative Example 1

Resin

A1: Resin A1
A2: Resin A2
A3: Resin A3
H1: Resin H1

<Acid Generator>

B1:

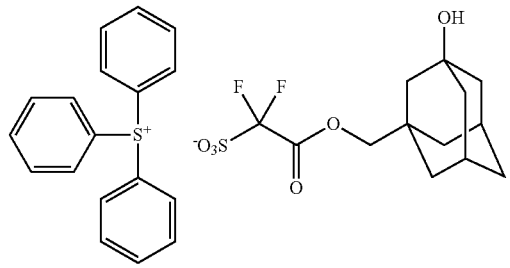

B2:

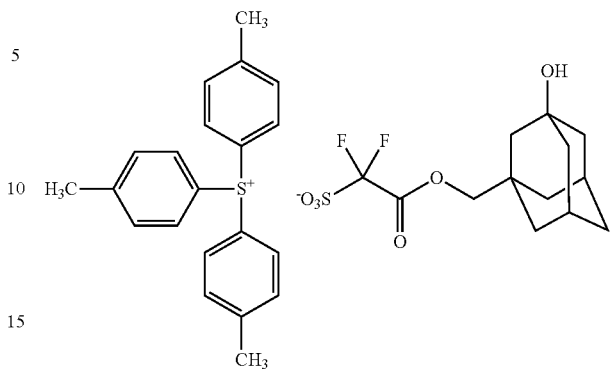

<Basic Compound (Quencher)>
C1: 2,6-diisopropylaniline

<Solvent>

| Y1: | propylene glycol monomethyl ether acetate | 280 parts |
| | 2-heptanone | 20 parts |
| | propylene glycol monomethyl ether | 20 parts |
| | γ-butyrolactone | 3 parts |

The following components were mixed and dissolved, further, filtrated through a fluorine resin filter having pore diameter of 0.2 μm, to prepare photoresist compositions.

Resin (kind and amount are described in Table 1)

Acid generator (kind and amount are described in Table 1)

Basic compound (kind and amount are described in Table 1)

Solvent Y1

TABLE 1

| Ex. No. | Resin (kind/amount (part)) | Acid Generator (kind/amount (part)) | Basic compound (kind/amount (part)) | PB(° C.)/PEB(° C.) |
|---|---|---|---|---|
| Ex. 5 | A1/10 | B1/0.90 | C1/0.04 | 100/95 |
| Ex. 6 | A2/10 | B2/1.20 | C1/0.03 | 100/95 |
| Ex. 7 | A3/10 | B2/1.20 | C1/0.03 | 100/95 |
| Comp. Ex. 1 | H1/10 | B1/0.95 | C1/0.11 | 105/105 |

Silicon wafers having a diameter of 12 inches were each coated with "SR-309", which is an organic anti-reflective coating composition available from Nissan Chemical Industries, Ltd., and then baked at 205° C. for 60 seconds, to form a 930 Å-thick organic anti-reflective coating. Each of the photoresist compositions prepared as above was spin-coated over the anti-reflective coating so that the thickness of the resulting film became 85 nm after drying. The silicon wafers thus coated with the respective photoresist compositions were each prebaked on a direct hotplate at a temperature shown in a column of "PB" in Table 1 for 60 seconds. Using an ArF excimer stepper for immersion exposure ("XT: 1900Gi"

manufactured by ASML, NA=1.35, ¾ Annular, X-Y polarization), each wafer thus formed with the respective resist film was subjected to line and space pattern immersion exposure, with the exposure quantity being varied stepwise.

After the exposure, each wafer was subjected to post-exposure baking on a hotplate at a temperature shown in column of "PEB" in Table 1 for 60 seconds and then to paddle development for 60 seconds with an aqueous solution of 2.38 wt % tetramethylammonium hydroxide.

Each of photoresist patterns developed on the organic anti-reflective coating substrate after the development was observed with a scanning electron microscope, the results of which are shown in Table 2.

Effective Sensitivity (ES): It is expressed as the amount of exposure that 50 nm line pattern and the space pattern become 1:1 after exposure and development.

Line Edge Roughness (LER): The photoresist pattern was observed with a scanning electron microscope, and the difference between the height of the highest point and height of the lowest point of the scabrous wall surface of the photoresist pattern was measured. When the difference is 5 nm or less, LER is good and its evaluation is marked by "○", and when the difference is more than 5 nm, LER is bad and its evaluation is marked by "X". The smaller the difference is, the better the photopattern is.

Exposure latitude (EL): Photoresist patterns which gave the space pattern split by the line pattern at the exposure amount of ES±10% and development were observed with a scanning electron microscope. Line widths of the obtained patterns of 50 nm line and space pattern were plotted against exposure amounts on forming the pattern to make a graph wherein a horizontal axis is an exposure amount and a vertical axis is a line width of the pattern. When the absolute value of the slope of the plotted line is 1.1 nm/(MJ/cm$^2$) or less, exposure latitude is very good and its evaluation is marked by "⊚", when the absolute value of the slope of the plotted line is more than 1.1 nm/(MJ/cm$^2$) and is 1.3 nm/(MJ/cm$^2$) or less, exposure latitude is good and its evaluation is marked by "○", and when the absolute value of the slope of the plotted line is more than 1.3 nm/(MJ/cm$^2$) and is 1.5 nm/(MJ/cm$^2$) or less, exposure latitude is normal and its evaluation is marked by "Δ", and when the absolute value of the slope of the plotted line is more than 1.5 nm/(MJ/cm$^2$) or 50 nm line and space pattern was not developed, exposure latitude is bad and its evaluation is marked by "X".

TABLE 2

| Ex. No. | LER | EL |
| --- | --- | --- |
| Ex. 5 | ○ | ⊚ |
| Ex. 6 | ○ | ○ |
| Ex. 7 | ○ | ⊚ |
| Comp. Ex. 1 | X | X |

The photoresist composition of the present invention comprising the resin of the present invention provides a good photoresist pattern having good line edge roughness and exposure latitude.

What is claimed is:

1. A compound represented by the formula (II):

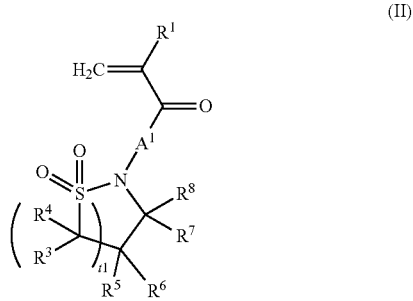

wherein $R^1$ represents a hydrogen atom, a halogen atom or a C1-C6 alkyl group which may have one or more halogen atoms, $A^1$ represents a divalent connecting group, $R^3, R^4, R^5, R^6, R^7$ and $R^8$ independently each represents a hydrogen atom or a C1-C24 hydrocarbon group, and at least two selected from $R^3, R^4, R^5, R^6, R^7$ and $R^8$ may be bonded to each other to form a ring, and one or more hydrogen atoms in the C1-C24 hydrocarbon group and the ring can be replaced by a halogen atom, a hydroxyl group, a C1-C12 alkyl group, a C1-C12 alkoxy group, a C2-C4 acyl group or a C2-C4 acyloxy group, and one or more —CH$_2$— in the C1-C24 hydrocarbon group and the ring can be replaced by —CO— or —O—, and t1 represents an integer of 0 to 3.

2. The compound according to claim 1, which is represented by the formula (III):

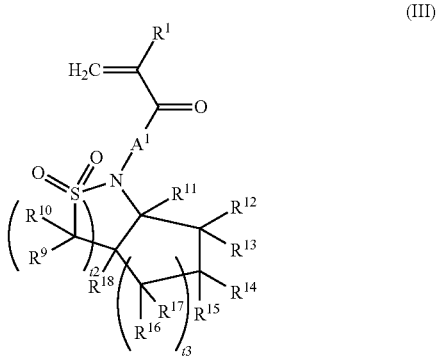

wherein $R^1$ represents a hydrogen atom, a halogen atom or a C1-C6 alkyl group which may have one or more halogen atoms, $A^1$ represents a divalent connecting group, $R^9, R^{10}, R^{11}, R^{12}, R^{13}, R^{14}, R^{15}, R^{16}, R^{17}$ and $R^{18}$ independently each represents a hydrogen atom or a C1-C12 hydrocarbon group, and at least two selected from $R^9, R^{10}, R^{11}, R^{12}, R^{13}, R^{14}, R^{15}, R^{16}, R^{17}$ and $R^{18}$ may be bonded to each other to form a ring, and one or more hydrogen atoms in the C1-C12 hydrocarbon group and the ring can be replaced by a halogen atom, a hydroxyl group, a C1-C12 alkyl group, a C1-C12 alkoxy group, a C2-C4 acyl group or a C2-C4 acyloxy group, and one or more —CH$_2$— in the C1-C12 hydrocarbon group and the ring can be replaced by —CO— or —O—, and t2 and t3 independently each represents an integer of 0 to 3.

3. The compound according to claim 2, which is represented by the formula (IV):

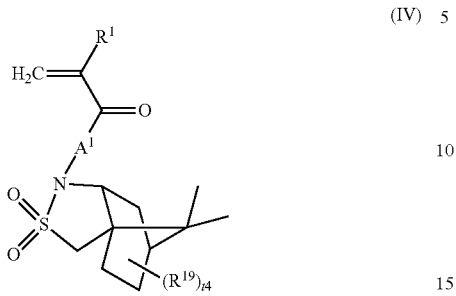

wherein $R^1$ represents a hydrogen atom, a halogen atom or a C1-C6 alkyl group which may have one or more halogen atoms, $A^1$ represents a divalent connecting group, $R^{19}$ represents a halogen atom, a hydroxyl group, a C1-C12 alkyl group, a C1-C12 alkoxy group, a C2-C4 acyl group or a C2-C4 acyloxy group, and t4 represents an integer of 0 to 8.

* * * * *